US012626149B2

(12) United States Patent
Jung et al.

(10) Patent No.:    US 12,626,149 B2
(45) Date of Patent:        May 12, 2026

(54) ELECTRONIC DEVICE AND METHOD FOR RECOGNIZING USAGE OF BODY PART AND STATE OF USER USING KNOWLEDGE GRAPH

(71) Applicant: SAMSUNG ELECTRONICS CO., LTD., Suwon-si (KR)

(72) Inventors: Jinhe Jung, Suwon-si (KR); Gibeom Park, Suwon-si (KR); Sungmok Seo, Suwon-si (KR); Chaeseung Lim, Suwon-si (KR); Myunghee Han, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 870 days.

(21) Appl. No.: 17/722,399

(22) Filed:       Apr. 18, 2022

(65)               Prior Publication Data

US 2023/0004821 A1      Jan. 5, 2023

Related U.S. Application Data

(63) Continuation       of       application       No. PCT/KR2022/004902, filed on Apr. 5, 2022.

(30)        Foreign Application Priority Data

Jun. 30, 2021    (KR) ........................ 10-2021-0085517

(51) Int. Cl.
*G06N 5/02*          (2023.01)
*A61B 5/11*          (2006.01)
*G06F 3/01*          (2006.01)
(52) U.S. Cl.
CPC .................. *G06N 5/02* (2013.01); *A61B 5/11* (2013.01); *G06F 3/011* (2013.01)

(58) Field of Classification Search
CPC .. G06N 5/02; G06N 3/04; G06N 3/08; G06N 5/022; A61B 5/11; A61B 5/0077;
(Continued)

(56)               References Cited

U.S. PATENT DOCUMENTS 8,019,813 B2      9/2011  Pope et al.
8,881,064 B2    11/2014  Geurts et al.
(Continued)

FOREIGN PATENT DOCUMENTS

JP          2020060861 A      4/2020
KR      20100106432 A     10/2010
(Continued)

OTHER PUBLICATIONS

International Search Report and Written Opinion for International Application No. PCT/KR2022/004902; International Filing Date Apr. 5, 2022; Date of Mailing Jul. 18, 2022; 7 Pages.
(Continued)

*Primary Examiner* — Pei Yong Weng
(74) *Attorney, Agent, or Firm* — CANTOR COLBURN LLP

(57)               ABSTRACT

A method of an electronic device is provided. The method includes obtaining, from a memory of the electronic device, information indicating a usage relationship between distinct states of a user of the electronic device and at least one body part, identifying a first state of the user corresponding to a first function among a plurality of functions executable by the electronic device, identifying an event for executing a second function different from the first function, comparing, in response to identifying the event, a first body part used by the user associated with the first state and a second body part used by the user associated with a second state corresponding to the second function, based on the obtained information, and executing, in response to the identified event, a
(Continued)

third function indicated in the information as being associated with the second function, based on a result of the comparing.

15 Claims, 25 Drawing Sheets

(58) Field of Classification Search
CPC .......... A61B 2562/0219; A61B 5/7267; A61B 5/7282; A61B 5/7285; A61B 5/0002; G06F 3/011; G06F 11/327; G06F 13/18; G06F 18/22; G06Q 10/1093; H04M 1/72454; G06T 11/206; G06V 40/10
See application file for complete search history.

(56) References Cited

U.S. PATENT DOCUMENTS

| | | | |
|---|---|---|---|
| 9,600,769 | B1 | 3/2017 | Liu et al. |
| 10,482,139 | B2 | 11/2019 | Khaitan et al. |
| 11,874,885 | B2 | 1/2024 | Jeong et al. |
| 2009/0119603 | A1 | 5/2009 | Stackpole |
| 2010/0257491 | A1* | 10/2010 | Geurts .................... G06F 3/017<br>715/863 |
| 2012/0204133 | A1* | 8/2012 | Guendelman ........... G06F 3/017<br>715/863 |
| 2014/0310621 | A1 | 10/2014 | Geurts et al. |
| 2021/0089598 | A1* | 3/2021 | Jeong ................. G06F 16/9024 |
| 2022/0334650 | A1* | 10/2022 | Huang .................... G06F 3/015 |

FOREIGN PATENT DOCUMENTS

| | | |
|---|---|---|
| KR | 20170047117 A | 5/2017 |
| KR | 101767828 B1 | 8/2017 |
| KR | 20180092750 A | 8/2018 |
| KR | 20210033770 A | 3/2021 |

OTHER PUBLICATIONS

International Search Report with English Translation for International Application No. PCT/KR2022/004902; International Filing Date May 4, 2022; Date of Mailing Jul. 18, 2022; 9 pages.
Korean Decision of Grant; Application No. 10-2021-0085517; Mailed Jul. 30, 2025, 2 pages; with English Translation.

* cited by examiner

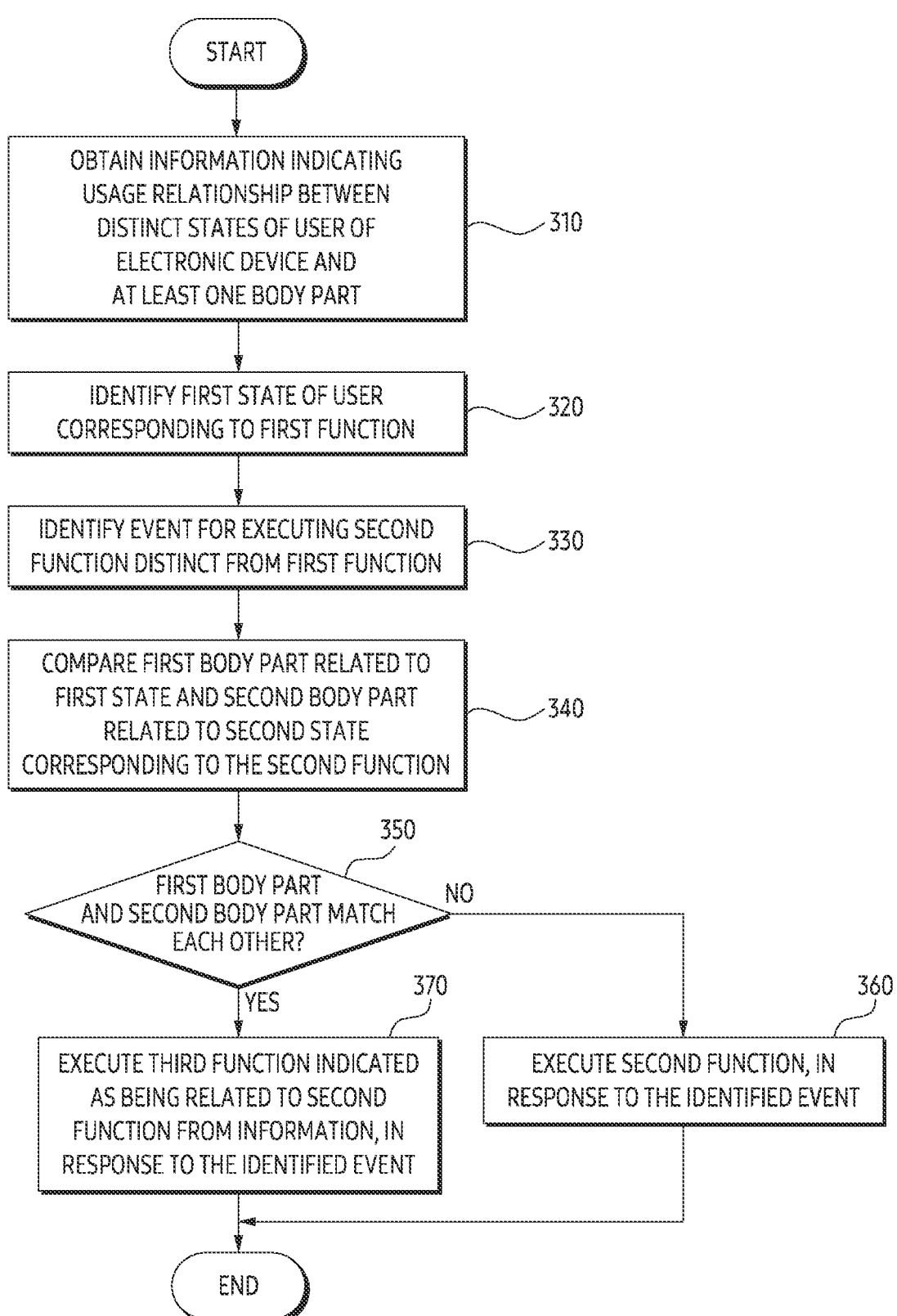

START

OBTAIN INFORMATION INDICATING USAGE RELATIONSHIP BETWEEN DISTINCT STATES OF USER OF ELECTRONIC DEVICE AND AT LEAST ONE BODY PART ⟶ 310

IDENTIFY FIRST STATE OF USER CORRESPONDING TO FIRST FUNCTION ⟶ 320

IDENTIFY EVENT FOR EXECUTING SECOND FUNCTION DISTINCT FROM FIRST FUNCTION ⟶ 330

COMPARE FIRST BODY PART RELATED TO FIRST STATE AND SECOND BODY PART RELATED TO SECOND STATE CORRESPONDING TO THE SECOND FUNCTION ⟶ 340

350
FIRST BODY PART AND SECOND BODY PART MATCH EACH OTHER?

NO

YES

EXECUTE THIRD FUNCTION INDICATED AS BEING RELATED TO SECOND FUNCTION FROM INFORMATION, IN RESPONSE TO THE IDENTIFIED EVENT ⟵ 370

EXECUTE SECOND FUNCTION, IN RESPONSE TO THE IDENTIFIED EVENT ⟵ 360

END

FIG. 3

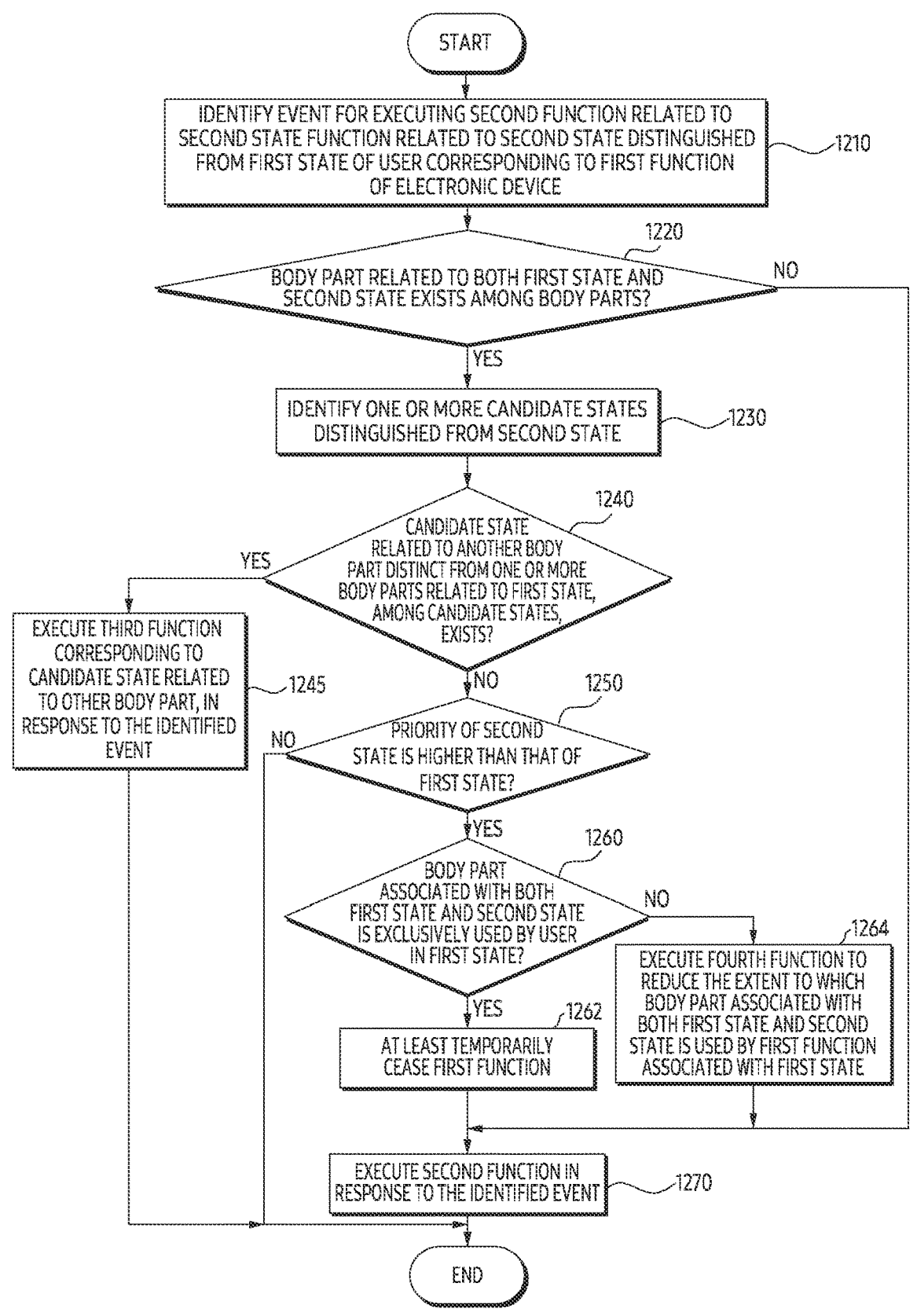

START

IDENTIFY EVENT FOR EXECUTING SECOND FUNCTION RELATED TO
SECOND STATE FUNCTION RELATED TO SECOND STATE DISTINGUISHED
FROM FIRST STATE OF USER CORRESPONDING TO FIRST FUNCTION
OF ELECTRONIC DEVICE — 1210

BODY PART RELATED TO BOTH FIRST STATE AND
SECOND STATE EXISTS AMONG BODY PARTS? — 1220
NO

YES

IDENTIFY ONE OR MORE CANDIDATE STATES
DISTINGUISHED FROM SECOND STATE — 1230

CANDIDATE STATE
RELATED TO ANOTHER BODY
PART DISTINCT FROM ONE OR MORE
BODY PARTS RELATED TO FIRST STATE,
AMONG CANDIDATE STATES,
EXISTS? — 1240

YES

EXECUTE THIRD FUNCTION
CORRESPONDING TO
CANDIDATE STATE RELATED
TO OTHER BODY PART, IN
RESPONSE TO THE IDENTIFIED
EVENT — 1245

NO

PRIORITY OF SECOND
STATE IS HIGHER THAN THAT OF
FIRST STATE? — 1250
NO

YES

BODY PART
ASSOCIATED WITH BOTH
FIRST STATE AND SECOND STATE
IS EXCLUSIVELY USED BY USER
IN FIRST STATE? — 1260
NO

EXECUTE FOURTH FUNCTION TO
REDUCE THE EXTENT TO WHICH
BODY PART ASSOCIATED WITH
BOTH FIRST STATE AND SECOND
STATE IS USED BY FIRST FUNCTION
ASSOCIATED WITH FIRST STATE — 1264

YES

AT LEAST TEMPORARILY
CEASE FIRST FUNCTION — 1262

EXECUTE SECOND FUNCTION IN
RESPONSE TO THE IDENTIFIED EVENT — 1270

END

FIG. 12

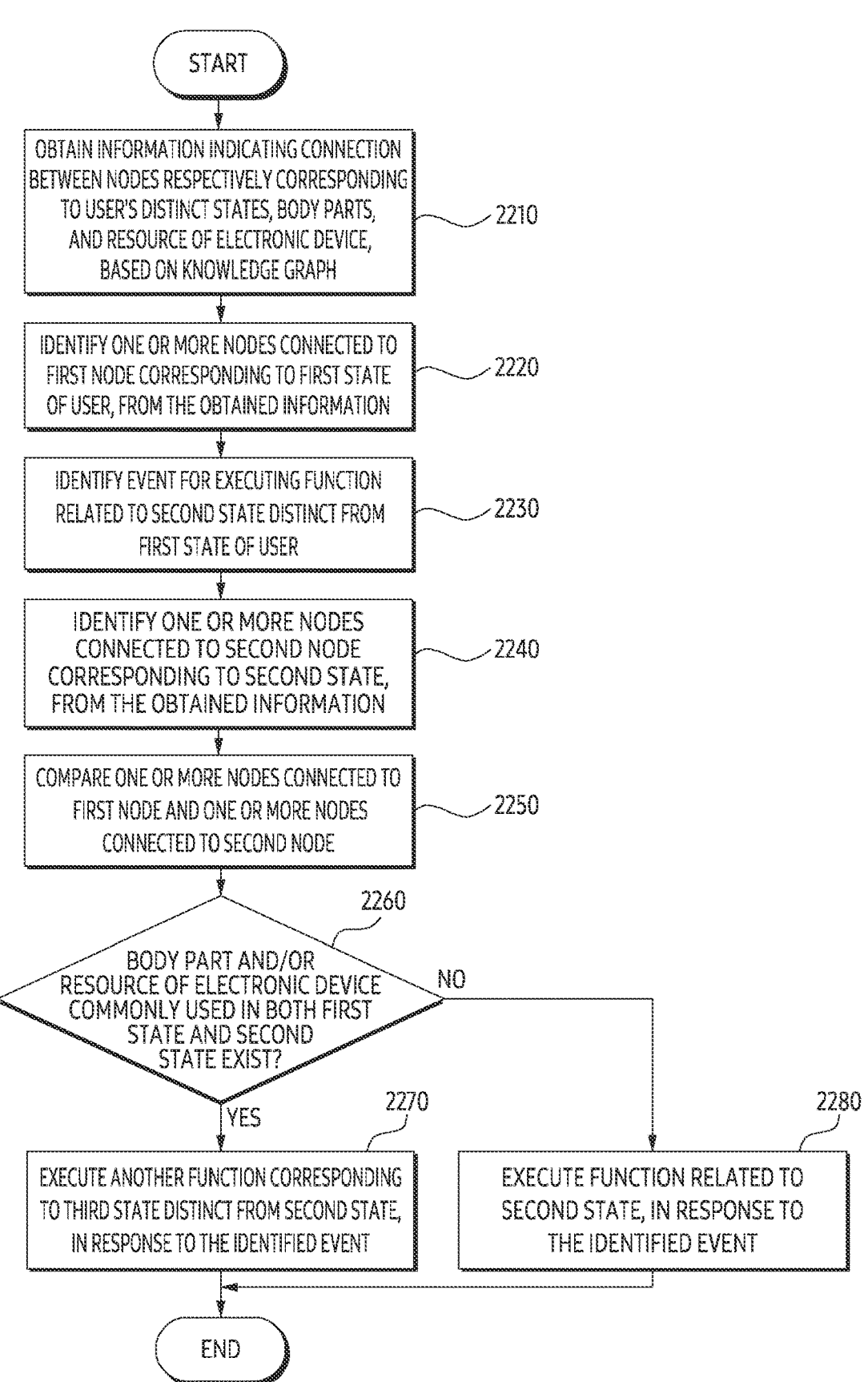

START

OBTAIN INFORMATION INDICATING CONNECTION BETWEEN NODES RESPECTIVELY CORRESPONDING TO USER'S DISTINCT STATES, BODY PARTS, AND RESOURCE OF ELECTRONIC DEVICE, BASED ON KNOWLEDGE GRAPH — 2210

IDENTIFY ONE OR MORE NODES CONNECTED TO FIRST NODE CORRESPONDING TO FIRST STATE OF USER, FROM THE OBTAINED INFORMATION — 2220

IDENTIFY EVENT FOR EXECUTING FUNCTION RELATED TO SECOND STATE DISTINCT FROM FIRST STATE OF USER — 2230

IDENTIFY ONE OR MORE NODES CONNECTED TO SECOND NODE CORRESPONDING TO SECOND STATE, FROM THE OBTAINED INFORMATION — 2240

COMPARE ONE OR MORE NODES CONNECTED TO FIRST NODE AND ONE OR MORE NODES CONNECTED TO SECOND NODE — 2250

2260

BODY PART AND/OR RESOURCE OF ELECTRONIC DEVICE COMMONLY USED IN BOTH FIRST STATE AND SECOND STATE EXIST?

NO

YES

2270

EXECUTE ANOTHER FUNCTION CORRESPONDING TO THIRD STATE DISTINCT FROM SECOND STATE, IN RESPONSE TO THE IDENTIFIED EVENT

2280

EXECUTE FUNCTION RELATED TO SECOND STATE, IN RESPONSE TO THE IDENTIFIED EVENT

END

FIG. 22

ELECTRONIC DEVICE AND METHOD FOR RECOGNIZING USAGE OF BODY PART AND STATE OF USER USING KNOWLEDGE GRAPH

CROSS-REFERENCE TO RELATED APPLICATION(S)

This application is a continuation of PCT International Application No. PCT/KR2022/004902, which was filed on Apr. 5, 2022, and claims priority to Korean Patent Application No. 10-2021-0085517, filed on Jun. 30, 2021, in the Korean Intellectual Property Office, the disclosure of which are incorporated by reference herein their entirety.

BACKGROUND

Technical Field

Embodiments of the disclosure relate to an electronic device and method for recognizing usage of one or more body parts and state of a user using a knowledge graph.

Description of Related Art

Various technological developments related to an electronic device equipped with artificial intelligence (AI) technology are in progress. An electronic device to which artificial intelligence technology is applied may learn and determine a surrounding situation by itself, independently of updating instructions by external signals. As the electronic device, to which the artificial intelligence technology is applied, learns and determines a surrounding situation in an active manner, it is possible to automatically respond to any situation requiring a human determination based on the electronic device.

Artificial intelligence technology may encompass machine learning technology, reasoning technology, searching technology, planning technology, knowledge representation technology and so on. The machine learning technology may include, after an electronic device changes a set of parameters such as, e.g., a neural network by itself, based on learning data, to learn result data corresponding to the learning data, a technology that causes the result data corresponding to other data distinct from the learning data to be output. The reasoning technology may include a technique that causes an electronic device to obtain rules and/or facts from data. The searching technology may include a technique that allows an electronic device to search for a space including a possible solution to obtain an optimal solution to address a problem. The planning technique may include a technique that causes an electronic device to create, by itself, a sequence of functions to be executed in order to achieve a certain goal. The knowledge representation technology may include a technique that makes an electronic device automatically process human thoughts and/or knowledge.

SUMMARY

As a variety of electronic devices are personalized for a respective specific user, a demand may be made on a method for causing the electronic device to operate based on a result of recognizing and/or predicting the behavior of a specific user.

As an electronic device provides multiple functions, a demand may be made on a method of selectively executing at least one function among the multiple functions, based on a result of recognizing the user's action by the electronic device.

The technical problem to be achieved in this document is not limited to those described above, and other technical problems not mentioned herein will be clearly understood by those of ordinary skill in the art to which the present disclosure belongs from the following description.

A method of an electronic device, according to an embodiment, includes obtaining, from a memory of the electronic device, information indicating a usage relationship between distinct states of a user of the electronic device and at least one body part; identifying a first state of the user corresponding to a first function among multiple functions executable by the electronic device; identifying an event for executing a second function different from the first function; comparing, in response to identifying the event, a first body part used by the user associated with the first state and a second body part used by the user associated with a second state corresponding to the second function, based on the obtained information; and executing, in response to the identified event, a third function that is indicated in the information as being associated with the second function, based on a result of the comparing.

An electronic device, according to an embodiment, includes a memory, and at least one processor operably coupled to the memory, where the memory stores one or more instructions that cause, when executed by the at least one processor, the at least one processor to obtain, from the memory, information indicating a usage relationship between distinct states of a user of the electronic device and at least one body part; identify a first state of the user corresponding to a first function among multiple functions executable by the electronic device; identify an event for executing a second function different from the first function; compare, in response to identification of the event, a first body part used by the user associated with the first state and a second body part used by the user associated with a second state corresponding to the second function based on the obtained information; and execute, in response to the identified event, a third function that is indicated in the information as being associated with the second function based on a result of the comparing.

An electronic device, according to an embodiment, includes a communication circuitry, a memory, and at least one processor operably coupled to the communication circuitry and the memory, where the memory stores one or more instructions that cause, when executed by the at least one processor, the at least one processor to obtain, from the memory, information indicating usage relationship between distinct states of a user of the electronic device and at least one body part; identify, based on the obtained information, one or more first body parts used by the user in a first state, among the distinct states, associated with a first function that has been executed by the electronic device; receive, from an external electronic device via the communication circuitry, a signal requesting outputting a notification message to the user; identify, in response to receiving of the signal, change in usage of the one or more first body parts according to a second state, among the distinct states, indicating receiving of the notification message of the user, based on the obtained information; provide, in response to identifying the change in usage of the one or more first body parts, a first control signal for adjusting the first function; and output, while providing the first control signal, the notification message based on the received signal to the user.

A method of an electronic device, according to an embodiment, includes obtaining, from the memory, information indicating usage relationship between distinct states of a user of the electronic device and at least one body part; identifying, based on the obtained information, one or more first body parts used by the user in a first state, among the distinct states, associated with a first function that has been executed by the electronic device; receiving, from an external electronic device via the communication circuitry, a signal requesting outputting a notification message to the user; identifying, in response to the receiving of the signal, a change in usage of the one or more first body parts according to a second state, among the distinct states, indicating receiving of the notification message of the user, based on the obtained information; providing, in response to identifying the change in usage of the one or more first body parts, a first control signal for adjusting the first function; and outputting, while providing the first control signal, the notification message based on the received signal to the user.

A computer program product, according to an embodiment, includes a computer-readable recording medium, the computer-readable recording medium including instructions which are readable by at least one processor of an electronic device to cause the at least one processor to: obtain information indicating a usage relationship between distinct states of a user of the electronic device and at least one body part; identify a first state of the user corresponding to a first function among a plurality of functions executable by the electronic device; identify an event for executing a second function different from the first function; compare, in response to identifying the event, a first body part used by the user associated with the first state and a second body part used by the user associated with a second state corresponding to the second function, based on the obtained information; and execute, in response to the identified event, a third function indicated in the information as being associated with the second function, based on a result of the comparing.

A method of an electronic device, according to an embodiment, includes identifying a first state of a user corresponding to a first function based on information indicated in a knowledge graph; identifying an event to execute a second function related to a second state distinguished from the first state of the user corresponding to the first function; determining whether a body part related to both the first state and the second state exists in the knowledge graph; identifying a candidate state distinguished from the second state in response to determining that the body part related to both the first state and the second state exists in the knowledge graph; and executing a third function corresponding to the candidate state related to another body part, in response to the identified event.

The advantageous effect that can be obtained from this disclosure is not limited to those described above, and other effects not mentioned herein will be understood by those skilled in the art to which the present disclosure belongs from the following description.

BRIEF DESCRIPTION OF THE DRAWINGS

For a more complete understanding of this disclosure and its advantages, reference is now made to the following description, taken in conjunction with the accompanying drawings, in which:

FIG. 3 is a flowchart illustrating an operation of an electronic device according to an embodiment;

FIG. 12 is a flowchart illustrating an operation for controlling, by an electronic device, at least one of a user's state and another state related to an event, according to an embodiment;

FIG. 22 is a flowchart illustrating an operation performed by an electronic device based on a knowledge graph indicating a user's body part and a resource usage of the electronic device, according to an embodiment;

DETAILED DESCRIPTION

Figure 1:
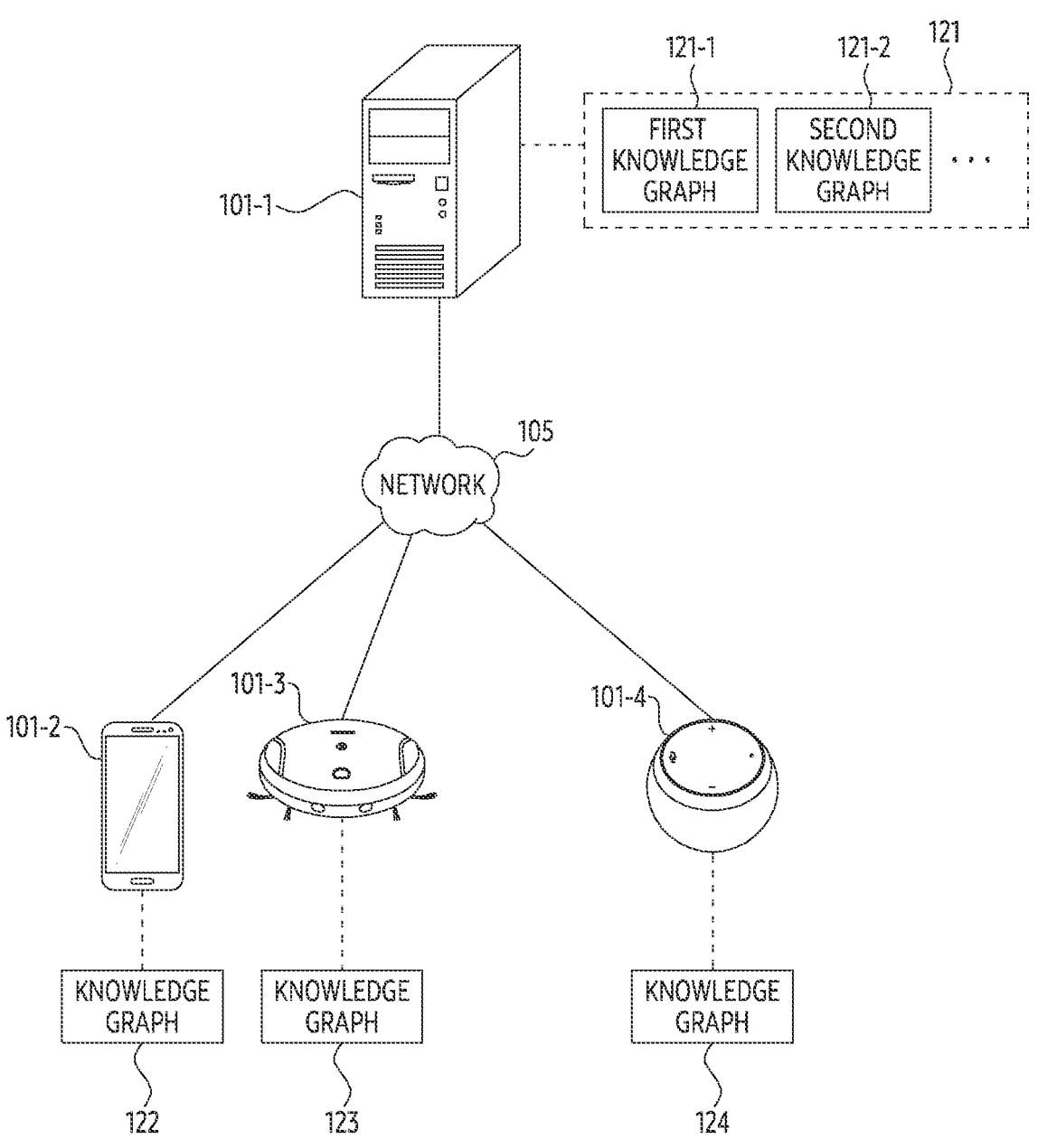
FIG. 1 is a diagram illustrating an embodiment of electronic devices connected to each other through a network.

The electronic device, according to an embodiment, can recognize and/or predict a user's action, and based on a result of recognizing and/or predicting the user's action, selectively execute one or more functions provided by the electronic device.

The electronic device, according to an embodiment, can monitor the state of the user's body parts and selectively execute at least one function among multiple functions based on the monitored state.

Hereinafter, various embodiments of the present disclosure will be described with reference to the accompanying drawings.

Various embodiments of the disclosure and the terms used herein are not intended to limit the technology described to a specific embodiment, and should be understood to include various modifications, equivalents, and/or substitutions of those embodiments. In connection with the description of the drawings, like reference numerals may be used for like components. A singular expression may include a plural expression, unless the context clearly dictates otherwise. Expressions such as "A or B", "at least one of A and/or B", "A, B or C" or "at least one of A, B and/or C" may include all the possible combinations of the items listed together. Expressions such as "first", "second" or the like may modify the corresponding elements regardless of their order or importance and are used only to distinguish one element from another element and not intended to limit the corresponding elements thereto. When a certain (e.g., a first) element is referred to as being "(functionally or communicatively) connected" or "coupled" to another (e.g., a second) element, the element (e.g., the first) may be either directly connected to the other element (e.g., the second) or may be connected through another element (e.g., a third component).

The terminology used herein is for the purpose of describing particular embodiments only and is not intended to be limiting. As used herein, "a", "an," "the," and "at least one" do not denote a limitation of quantity, and are intended to include both the singular and plural, unless the context clearly indicates otherwise. For example, "an element" has the same meaning as "at least one element," unless the context clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper*" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the term "module" may include a unit composed of hardware, software, and/or firmware, and may be used interchangeably with terms such as, for example, logic, logic block, component, or circuit. A module may be of an integrally formed component or a minimum unit or a part thereof performing one or more functions. For example, the module may be configured as an application-specific integrated circuit (ASIC).

Functions related to artificial intelligence, according to the present disclosure, may operate on a processor and a memory. The processor may include one or more processors. In this context, the one or more processors may be a general-purpose processor, such as, e.g., a central processing unit (CPU), an application processor (AP), a digital signal processor (DSP) or the like, a graphics dedicated processor such as e.g., a graphics processing unit (GPU), a vision processing unit (VPU), or an artificial intelligence (AI) dedicated processor such as a neural processing unit (NPU). The one or more processors may control to process input data according to a predefined operation rule or an artificial intelligence model stored in the memory. Alternatively, when the one or more processors are of an AI-dedicated processor, the AI-dedicated processor may be designed with a hardware structure specialized for processing a certain AI model.

Such a predefined action rule or artificial intelligence model is characterized in that it is made based on learning. Here, being made based on learning may imply that a basic artificial intelligence model is learned using a plurality of learning data through a learning algorithm, so that it can be made a predefined action rule or an artificial intelligence model configured to perform a desired characteristic (or purpose). Such learning may be performed on an apparatus itself on which the artificial intelligence, according to the present disclosure, is performed or may be performed on a separate server and/or a system. Examples of the learning algorithm may include supervised learning, unsupervised learning, semi-supervised learning, or reinforcement learning, although not limited thereto.

An artificial intelligence model may be configured with a plurality of neural network layers. Each of the plurality of neural network layers may have a plurality of weight values and may perform a neural network operation through operations between an operational result of a previous layer and a plurality of weight values. The plurality of weights of the plurality of neural network layers may be optimized by a result of learning from an artificial intelligence model. For example, a plurality of weights may be updated so that a loss value or a cost value obtained from the artificial intelligence model during the learning process is reduced or minimized. Examples of the artificial neural network may include, for example, a convolutional neural network (CNN), a deep neural network (DNN), a recurrent neural network (RNN), a restricted Boltzmann machine (RBM), a deep belief network (DBN), a bidirectional recurrent deep neural network (BRDNN), or deep Q-networks, although it is not limited thereto.

According to a method of an electronic device, according to the present disclosure, with a view to recognizing a user's state or for recognizing a user's voice to interpret an intention for executing a function that may be provided by the electronic device, the electronic device can receive an analog voice signal through a microphone and then convert the voice signal into a computer-readable text using an automatic speech recognition (ASR) model. By using a natural language understanding (NLU) model to interpret the converted text, it is possible to obtain the user's intention to speak. Here, the ASR model or the NLU model may be of an AI model. The AI model can be processed by an AI-dedicated processor designed with a hardware structure specialized for processing the AI model. An AI model may be created through learning. Here, when an AI model is created through learning, it will imply that a basic AI model is learned using a plurality of learning data by a certain learning algorithm, so as to render a predefined action rule or AI model set to perform a desired characteristic (or purpose). An AI model may be configured with a plurality of neural network layers. Each of the plurality of neural network layers may have a plurality of weight values and implement a neural network operation by performing operations between an operation result of a previous layer and the plurality of weight values.

Linguistic understanding may be one of a plurality of advanced techniques of recognizing and applying/processing human language/character, and may include natural language processing, a machine translation, a dialog system, a question answering system, a speech recognition/synthesis, and the like.

According to a method of an electronic device, according to the present disclosure, with a view to recognizing a user's state, the electronic device may use image data as input data to an AI model to obtain output data recognizing an image or a user in the image. An AI model may be created through learning. Here, such an AI model being created through learning may imply that a basic AI model is learned using a plurality of learning data by a certain learning algorithm, so as to render a predefined action rule or AI model set to perform a desired characteristic (or purpose). An AI model may be composed of a plurality of neural network layers. Each of the plurality of neural network layers may have a plurality of weight values and may perform a neural network operation through operations between an operation result of a previous layer and the plurality of weight values.

Visual understanding may be one of a plurality of advanced techniques of recognizing and processing an object like human vision, and may include object recognition, object tracking, image retrieval, human recognition, scene recognition, spatial recognition (e.g., three-dimensional (3D) reconstruction/localization), image enhancement, and so on.

According to a method of an electronic device, according to the present disclosure, with a view to inferring or predicting a state of a user, the electronic device may utilize an AI model for executing another function related to another state distinct from a state corresponding to a requested function, using a knowledge graph. A processor of the electronic device may perform a pre-processing process on the data to convert it into a form suitable for use as an input to the AI model. AI models may be created through learning. Here, the AI model being created through learning may imply that a basic artificial intelligence model is learned using a plurality of learning data by a certain learning algorithm, so as to create a predefined action rule or AI model established to perform a desired characteristic (or purpose). The AI model may be configured with a plurality of neural network layers. Each of the plurality of neural network layers may have a plurality of weight values and may perform a neural network operation through operations between an operation result of a previous layer and the plurality of weight values.

Inference prediction may be one of a plurality of advance techniques for judging information for making logical reasoning and prediction, and include knowledge/probability-based reasoning, optimization prediction, preference-based planning, recommendation, and so on.

FIG. 1 is a diagram illustrating an embodiment of electronic devices 101-1, 101-2, 101-3 and 101-4 connected with each other over a network 105. Referring to FIG. 1, an example configuration is depicted in which the electronic devices 101-1, 101-2, 101-3 and 101-4 are connected to each other over the network 105, which may be a wired network, an optical network, and/or a wireless network. Hardware components included in the electronic devices 101-1, 101-2, 101-3 and 101-4 will be described later with further reference to FIG. 2.

The wired network may include a communication network such as e.g., Internet, a local area network (LAN), a wide area network (WAN), Ethernet, or a combination thereof. The wireless network may include a communication network such as e.g., Long Term Evolution (LTE), 5G New Radio (NR), Wireless Fidelity (WiFi), Zigbee, Near Field Communication (NFC), Bluetooth, Bluetooth Low-Energy (BLE), or a combination thereof. Although not illustrated herein, the electronic devices 101-1, 101-2, 101-3 and 101-4 may be indirectly connected with each other via one or more routers, switches and/or access points. Further, the network 105 can use one or more waveguides, optical fiber, and/or other such communication mediums.

Referring with continued reference to FIG. 1, the electronic device 101-1, according to an embodiment, may include a server of a certain service provider. The server may include one or more personal computers (PCs) and/or workstations. In one embodiment, the service provider may run on services for enhancing the user experience (i.e., User eXperience: UX) of subscribers.

Referring to FIG. 1, the electronic devices 101-2, 101-3 and 101-4 may be any kind of terminals that are owned by a user. The term "owned" as used herein can indicate that an item is accessible, usable, or possessed by one or more users and does not require ownership in a legal sense. Like the electronic device 101-2 shown in FIG. 1, the terminals may include, for example, a PC, such as, e.g., a laptop and/or a desktop, a smartphone, and a smart pad, a tablet PC, a smart watch, and/or a smart accessory, such as, e.g., a head-mounted device (HMD). Like the electronic devices 101-3 and 101-4 shown in FIG. 1, the terminal may include, for example, a home appliance, such as, e.g., a vacuum cleaner, a speaker, a refrigerator, an air-conditioner, and/or a television (TV). Each of the electronic devices 101-2, 101-3 and 101-4 may be owned by either a different user and/or the same user, and the user may be a subscriber of a service provided by the electronic device 101-1.

The electronic devices 101-1, 101-2, 101-3 and 101-4, according to an embodiment, may provide one or more functions to a user who owns/accesses the electronic devices 101-2, 101-3 and 101-4. For example, the electronic device 101-2 may provide a multiplicity of communication-related functions, such as, e.g., voice call, video call, and Internet access, in addition to one or more functions on an application program based on one or more instructions that can be executed by an application processor (AP) of the electronic device 101-2. For example, the electronic device 101-3 may be a robot cleaner that is an example of a state-of-the-art home appliance, providing a cleaning service within a predetermined reachable area, based on autonomous driving. For example, the electronic device 101-4 may be a speaker that provides speech recognition based on AI, performing a desired function indicated by natural language included in a user's speech.

The electronic device 101-1 may communicate with the electronic devices 101-2, 101-3 and 101-4 to provide one or more functions to users of the electronic devices 101-2, 101-3 and 101-4. For example, the electronic device 101-1 may cause information to exchange in between the electronic devices 101-2, 101-3 and 101-4, via communications with the electronic devices 101-2, 101-3 and 101-4. The electronic devices 101-2, 101-3 and 101-4 may independently communicate with the electronic device 101-1, based on a topology, such as peer-to-peer (P2P), although the embodiments are not limited thereto.

The electronic devices 101-1, 101-2, 101-3 and 101-4, according to an embodiment, may provide one or more functions related to a users state. Here, the term "use's state" may refer to an action of a user that can be distinguished by a designated identifier (ID) and may imply a unit for recognizing a user's action by the electronic devices 101-1, 101-2, 101-3 and 101-4, such as, for example, 'waking up', 'leaving home', 'arriving at office', 'going to bed, or the like. The electronic devices 101-1, 101-2, 101-3 and 101-4, according to an embodiment, may selectively perform one or more of a plurality of functions based on a current state of the user. The operation of the electronic devices 101-1, 101-2, 101-3 and 101-4 selectively performing one or more of the plurality of functions based on a current state of a user will be further described later with reference to FIGS. 3, FIGS. 10 to 18, and FIGS. 22 to 25.

Referring to FIG. 1, the electronic devices 101-1, 101-2, 101-3 and 101-4, according to an embodiment, may, for performing one or more operations based on a use's state, generate, store and/or exchange knowledge graphs 121, 121-1, 121-2, 122, 123 and 124 in which information related to the user and the electronic device is structuralized. Hereinafter, the term 'knowledge graph' may refer to information structuralize based on ontology, which may be an example of a knowledge representation to express information in a form recognizable by an electronic device. For example, the knowledge graph may be expressed based on formats defined in resource description framework (RDF), web ontology language (OWL), and/or semantic web rule language (SWRL).

For example, a knowledge graph expressed based on OWL may include classes having a hierarchy and may include one or more relations representing a connection between the class including attributes and/or an instance. In one embodiment, the class and/or instance may be referred to as an entity and/or a node. In an embodiment, the entity may mean an object named in the real world. In one embodiment, the relation may be referred to as an edge. In an embodiment, the edge may indicate a connection between entities, and may indicate a connection relationship between the entities. In an embodiment, the entity may refer to each of the objects connected to each other by the edge in the above-described knowledge graph. In an embodiment, the attributes may refer to data assigned to each of the nodes of the knowledge graph.

In an embodiment, the knowledge graph may mean information that structuralized a user's action in an ontology form based on its state and order. Referring to FIG. 1, the electronic device 101-1 controlled by a service provider may store a knowledge graph 121 corresponding to each subscriber. For example, in the knowledge graph 121, a first knowledge graph 121-1 may be a knowledge graph corresponding to a first user, and a second knowledge graph 121-2 may be a knowledge graph corresponding to a second user. Referring to FIG. 1, the knowledge graphs 122, 123 and 124 stored in each of the electronic devices 101-2, 101-3 and 101-4 that are owned by the user may mean information that structuralized a users action monitored by the corresponding electronic device. An operation of the electronic devices 101-1, 101-2, 101-3 and 101-4, according to an embodiment, can include generating a knowledge graph related to a user's action and will be described later with further reference to FIGS. 4 to 7.

The electronic devices 101-1, 101-2, 101-3 and 101-4, according to an embodiment, may carry out another function distinct from a function causing a transition of a users current state, among a plurality of functions. For example, while the user listens to music using the electronic device 101-4, the electronic device 101-2 may selectively perform another function that can be executed independently of listening to music of the user. In order to selectively perform such a function executable independently of the users current state, the electronic device 101-2 may use the knowledge graph 122 to identify a body part that is distinguished from a body part used by the user in the current state, and/or used in part by the user, among the user's body parts. In an embodiment, the knowledge graphs 121, 121-1, 121-2, 122, 123 and 124 may include information structuralizing a users state and one or more body parts used by the state. The operation of the electronic devices 101-1, 101-2, 101-3 and 101-4, according to an embodiment, identifying one or more body parts related to the user's state, using the knowledge graphs 121, 121-1, 121-2, 122, 123 and 124, will be described later with further reference to FIGS. 8 and 9.

The electronic devices 101-1, 101-2, 101-3 and 101-4, according to an embodiment, may share at least part of the knowledge graph stored in each of the electronic devices

101-1, 101-2, 101-3 and 101-4. The sharing of the knowledge graph between the electronic devices 101-2, 101-3 and 101-4 owned by the user may be, for example, mediated by the electronic device 101-1, or performed by direct communication such as, e.g., P2P. For example, in order to protect private information, in a situation where a first user of the electronic device 101-2 establishes a call connection to a second user of the electronic device 101-3, each of the electronic devices 101-2 and 101-3 may extract a portion corresponding to the state related to the call connection of the knowledge graphs 122 and 123. Each of the electronic devices 101-2 and 101-3 may exchange and/or share the extracted portion of the knowledge graph to select any one of a plurality of call connection methods (e.g., a video call, a voice over internet protocol (VoIP) call and/or a voice call), based on states of the first user and the second user. The operation of sharing at least a portion of the knowledge graph by the electronic devices 101-1, 101-2, 101-3 and 101-4 according to an embodiment will be described later with reference to FIGS. 19 to 21.

Figure 2:
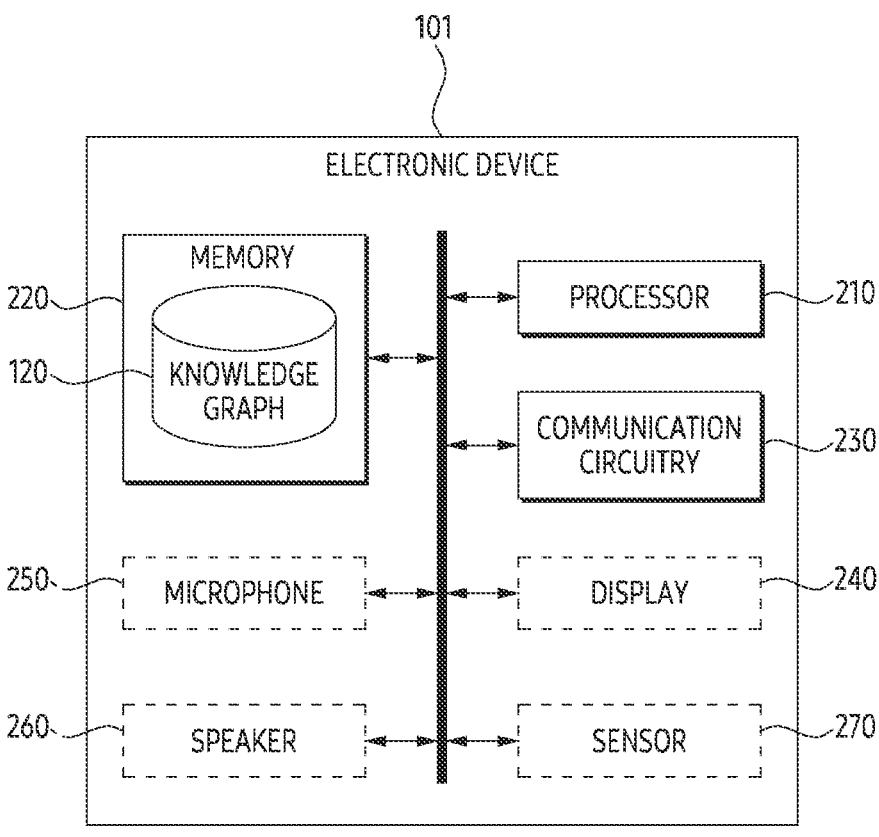
FIG. 2 is a block diagram of an electronic device according to an embodiment.

FIG. 2 is a block diagram of an electronic device 101 according to an embodiment. The electronic device 101 of FIG. 2 is an example of each of the electronic devices 101-1, 101-2, 101-3 and 101-4 of FIG. 1. Referring now to FIG. 2, the electronic device 101, according to an embodiment, may include one or more of a processor 210, a memory 220, a communication circuitry 230, a display 240, a microphone 250, a speaker 260, or a sensor 270. The processor 210, the memory 220, the communication circuitry 230, the display 240, the microphone 250, the speaker 260 and/or the sensor 270 may be electronically and/or operatively coupled with each other via electronic components such as a communication bus. The type and/or number of hardware components included in the electronic device 101 is not limited to that illustrated in FIG. 2. For example, the electronic device 101-1 of FIG. 1 may include the processor 210, the memory 220, and the communication circuitry 230 among those components described above, such as the processor 210, the memory 220, the communication circuitry 230, the display 240, the microphone 250, the speaker 260, and the sensor 270. The electronic device 101 can also include or interface with one or more effectors, such as actuators and/or other types of outputs. For example, the electronic device 101 can control one or more motors, solenoids, lights, valves, and other such outputs according to embodiments. Further, there can be one or more instance of the display 240, microphone 250, speaker 260, and/or sensor 270 incorporated within or externally connected to the electronic device 101.

The processor 210 of the electronic device 101, according to an embodiment, may include hardware components for processing data based on one or more instructions. The hardware components for processing data may include, for example, an arithmetic and logic unit (ALU), a field-programmable gate array (FPGA), a CPU, and/or other such processor types as previously described. The number of the processors 210 included in the electronic device 101 may be one or more. For example, the processor 210 may have an architecture of a multi-core processor, such as, e.g., a dual-core, a quad-core, or a hexa-core.

The memory 220 of the electronic device 101, according to an embodiment, may include a hardware component for storing data and/or instructions inputted and/or outputted to/from the processor 210. The memory 220 may include, for example, a volatile memory, such as random-access memory (RAM) and/or a non-volatile memory, such as read-only memory (ROM). The volatile memory may include, for example, at least one of a dynamic RAM (DRAM), a static RAM (SRAM), a cache RAM, and a pseudo-SRAM (PSRAM). The non-volatile memory may include, for example, at least one of a programmable ROM (PROM), an erasable PROM (EPROM), an electrically-erasable PROM (EEPROM), a flash memory, a hard disk, a compact disk, and an embedded multi-media card (eMMC).

The electronic device 101, according to an embodiment, may store the knowledge graph 120 in the memory 220. The knowledge graph 120 may include, for example, the knowledge graphs 121, 121-1, 121-2, 122, 123 and 124 of FIG. 1. The electronic device 101 may recognize the user's state by using the knowledge graph 120. Hereinafter, recognizing the user's state may imply that the electronic device 101 identifies a body part used by the user from among the user's body parts. For example, the electronic device 101 may recognize the user's current state to identify the usage of each of the user's body parts.

The memory 220 may store one or more instructions indicating an operation to be performed by the processor 210 using data. A set of instructions may be referred to as firmware, an operating system, a process, a routine, a sub-routine, a macro, and/or an application. For example, the electronic device 101 and/or the processor 210 of the electronic device 101 may be configured to execute a set of a plurality of instructions distributed in the form of an application to perform at least one of the operations of FIGS. 3, 6, 8, 10, 12, 19, and/or 22.

The communication circuitry 230 of the electronic device 101, according to an embodiment, may include a hardware component for supporting transmission and/or reception of an electrical signal in between the electronic device 101 and another electronic device. The communication circuitry 230 may include, for example, at least one of a modem, an antenna, and an optic/electronic converter. The communication circuitry 230 may support transmission and/or reception of an electrical signal based on various types of protocols such as, e.g., Ethernet, a LAN, a WAN, WiFi, Bluetooth, BLE, ZigBee, LTE, 5G NR, or the like.

The display 240 of the electronic device 101, according to an embodiment, may output visualized information to the user. For example, the display 240 may be controlled by a controller such as, e.g., a GPU to output visualized information to the user. The display 240 may include, for instance, a flat panel display (FPD) and/or electronic paper. The FPD may include, for example, a liquid crystal display (LCD), a plasma display panel (PDP), and/or one or more light emitting diodes (LEDs). The LED may include an organic LED (OLED). The display 240 may include a touch-sensitive interface operable to receive touch-based input from a user.

The electronic device 101, according to an embodiment, may include the microphone 250 to output an electrical signal representing air vibrations in the atmosphere. For example, the electronic device 101 may output an audio signal representing a users speech using the microphone 250. The user's speech included in the audio signal may be converted into information in a format recognizable by the electronic device 101 based on a speech recognition model and/or a natural language understanding model. For example, the electronic device 101 may recognize the users utterance to execute one or more functions among a plurality of functions that can be provided by the electronic device 101.

The electronic device 101, according to an embodiment, may include an output means to output information in a form other than a visualized form. For example, the electronic device 101 may include a speaker 260 to output an acoustic signal. The number of speakers 260 included in the electronic device 101 may be one or more. Although not shown, the electronic device 101 may include another output means to output the information in a form other than a visualized form and an auditory form. For example, the electronic device 101 may include a motor to provide haptic feedback based on vibrations.

The sensor 270 of the electronic device 101, according to an embodiment, may generate an electrical signal that can be processed by the processor 210 and/or the memory 220 from non-electronic information related to the electronic device 101. For example, the sensor 270 may include a global positioning system (GPS) sensor for detecting a geographic location of the electronic device 101. In addition to such a GPS scheme, the sensor 270 may generate information indicating the geographic location of the electronic device 101 based on, for example, a global navigation satellite system (GNSS) such as Galileo, Beidou, Compass, etc. The information may be stored in the memory 220, processed by the processor 210, and/or transmitted via the communication circuitry 230 to another electronic device distinct from the electronic device 101.

For example, the sensor 270 may include at least one of a gyro sensor, a gravity sensor, and/or an acceleration sensor for detecting a posture of the electronic device 101 and/or a posture of a body part of a user wearing the electronic device 101. Each of the gravity sensor and the acceleration sensor may be configured to measure acceleration and gravitational acceleration in each direction of a specified three-dimensional axis (e.g., x-axis, y-axis, and z-axis). The gyro sensor may be configured to measure angular velocity in each of the specified three-dimensional axis (e.g., x-axis, y-axis, and z-axis). The gravitational acceleration, the acceleration, and the angular velocity measured by each of the gravity sensor, the acceleration sensor, and the gyro sensor may be processed by the processor 210 and/or output in the form of an electrical signal that can be stored in the memory 220. The sensor 270 is not limited to those describe above, and may include an image sensor, an illuminance sensor, and/or a Time-of-Flight (ToF) sensor for detecting electromagnetic waves inclusive of light.

The electronic device 101 according to an embodiment may generate a knowledge graph 120 related to a users state based on log data. Hereinafter, the log data, being information collected by the electronic device 101, may be data recorded of the operation history of the electronic device 101 and/or information detected by the electronic device 101 over time. For example, the log data may include information detected in real time from the sensor 270 and/or GPS data recorded with a parameter indicating a time, such as a timestamp. For example, the log data may include data representing operation of the electronic device 101. In an embodiment, in a state that the user is using the electronic device 101, the electronic device 101 may store the states of the electronic device 101 changing by the user into the log data. For example, the log data may include various data such as, e.g., a web access history of the user of the electronic device 101, information input by the user through a designated application, such as scheduling information, a sequence of applications executed by the user using the electronic device 101, events generated by the application running on the electronic device 101, such as a software interrupt (SWI), and/or data on the state of the electronic device 101 (e.g., power. CPU utilization, memory utilization, etc.) recorded together with a parameter indicating the time, such as a timestamp. In an embodiment, the log data may be referred to as raw data. An operation of the electronic device 101 to generate the knowledge graph 120 using the raw data will be described later with reference to FIGS. 4 to 7.

Hereinafter, an operation performed by an electronic device 101 using a knowledge graph 120 according to an embodiment will be described with further reference to FIG. 3.

FIG. 3 is a flowchart illustrating an operation of an electronic device according to an embodiment. The electronic device of FIG. 3 may include the electronic devices 101-1, 101-2, 101-3 and 101-4 of FIG. 1, and/or the electronic device 101 of FIG. 2. The operation of the electronic device of FIG. 3 may be performed, for example, by the electronic device 101 and/or the processor 210 of FIG. 2.

Referring now to FIG. 3, in operation 310, the electronic device, according to an embodiment, may obtain information indicating a usage relationship between distinct states of a user of the electronic device and at least one body part. The information may indicate connections between nodes respectively corresponding to each of the distinct states of the user and the body parts, based on a knowledge graph. For example, the electronic device may identify information indicating the knowledge graph (e.g., the knowledge graph 120 of FIG. 2). The electronic device, according to an embodiment, may identify, in a memory (e.g., the memory 220 of FIG. 2), information indicating the knowledge graph for connecting in between a plurality of states and a plurality of body parts. The information identified by the electronic device may include a plurality of parameters indicating a degree in which each of the plurality of body parts of the user is used by each of the plurality of states. For example, the information identified by the electronic device may represent a knowledge graph indicating usage of at least one body part in each of the distinct states, based on connections of nodes corresponding to the distinct states and each of the body parts. For example, one or more parameters may be included in the information identified by the electronic device, representing a connection between the distinct states and the nodes corresponding thereto and each of the body parts, based on usage of a body part by the user in each of the distinct states. Each of the one or more parameters may indicate a usage of a body part corresponding to the parameter, based on a Boolean data type and/or a floating-point data type, where the Boolean data type is a data type for representing a truth value.

Referring to FIG. 3, in operation 320, the electronic device, according to an embodiment, may identify a first state of the user corresponding to a first function. In an embodiment, identifying the first state by the electronic device may include identifying, in the obtained information, a first node corresponding to the first state of the user and one or more other nodes connected to the first node. The first state may be included in any one of distinct states in the operation 310. Hereinafter, among the plurality of states, the first state of the user may be referred to as a current state of the user. For example, the electronic device may obtain first data including one or more nodes related to the user's current state, based on the information obtained in the operation 310. Since the information obtained in operation 310 indicates connections between nodes each corresponding to each of the users distinct states and body parts, the electronic device may identify a node corresponding to any one of the body parts, based on one or more nodes connected to the first node corresponding to the first state.

The electronic device, according to an embodiment, may identify a first state of the user and a first node corresponding to the first state, using schedule information corresponding to a current time. The electronic device, according to an embodiment, may identify the first state of the user and the first node corresponding to the first state, based on a state of an application in execution. The electronic device, according to an embodiment, may identify the first state of the user and the first node corresponding to the first state, based on an electric signal related to the electronic device and/or the user obtained by using a sensor (e.g., the sensor 270 of FIG. 2). In a state in which information indicating the knowledge graph is identified based on the operation 310, the electronic device, according to an embodiment, may identify the first node in the knowledge graph corresponding to the first state of the user and one or more nodes connected to the first node. The operation of the electronic device to identify the first state of the user and the first node corresponding to the first state, using the knowledge graph, will be described later with reference to FIGS. 8 to 9.

Referring to FIG. 3, in operation 330, the electronic device, according to an embodiment, may identify an event for executing a second function distinct from the first function. The event may include an action of the electronic device and/or the user changing the state of the user. The event may include an action of the electronic device and/or the user, being detectable by the electronic device. The electronic device, according to an embodiment, may execute instructions referenced by an event handler, in response to identifying the event.

The electronic device, according to an embodiment, may identify an event for executing a second function related to a second state distinct from the first state of the operation 320. The second state may be included in any one of the distinct states in the operation 310. In an embodiment, the event may be an event of at least temporarily ceasing the user's action related to the first state. In an embodiment, the first function and/or the second function may be included in a plurality of functions that may be provided to the user by the electronic device. In an embodiment, the event may include receiving a signal requesting execution of a function related to another state distinguished from the user's current state, such as, e.g., a call connection requested from another electronic device. In an embodiment, the event may include receiving, from an external electronic device, a signal indicating at least one of, e.g., an incoming call, an e-mail, and/or a text message. In an embodiment, the event may be an event occurring in the application in execution on the electronic device, such as, e.g., a notification message, and include requesting outputting of a message capable of temporarily ceasing the user's action, using haptic feedback, such as a display (e.g., a display 240 of FIG. 2), a speaker (e.g., a speaker 260 of FIG. 2) and/or vibration. The electronic device, according to an embodiment, may recognize execution of the function related to the second state, in response to identifying another node connected to a node corresponding to the first state and indicating the second state, in the knowledge graph obtained based on the operation 310.

Referring to FIG. 3, in operation 340, the electronic device, according to an embodiment, may compare a first body part related to the first state and a second body part related to a second state corresponding to the second function, based on the information obtained in the operation 310. In an embodiment, the electronic device may identify one or more nodes connected to the second node corresponding to the second state, based on the information obtained in the operation 310. For example, based on the information obtained in the operation 310, the electronic device may obtain second data including one or more nodes related to the second state of the user related to the identified event. Since the information obtained in the operation 310 indicates connections between nodes respectively corresponding to each of the user's distinct states and body parts, the electronic device may identify a node corresponding to any one of the body parts, based on one or more nodes connected to the second node corresponding to the second state.

Referring to FIG. 3, in operation 350, the electronic device, according to an embodiment, may determine whether a first body part and a second body part match each other. The electronic device, according to an embodiment, may compare one or more nodes connected to the first node corresponding to the first state and one or more nodes connected to the second node corresponding to the second state, among nodes respectively corresponding to each of the body parts to determine whether the first body part and the second body part match each other. For example, based on whether there exists a node indicating the same body part, among the one or more nodes connected to the first node and the one or more nodes connected to the second node, the electronic device may determine whether the first body part and the second body part match each other. For example, the electronic device may compare the one or more nodes connected to the first node identified in the operation 320 and the one or more nodes connected to the second node identified in the operation 340 to identify a node connected in common to the first node and the second node.

When the first body part and the second body part are distinguished from each other ('NO' in operation 350), in operation 360, the electronic device may, in response to the event identified in the operation 330, execute a second function related to the event. For example, when there is no node connected in common to the first node and the second node, among nodes corresponding to each of the body parts, the electronic device may execute the second function. When the one or more nodes connected to the first node and the one or more nodes connected to the second node are distinct from each other, among the nodes corresponding to each of the body parts, the electronic device may determine that the first body part and the second body part are different from each other. For example, the first body part and the second body part, being distinct from each other may correspond to each of the first state associated with the first node and the second state associated with the second node, respectively. Since these different body parts respectively correspond to the first and second states, the user may simultaneously perform an action related to each of the first state and the second state, using different body parts. For example, the action of the user in the first state and the action of the user in the second state may be performed independently of each other.

When the first body part and the second body part match each other ('YES' in operation 350), in operation 370, the electronic device, according to an embodiment, may execute a third function indicated as being related to the second function from the information obtained in the operation 310, in response to the event identified in the operation 330. The third function may correspond to a function distinct from the second function, among multiple functions executable by the electronic device. The third function may correspond to a third state distinct from the second state corresponding to the second function. The third state, being a state related to the event in the operation 330, may correspond to a state different from the second state in the operation 330.

In response to identifying a node connected in common to the first node corresponding to the first state and the second node corresponding to the second state, the electronic device, according to an embodiment, may determine that the first body part and the second body part match each other. The node connected in common to the first node and the second node may be, for example, a node corresponding to any one of a plurality of body parts. Since the knowledge graph stands for the relationship between the nodes based on the connection (e.g., edge) between the nodes, the fact that the node corresponding to the body part is connected in common to the first node and the second node may mean that the body part is used in both the first state corresponding to the first node and the second state corresponding to the second node. For example, it may mean that the body part is used differently in each of the first state and the second state. Since the body part is used differently in each of the first state and the second state, for example, the user in the first state may execute a second action of the body part corresponding to the second state, after ceasing a first action of the body part corresponding to the first state. For example, when the first body part and the second body part match each other, the electronic device may identify that the first state and the second state respectively corresponding to the first body part and the second body part are of a state related to the same body part.

As the third function of the operation 370 is executed, the electronic device, according to an embodiment, may cease execution of the second function related to the identified event. In the knowledge graph, the node corresponding to the third state may be connected to another node distinct from the one or more nodes connected to the first node identified in the operation 320. For example, the node corresponding to the third state may be connected to a node other than the node connected to the first node among nodes corresponding to each of the body parts. For example, the first body part indicated by the node corresponding to the first state and the other body part indicated by the node corresponding to the third state may be independent of each other. Since the first body part indicated by the node corresponding to the first state and the other body part indicated by the node corresponding to the third state are independent of each other, the user's action in the first state and the user's action in the third state may be performed independently of each other.

As described above, before simultaneously executing each of functions respectively corresponding to a plurality of states of the user, the electronic device, according to an embodiment, may adjust at least one of the plurality of states, based on connections between the nodes each corresponding to the body parts and the nodes each corresponding to a plurality of states, in the information obtained in the operation 310, so that independent body parts are used by the user in each of the plurality of states. Referring to the example of FIG. 3, the electronic device may execute another function corresponding to another state (e.g., the third state corresponding to the third function) distinct from the user's current state while maintaining the user's current state (e.g., the first state). The electronic device, according to an embodiment, may execute a function corresponding to a state having a relatively higher priority among the plurality of states, based on a priority assigned to each of the plurality of states. For example, when any one body part is commonly used in a plurality of states, the electronic device may execute a function associated with a state having a relatively higher priority among the plurality of states. The operation performed by the electronic device using the priority of each of the plurality of states, according to an embodiment, will be later described in more detail with reference to FIG. 12.

As seen from the foregoing, the electronic device, according to an embodiment, can identify one or more body parts related to the first state of the user, using the knowledge graph. In a state in which an event for executing the second function related to the second state distinct from the first state of the user occurs, the electronic device, according to an embodiment, may use the knowledge graph to determine whether the first body part corresponding to the first state and the second body part corresponding to the second state match each other. When the action in the first state and the action in the second state require the same body part, the electronic device may execute a third function corresponding to a third state distinct from the second state, independently of executing the second function corresponding to the second state.

Hereinafter, a configuration of a knowledge graph stored in an electronic device, according to an embodiment, is described in detail with reference to FIG. 4.

Figure 4:
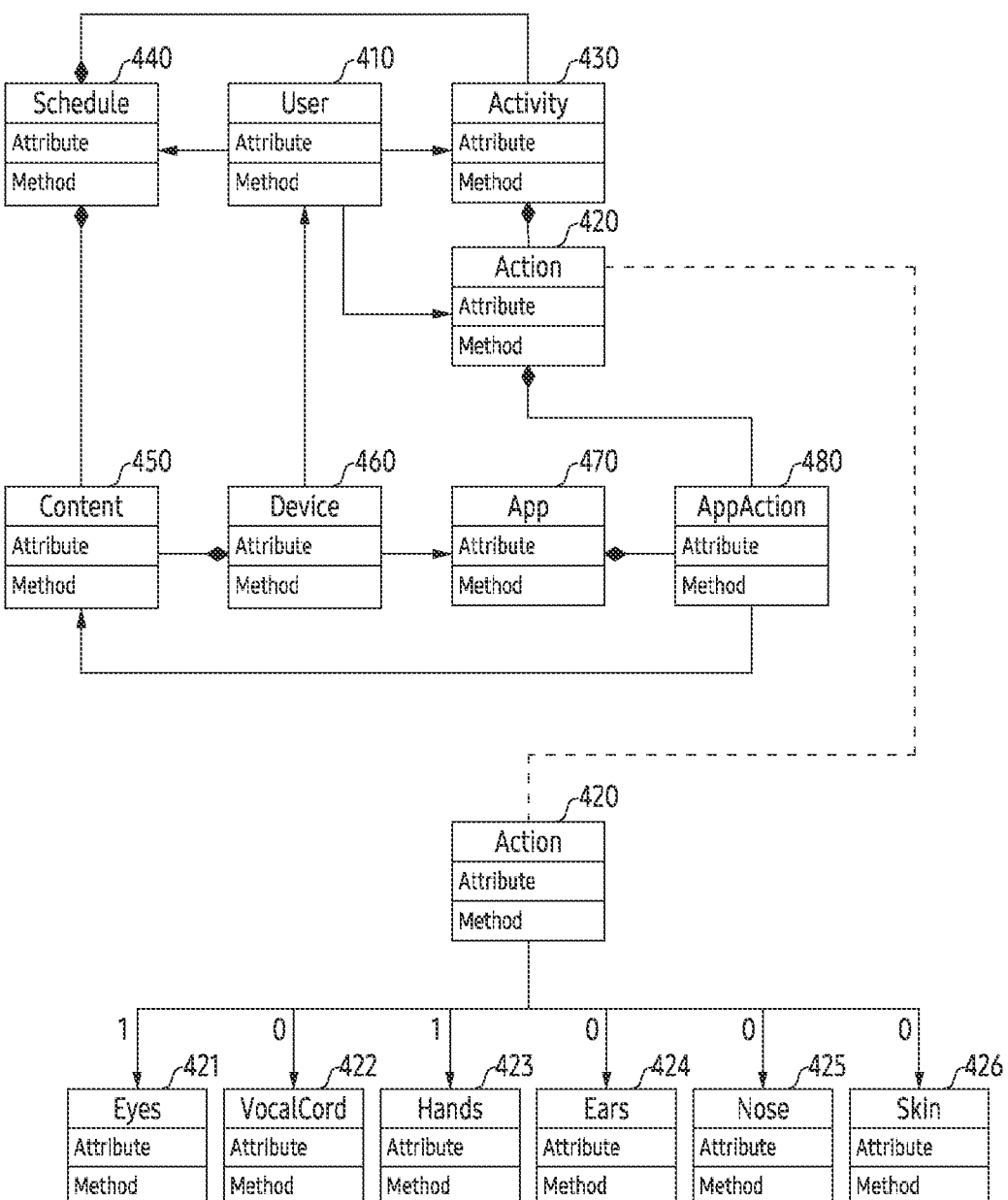
FIG. 4 is a diagram illustrating an example of a knowledge graph stored in an electronic device according to an embodiment.

FIG. 4 is a diagram illustrating an example of a knowledge graph stored in an electronic device, according to an embodiment. The electronic device of FIG. 4 may include the electronic devices 101-1, 101-2, 101-3 and 101-4 of FIG. 1 and the electronic device 101 of FIG. 2. The knowledge graph of FIG. 4 may include knowledge graphs 121, 121-1, 121-2, 122, 123 and 124 of FIG. 1) and/or the knowledge graph 120 of FIG. 2. The knowledge graph of FIG. 4 may correspond to, for example, the knowledge graph in the operation 310 of FIG. 3.

In an embodiment, the knowledge graph may include a plurality of nodes connected to each other based on an edge. The edge may represent relationship in the knowledge graph. Hereinafter, an edge may be referred to as a connection. Each of the nodes may correspond to a class and/or an instance of the knowledge graph. The knowledge graph may be individualized according to the user's state, as the electronic device storing the knowledge graph monitors the user's state.

Referring to FIG. 4, there is illustrated a plurality of nodes (410, 420, 421, 422, 423, 424, 425, 426, 430, 440, 450, 460, 470 and 480) included in the knowledge graph. Referring to FIG. 4, anode 410 may correspond to a class ('user') indicating a user. The node 410 may include, for example, attributes indicating information related to the user, such as, e.g., the user's ID, name, gender, age, etc. Referring to FIG. 4, a node 420 may correspond to a class indicating a user's state. The node 420 may include, for example, attributes indicating a designated name (such as e.g., GoingToBed, WakingUp, LeavingHome, ArrivingAtOffice) indicating an action associated with a corresponding state, and/or a body part associated with the state.

Referring to FIG. 4, a node 430 may correspond to a class to indicate a set of one or more states. The node 430 may indicate, for example, a set of one or more actions and/or states that are distinguished by a user's purpose and performed for a specified period of time and/or based on a specified order. Hereinafter, a set of one or more states indicated by the node 430, capable of being distinguished by a user's purpose, may be referred to as a sequence of activities and/or states.

Referring to FIG. 4, the node 430 may be connected to the node 420 having a class related to a state. When the node 430 is connected to a plurality of nodes (e.g., the node 420) having the class related to the state, the node 430 may include data indicating a sequence of the plurality of connected nodes. The node 430 may include a set of one or more states and/or a designated name (e.g., Sleeping, CommutingToWork) indicating a user's purpose associated with the set, as an attribute. An example in which the node 430 indicates a sequence of a plurality of states will be described later with further reference to FIGS. 9, 11, and/or 21.

Referring to FIG. 4, a node 440 may correspond to a class indicating a user's daily routine. The node 440 may be connected to one or more other nodes to structuralize a user's daily routine based on a timeline. The users daily routine structuralized based on the node 440 will be described later with reference to FIG. 20.

Referring to FIG. 4, a node 450 may correspond to a class indicating contents stored in the electronic device. The node 450 may include, for example, attributes indicating a type of content (e.g., message, calendar event, and/or media) corresponding to the node 450. Referring to FIG. 4, a node 460 may correspond to a class indicating the electronic device. The node 460 may include attributes indicating the type, vendor, and/or state of the electronic device. Referring to FIG. 4, a node 470 may correspond to a class indicating an application executable in the electronic device. The node 470 may include attributes indicating the type, path, and/or state of the application corresponding to the node 470. Referring to FIG. 4, a node 480 may correspond to a class indicating the function of the application executable in the electronic device. For example, the node 480 may include generalized attributes of the application functionality. Hereinafter, the abstraction and/or generalization of the attributes may imply identifying a group of multiple nodes having a common attribute, and/or creating a node indicating the group of the nodes, based on the common attribute in between the multiple nodes.

The electronic device, according to an embodiment, may generate a knowledge graph personalized for the user by connecting nodes to each other based on intensity. For example, in the knowledge graph, the state of establishing a call connection may be indicated based on connection of a node 410 corresponding to the user, a node 420 corresponding to a call connection state, a node 460 corresponding to an electronic device to which the call connection is made, a node 470 corresponding to an application (e.g., a calling application) related to the call connection, and a node 480 corresponding to a call connection function of the application. The intensity may indicate a degree of connection between nodes based on, for example, a Boolean data type and/or a floating-point data type.

The electronic device, according to an embodiment, may connect the nodes based on a triple format representing the subject, object, and predicate of a natural language in a format recognizable by the electronic device. For example, the electronic device may assign at least one of parameters indicating the intensity and a type of directional connection, to the directional connection between two nodes within the knowledge graph. The type may indicate to which one of a plurality of predicates the directional connection corresponds. When two nodes are connected to each other by a directional connection to which a type indicating a certain predicate is assigned, each of the two nodes may indicate a subject and an object corresponding to a predicate related to the type. For example, the directional connection may represent a natural language sentence having the predicate corresponding to the type assigned to the directional connection and having the two nodes connected by the directional connection as the subject and the object, respectively. When the directional connection has intensity, the intensity may indicate intensity of the natural language sentence indicated by the directional connection.

The electronic device, according to an embodiment, may use the nodes 421, 422, 423, 424, 425 and 426, each corresponding to the body parts of a designated user, to indicate one or more body parts used by the user's state in the knowledge graph. The electronic device may indicate a plurality of body parts using the nodes 421, 422, 423, 424, 425 and 426 in the knowledge graph, so that the user's body part and attributes of the body part can be indicated as data recognizable by the electronic device. Referring to FIG. 4, each of the nodes 421, 422, 423, 424, 425 and 426 may correspond to a class indicating each of different body parts of the user. For example, the node 421 may correspond to a class indicating an eye of the user's body parts. For example, the node 422 may correspond to a class indicating vocal cords of the user's body parts. For example, the node 423 may correspond to a class indicating a hand of the user's body parts. For example, the node 424 may correspond to a class indicating an ear of the user's body parts. For example, the node 425 may correspond to a class indicating a nose of the user's body parts. For example, the node 426 may correspond to a class indicating skin of the user's body parts.

The electronic device, according to an embodiment, may connect, based on the intensity, the node 420 corresponding to a certain state and each of the nodes 421, 422, 423, 424, 425 and 426 corresponding to each of the body parts to indicate one or more body parts used by the user in the state corresponding to the node 420. For example, the node 420 corresponding to a web surfing state may be connected, based on relatively higher intensity (e.g., level 1), with the node 421 corresponding to an eye and the node 423 corresponding to a hand of the body parts. The node 420 corresponding to the web surfing state may be either connected or not connected based on relatively lower intensity (e.g., level 0) with other nodes 422, 424, 425 and 426, being distinct from the nodes 421 and 423. In response to a user input executing the web browser application, the electronic device may identify that the current state of the user corresponds to the web surfing state. In the web surfing state, the electronic device may identify that eyes and hands are used by the user in surfing the web, based on the intensities between the node 420 corresponding to the web surfing state and the nodes 421, 422, 423, 424, 425 and 426 corresponding to each of the body parts in the knowledge graph.

As described above, the electronic device, according to an embodiment, may identify the state of the user, based on the knowledge graph in which a plurality of nodes 410, 420, 421, 422, 423, 424, 425, 426, 430, 440, 450, 460, 470 and 480 are connected with each other based on their intensities. The electronic device may identify a body part used by a user in any one of distinct states and a usage amount of the body part, using the knowledge graph. Based on the usage amount of the identified body part, the electronic device may execute a function for adjusting the usage amount of the body part.

Hereinafter, one or more processes executed in the electronic device in relation to the knowledge graph of FIG. 4 are described with reference to FIG. 5.

Figure 5:
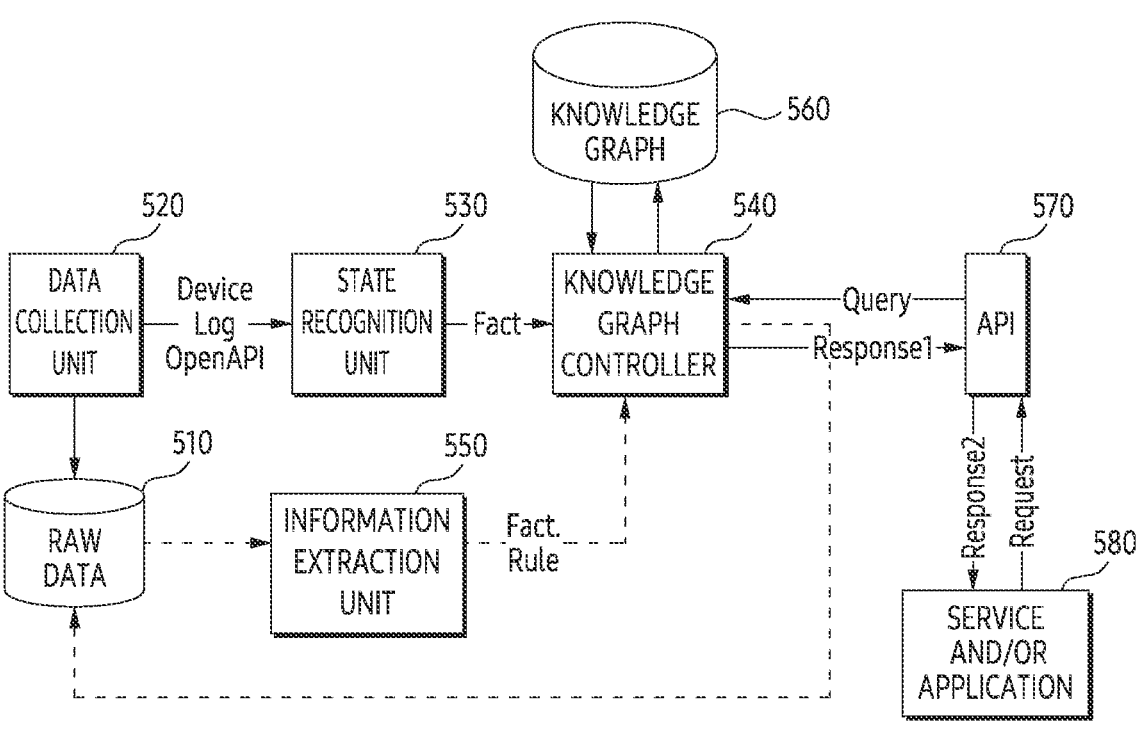
FIG. 5 is a diagram illustrating one or more processes executed in an electronic device and associated with a knowledge graph according to an embodiment.

FIG. 5 is a diagram for describing one or more processes executed in an electronic device, according to an embodiment, and having relation to a knowledge graph 560. The electronic device of FIG. 5 may include the electronic devices 101-1, 101-2, 101-3 and 101-4 of FIG. 1 and the electronic device 101 of FIG. 2. The process of FIG. 5 may be performed, for example, by the electronic device 101 and/or the processor 210 of FIG. 2. The knowledge graph 560 of FIG. 5 may include, for example, the knowledge graphs 121, 121-1, 121-2, 122, 123, 124 of FIG. 1 and/or the knowledge graph 120 of FIG. 2. Referring to FIG. 5, functions and/or sub-routines included in one or more processes executed in the electronic device, according to an embodiment, are shown separately according to information transferred between the functions and/or sub-routines.

The electronic device, according to an embodiment, may execute one or more processes shown in FIG. 5 and associated with the knowledge graph 560, based on one or more instructions stored in the memory (e.g., a memory 220 of FIG. 2). The processes may be executed in the second state, being distinct from the first state that is visible to the user, such as, for example, a background process and/or a daemon.

Referring to FIG. 5, the process that can be executed in the electronic device, according to an embodiment, may include a data collection unit 520 to access raw data 510. As described above, the raw data 510 may include log data in which conditions occurring inside the electronic device or in the vicinity of the electronic device detected by the electronic device are recorded. The electronic device, according to an embodiment, may identify a call of an application programming interface (API) related to the data collection unit 520. In response to identifying the call from the API, the electronic device may execute the data collection unit 520 to parse the raw data 510. The electronic device may generate information including a result of parsing the raw data 510, in response to the called API. The information may include, for example, log data of the electronic device.

Referring to FIG. 5, the process executable in the electronic device, according to an embodiment, may include a state recognition unit 530 to recognize a user's state, based on the raw data 510. The electronic device may execute the state recognition unit 530 to obtain, for example, the parsed log data from the raw data 510 by execution of the data collection unit 520. Based on the obtained log data, the electronic device may obtain information indicating a fact related to the user's state using the executed state recognition unit 530.

Referring to FIG. 5, the process executable in the electronic device, according to an embodiment, may include an information extracting unit 550 to extract information from the raw data 510. Referring to FIG. 5, the electronic device may execute the information extracting unit 550 to access the raw data 510. Referring to FIG. 5, the electronic device, according to an embodiment, may obtain information indicating a fact related to the user's state from the raw data 510, based on the state recognition unit 530 and/or the information extraction unit 550. Referring to FIG. 5, the electronic device, according to an embodiment, may obtain, based on the information extracting unit 550, information indicating a rule used for generating and/or searching of the knowledge graph, and relating to the user's state from the raw data 510.

Referring to FIG. 5, the process executable in the electronic device, according to an embodiment, may include a knowledge graph controller 540 for generating and/or updating of the knowledge graph 560, based on the information obtained from the state recognition unit 530 and/or the information extraction unit 550. Based on the knowledge graph controller 540, the electronic device may obtain, for example, the information indicating a fact related to the user's state obtained by the execution of the state recognition unit 530 and/or the information extraction unit 550. Using the information indicating the fact, the electronic device may change the intensity and/or the attributes between one or more nodes related to the fact in the knowledge graph 560. The electronic device may execute the knowledge graph controller 540 to obtain, for example, the information indicating the rule used for generating and/or searching of the knowledge graph 56i0 obtained by the information extraction unit 550. By using the information indicating the rule, the electronic device may change the intensity and/or the attributes between one or more nodes related to the rule in the knowledge graph 560.

Referring to FIG. 5, the process executable in an electronic device, according to an embodiment, may operate based on an API 570 for executing a function related to the knowledge graph 560. The electronic device may use the API 570 to convert a request of a service and/or an application 580 to access the knowledge graph 560, into a form of a query for executing the knowledge graph controller 540. The service and/or the application 580, corresponding to another process executable by the electronic device, may be a process for executing one or more functions based on the knowledge graph 560. The electronic device may execute the knowledge graph controller 540 based on the converted query to obtain a response corresponding to the query. In response to obtaining the response corresponding to the query, the electronic device may provide the obtained response to the service and/or the application 580 using the API 570. Hereinafter, the operation of searching or identifying the knowledge graph 560 may imply an operation that causes searching or identifying the knowledge graph 560 by the knowledge graph controller 540 using the API 570.

In an embodiment, the knowledge graph controller 540 may include a knowledge graph engine based on an algorithm for searching the knowledge graph 560 according to a query word. For example, the knowledge graph engine may include an incremental rule engine. In the knowledge graph engine where the incremental rule engine and a reasoning engine are integrated together, the electronic device may execute the knowledge graph controller 540 including the knowledge graph engine to provide materialization information based on the integrated incremental rule engine and inference engine at the construction time of the knowledge graph 560. For example, the knowledge graph engine may include a query time rule engine. Based on the knowledge graph engine including the query time rule engine, the electronic device may apply the rule at a query time of searching the knowledge graph 560 based on the query word to provide a response applied with a rule.

The electronic device, according to an embodiment, may change the knowledge graph 560, based on information (e.g., information indicating a function of an application executed by a user) based on the raw data 510, while the process related to the knowledge graph controller 540 is being executed by the electronic device. The electronic device, according to an embodiment, may use the information extraction unit 550 to identify a state pattern of the user and/or a usage pattern of the electronic device by the user from the raw data 510, while the process related to the knowledge graph controller 540 is being executed by the electronic device. Based on the identified user's state pattern and/or the user's usage pattern of the electronic device, the electronic device may change the knowledge graph 560 based on the knowledge graph controller 540.

As described above, the electronic device, according to an embodiment, may execute one or more processes to generate information related to the user's state (e.g., a knowledge graph 560). The one or more processes may correspond to a background process that does not interfere with the user's state.

Hereinafter, an operation performed by the electronic device, according to an embodiment, based on one or more processes related to the knowledge graph 560 are described with reference to FIG. 6.

Figure 6:
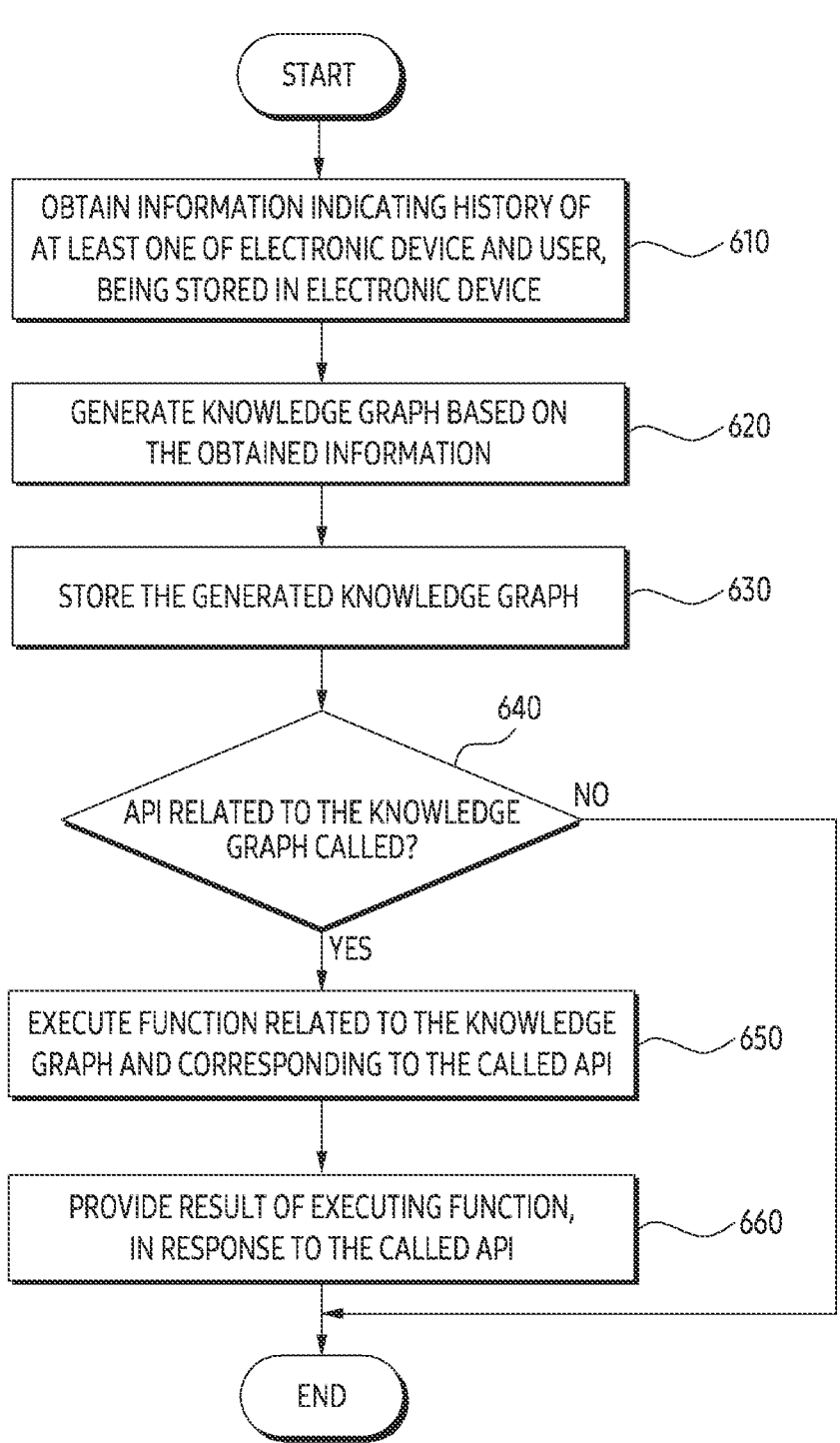
FIG. 6 is a flowchart illustrating an operation performed by an electronic device based on a knowledge graph according to an embodiment.

FIG. 6 is a flowchart illustrating an operation performed by an electronic device based on a knowledge graph, according to an embodiment. The electronic device of FIG. 6 may include the electronic devices 101-1, 101-2, 101-3 and 101-4 of FIG. 1 and/or the electronic device 101 of FIG. 2. The operation of the electronic device of FIG. 6 may be performed, for example, by the electronic device 101 and/or the processor 210 of FIG. 2. At least one of the operations in FIG. 6 may correspond to or be performed similarly to at least one of the operations of FIG. 3 (e.g., operation 310).

Referring to FIG. 6, in operation 610, the electronic device, according to an embodiment, may obtain information indicating a history of at least one of the electronic device and the user, being stored in the electronic device. The electronic device, according to an embodiment, may obtain, from the memory (e.g., a memory 220 of FIG. 2), at least one of log data of the electronic device, schedule data indicating the user's schedule, or list data including a list of contents stored in the memory. The electronic device, according to an embodiment, may obtain, for example, the raw data 510 of FIG. 5.

Referring to FIG. 6, in operation 620, the electronic device, according to an embodiment, may generate a knowledge graph based on the obtained information. For example, the electronic device may change the attributes of nodes included in the knowledge graph (e.g., the knowledge graph 120 of FIG. 2 and/or the knowledge graph 560 of FIG. 5) and/or change the intensity between the nodes, based on the obtained information. The electronic device may generate the knowledge graph, for example, by connecting nodes corresponding to any one of a plurality of designated classes to each other based on the intensity, as shown in FIG. 4. The electronic device may connect a node corresponding to the user's state identified by the obtained information and nodes corresponding to each of the user's body parts to each other in the knowledge graph, so as to indicate the body part used by the user in the state. An example in which a node corresponding to the user's state and nodes corresponding to each of the user's body parts are connected to each other in the knowledge graph will be described later with further reference to FIG. 7.

Referring to FIG. 6, in operation 630, the electronic device, according to an embodiment, may store the generated knowledge graph. The electronic device, according to an embodiment, may store the knowledge graph generated based on operation 620 in a memory included in the electronic device. The electronic device, according to an embodiment, may transmit a signal requesting storing of the knowledge graph along with the knowledge graph generated based on the operation 620, to an external electronic device (e.g., an electronic device 101-1 of FIG. 1) distinct from the electronic device. In an embodiment, the operation of the electronic device storing the knowledge graph may include an operation of storing information based on the format of OWL in a memory.

Referring to FIG. 6, in operation 640, the electronic device, according to an embodiment, may determine whether an API related to the knowledge graph has been called. The API related to the knowledge graph may be called, for example, in response to performing an operation for accessing the knowledge graph, such as the operations 310 and 320 of FIG. 3. When the API related to the knowledge graph is called ('YES' in operation 640), the electronic device, according to an embodiment, may execute a function related to the knowledge graph and corresponding to the called API, in operation 650. The electronic device, according to an embodiment, may execute the function corresponding to the called API, using the knowledge graph controller 540 of FIG. 5.

Referring to FIG. 6, in operation 660, the electronic device, according to an embodiment, may provide a result of executing the function in response to the called API. The result of executing the function may be provided to a subject (e.g., a service and/or application 580 of FIG. 5) that called the API in the operation 640. For example, the electronic device may store the result of executing the function in part of the memory used by the application that called the API, and in turn, provide the result to the application. For example, when an external electronic device distinct from the electronic device calls an API, the electronic device may transmit the result of executing the function to the external electronic device.

Hereinafter, an operation in which an electronic device, according to an embodiment, connects nodes respectively corresponding to each of distinct states and different body parts in a knowledge graph will be described with reference to FIG. 7.

Figure 7:
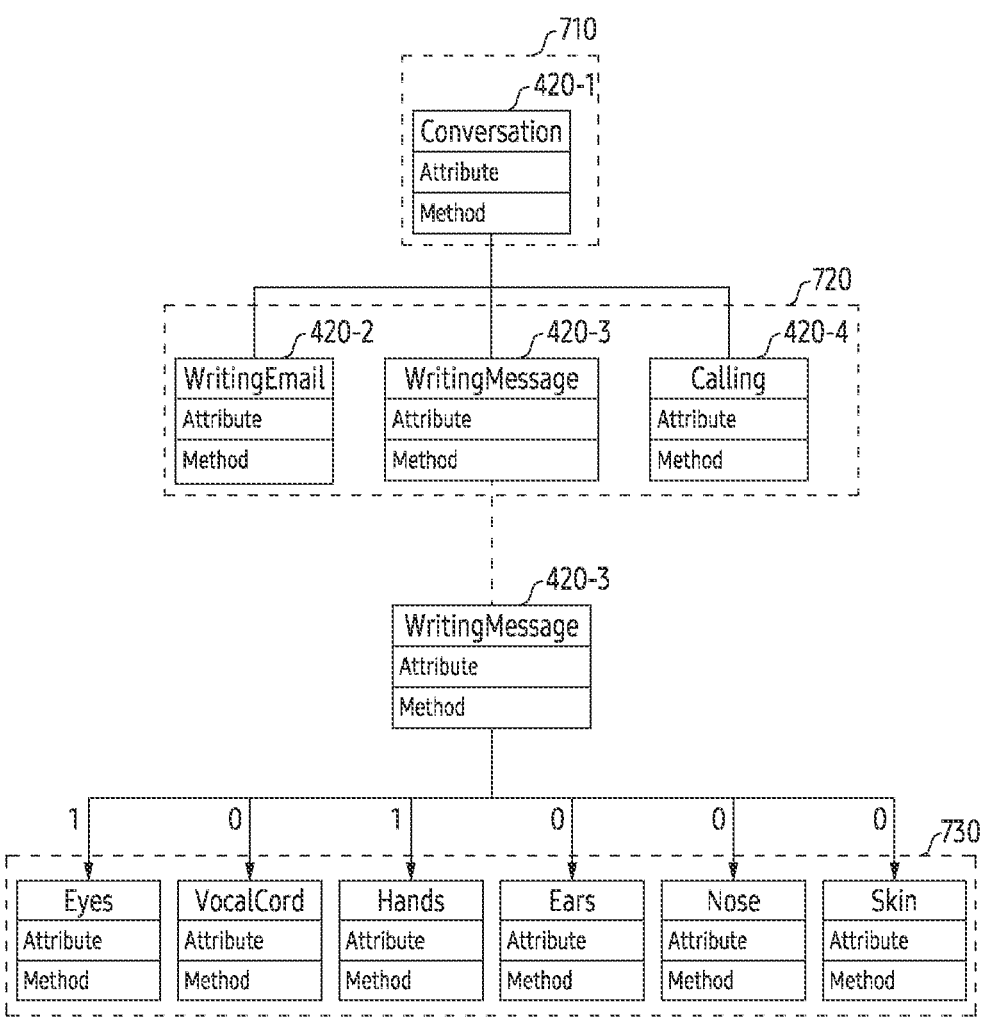
FIG. 7 is a diagram illustrating an example of a knowledge graph stored in an electronic device according to an embodiment.

FIG. 7 is a diagram illustrating an example of a knowledge graph stored in an electronic device according to an embodiment. The electronic device of FIG. 7 may include the electronic devices 101-1, 101-2, 101-3 and 101-4 of FIG. 1 and the electronic device 101 of FIG. 2. The knowledge graph of FIG. 7 may include knowledge graphs 121, 121-1, 121-2, 122, 123 and 124 of FIG. 1 stored in each of the electronic devices 101-1, 101-2, 101-3 and 101-4 of FIG. 1, the knowledge graph 120 of FIG. 2, and/or the knowledge graph 560 of FIG. 5. The knowledge graph of FIG. 7 may, for example, correspond to the knowledge graph of FIGS. 3 and/or 6.

Referring to FIG. 7, part of a knowledge graph stored in an electronic device, according to an embodiment, is illustrated. Referring to FIG. 7, nodes 420-1, 420-2, 420-3 and 420-4 each corresponding to classes indicating distinct states in the knowledge graph are shown. For example, the knowledge graph may include a node 420-2 associated with a state in which a user writes an e-mail, a node 420-3 associated with a state in which a user writes a text message, and a node 420-4 associated with a state in which a user performs a voice call.

The electronic device, according to an embodiment, may use a hierarchical connection based on similarity between the nodes 420-2, 420-3 and 420-4 to group similar states into one layer in the knowledge graph. Referring to FIG. 7, based on the commonality that the nodes 420-2, 420-3 and 420-4 are in a state associated with a conversation, the electronic device may generate a node 420-1 that abstracts the states of the nodes 420-2, 420-3 and 420-4 in the knowledge graph. The electronic device, according to an embodiment, may set a layer 720 corresponding to the nodes 420-2, 420-3 and 420-4 that are similar to each other in the knowledge graph. Based on the nodes 420-2, 420-3 and 420-4 included in the layer 720, the electronic device may set a layer 710 that is higher than the layer 720. The electronic device, according to an embodiment, may create the node 420-1 that abstracts the states of the nodes 420-2, 420-3 and 420-4 in the layer 710. The node 420-1 may be included in the layer 710 that is a higher layer of the layer 720 in the knowledge graph, and may be connected with the nodes 420-2, 420-3 and 420-4 included in the layer 720. For example, each of the nodes 420-2, 420-3 and 420-4 may be connected to each other via the node 420-1.

The electronic device, according to an embodiment, may identify another state replacing a state in a laver set in the knowledge graph. Referring to FIG. 7, the nodes 420-2, 420-3 and 420-4 existing in the layer 720 may correspond to distinct states related to a conversation, respectively. For example, the nodes 420-2, 420-3 and 420-4 existing in the layer 720 may indicate interchangeable states. Each of the nodes 420-2, 420-3 and 420-4 indicating interchangeable states may include an attribute indicating a priority between those nodes 420-2, 420-3 and 420-4. An operation performed by the electronic device based on the attribute indicating the priority and included in each of the nodes 420-2, 420-3 and 420-4, will be described later with further reference to FIG. 12. The electronic device, according to an embodiment, may identify a second state capable of replacing the first state, from among one or more nodes included in a layer corresponding to the first state of layers of the knowledge graph. Hereinafter, a sibling state of a specific state may mean a state corresponding to another node included in the same layer as a node corresponding to the specific state in the knowledge graph. For example, each of the sibling states may indicate different actions that are interchangeable and provide a similar result to the user.

Referring to FIG. 7, nodes 730 corresponding to each of the users body parts are shown. Each of the nodes 730 may correspond to a different body part of the user. Each of the nodes 420-1, 420-2, 420-3 and 420-4 corresponding to a state may be connected to at least one of the nodes 730 based on intensity. The intensity may be a parameter indicating the intensity of edge and/or the relationship between nodes, and may have the format of a Boolean data type and/or a floating-point data type format.

Referring to FIG. 7, an example of the intensity assigned to the edge connecting between the node 420-3 related to the state of writing a text message and the nodes 730 each corresponding to the body parts is illustrated. The electronic device, according to an embodiment, may assign and/or identify an intensity indicating whether the use's body part is exclusively used by a state, in the knowledge graph.

For example, while writing a text message, the users eyes may be exclusively used to write the text message. For example, if the user performs another state related to the user's eyes while writing the text message, it may cause the writing of the text message to be interrupted by performing the other state. The electronic device, according to an embodiment, may assign a predetermined intensity (e.g., level 1) indicating that the body part is exclusively used for the state to the intensity between the node 420-3 and the node related to the eyes among the nodes 730.

For example, while writing a text message, the users vocal cords may be used independently of the text message. For example, the user may chat with another user without ceasing to write a text message. The electronic device, according to an embodiment, may assign a predetermined intensity (e.g., level 0) indicating that a body part is available independently of the state to the intensity between the node 420-3 and the node related to the vocal cords among the nodes 730. Hereinafter, a fact that nodes are not connected to each other may mean that the intensity between the nodes corresponds to a predetermined intensity indicating a blockage between nodes, such as a value of 0. The electronic device, according to an embodiment, may indicate whether a body part is exclusively used in a state, using a truth value of 0 (or 'false') or 1 (or 'true'). The truth value may be stored in the electronic device based on a predetermined type such as, e.g., a Boolean type. Referring to FIG. 7, each of the nodes 730 may be connected to the node 420-3 with a separate intensity, based on the characteristics of an operation in which the user writes a text message.

The electronic device, according to an embodiment, may identify the exclusively used body parts, such as eyes and vocal cords, and the partially used body parts, such as ears. For example, the user may simultaneously listen to music and/or voice of a calling party over a phone call, through his/her ears. While simultaneously performing both a state of listening to music and another state of talking over the phone call, the user's ear may be at least partially used for each of the states. The electronic device, according to an embodiment, may connect a node corresponding to a partially usable body part, like the ear, with a node corresponding to a specific state, based on the intensity indicating a degree of being partially used by the specific state.

The electronic device, according to an embodiment, may indicate the usage of body parts by states, as a rational number between 0 and 1, using intensity based on a floating-point data type. For example, the node 420-4 related to the state of performing a voice call may be connected with a node related to the ear among the nodes 730 based on the intensity between 0 and 1, since the user can listen to other sounds distinct from the voice on the phone call, using his/her ears, while performing the voice call. The electronic device, according to an embodiment, may cause a change in the intensity by changing the mode of the electronic device. In an example that the user performs a voice call, the electronic device may adjust the volume of the speaker (e.g., a speaker 260 of FIG. 2) to adjust the intensity between the node corresponding to the state related to the voice call and the node corresponding to the ear. An operation in which the electronic device, according to an embodiment, adjusts the intensity between nodes based on a change in mode will be described later with further reference to FIGS. 12 to 17.

As described above, in the knowledge graph, a plurality of states may be grouped based on a plurality of layers. As a plurality of states is grouped in the knowledge graph, the electronic device, according to an embodiment, may more quickly search for a state similar to a specific state in the knowledge graph. As described above, in the knowledge graph, a state and a body part may be connected with each other, based on intensity. The format of the intensity may be determined based on the characteristics of the body part. The electronic device, according to an embodiment, may identify one or more body parts used by the user of the current state, based on the intensity assigned between a node corresponding to the user's current state and nodes corresponding to each of body parts, in the knowledge graph. Based on the identified one or more body parts, the electronic device may selectively execute a function related to usage of one or more body parts used by the user in the current state.

Hereinafter, an operation of the electronic device searching for a part of the knowledge graph related to the user's current state will be described in more detail with reference to FIG. 8. The electronic device, according to an embodiment, may search for a part of the knowledge graph to predict another state subsequent to the user's current state.

Figure 8:
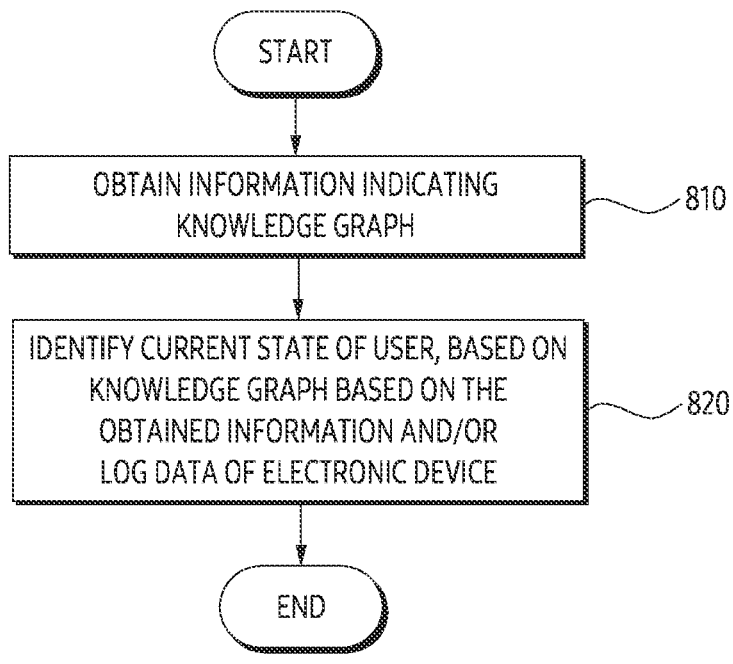
FIG. 8 is a flowchart illustrating an operation in which an electronic device obtains data related to a user's state from a knowledge graph according to an embodiment.

FIG. 8 is a flowchart illustrating an operation in which an electronic device obtains data related to a user's state from a knowledge graph, according to an embodiment. The electronic device of FIG. 8 may include the electronic devices 101-1, 101-2, 101-3 and 101-4 of FIG. 1 and/or the electronic device 101 of FIG. 2. The operation of the electronic device of FIG. 8 may be performed, for example, by the electronic device 101 and/or the processor 210 of FIG. 2. At least one of the operations of FIG. 8 may correspond to or be performed similarly to at least one (e.g., the operation 310, 320 or 330) of the operations of FIG. 3. The knowledge graph of FIG. 8 may include the knowledge graphs 121, 121-1, 121-2, 122, 123 and 124 of FIG. 1 and the knowledge graph 120 of FIG. 2.

Referring to FIG. 8, in operation 810, the electronic device, according to an embodiment, may obtain information indicating a knowledge graph. The electronic device, according to an embodiment, may obtain, from the memory (e.g., a memory 220 of FIG. 2), the knowledge graph in which a plurality of states are connected to each other based on a hierarchy related to a similarity between the plurality of states, and indicating a usage of a body part by the user in each of the plurality of states. The information identified by the electronic device may correspond to information indicating the knowledge graph based on, for example, OWL, RDF, and/or SWRL.

Referring to FIG. 8, in operation 820, the electronic device, according to an embodiment, may identify a current state of the user, based on the knowledge graph based on the obtained information and/or log data of the electronic device. The electronic device, according to an embodiment, may identify a node corresponding to the user's current state in the knowledge graph representing the user's action based on a connection of nodes. For example, a plurality of nodes included in the knowledge graph may be connected to each other, based on a history of switching to distinct states by the user. For example, the plurality of nodes connected to each other may be connected to each other based on a timeline. The electronic device, according to an embodiment, may identify a state corresponding to a node corresponding to the current time among the plurality of nodes connected to each other based on the timeline in the knowledge graph, as the user's current state.

The electronic device, according to an embodiment, may identify the user's current state, based on data including a history of using the electronic device by the user, such as, e.g., log data. For example, the electronic device may identify the current state of the user, based on an application in the electronic device that is being currently executed by the user. For example, the electronic device may identify the current state of the user, based on the user's biometric information detected by the sensor.

As described above, the electronic device, according to an embodiment, may identify the user's state (e.g., the current state), based on the connection of nodes corresponding to each of the states in the knowledge graph. Based on the identified state, the electronic device, according to an embodiment, may identify and/or execute a function related to a body part independent of the body part related to the user's current state. The electronic device, according to an embodiment, may predict a state subsequent to the current state of the user, using the knowledge graph.

Hereinafter, an operation of the electronic device predicting a user's state by using the knowledge graph according to an embodiment is described in detail with further reference to FIG. 9.

Figure 9:
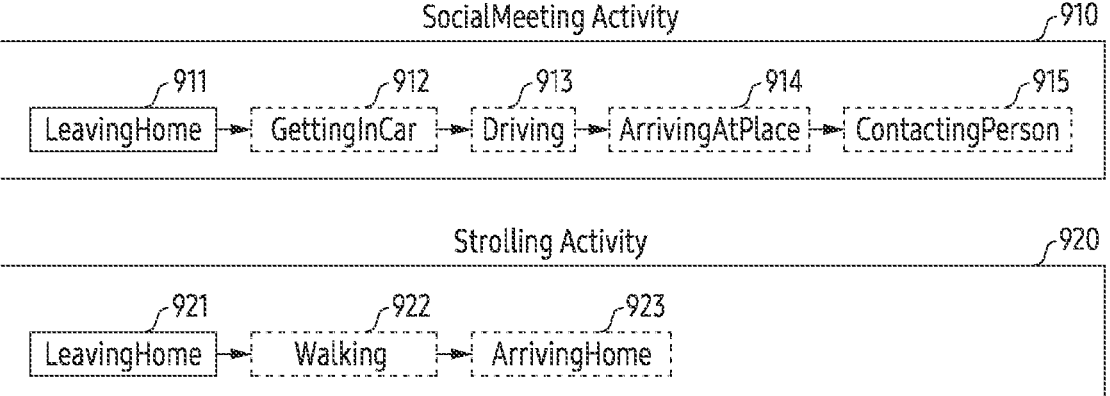
FIG. 9 is a diagram illustrating an example in which an electronic device identifies a next state of a user's current state according to an embodiment.

FIG. 9 shows a diagram for describing an example in which an electronic device identifies a next state subsequent to a user's current state, according to an embodiment. The electronic device of FIG. 9 may include the electronic devices 101-1, 101-2, 101-3 and 101-4 of FIG. 1 and the electronic device 101 of FIG. 2. The operation of the electronic device of FIG. 9 may correspond to at least one of the operations of FIGS. 3, 6, and/or 8.

Referring to FIG. 9, part of a node included in a knowledge graph obtained by an electronic device is illustrated. The knowledge graph includes knowledge graphs 121, 121-1, 121-2, 122, 123 and 124 of FIG. 1 stored in each of the electronic devices 101-1, 101-2, 101-3 and 101-4 of FIG. 1, the knowledge graph 120 of FIG. 2 and/or the knowledge graph 560 of FIG. 5.

The electronic device, according to an embodiment, may identify, based on at least one of the operations 310 and 320 of FIG. 3 and/or the operations 810 and 820 of FIG. 8, in the knowledge graph, a node corresponding to the current state of the user. For example, the electronic device may identify a node having an attribute corresponding to spatial location of the user and a state corresponding to the node, by comparing the attributes of nodes each corresponding to a spatial location of the user and the attributes of nodes each corresponding to different states in the knowledge graph, where the spatial location of the user may be identified using a GPS sensor, a gyro sensor, an acceleration sensor, and/or a gravity sensor. Hereinafter, it is assumed that the electronic device identifies a change in the spatial location of the user based on a virtual boundary line generated based on spatial location such as, e.g., a geo-fence, thereby identifying that the user is currently in a going-out state.

Referring to FIG. 9, in response to identifying that the user's current state is a going-out state, the electronic device may identify one or more nodes 911 and 921 related to the user's current going-out state in the knowledge graph. Referring to FIG. 9, in response to identifying the one or more nodes 911 and 921 corresponding to states related to the going-out state, the electronic device may identify groups or sets 910 and 920 of distinct states distinguished by a plurality of nodes each connected to the nodes 911 and 921. The sets of states 910 and 920 may include one or more states respectively corresponding to one or more actions performed by a user with intention, over a specified period, and/or based on a specified order. Although each of the sets of the states 910 and 920 is shown as a group of nodes 911, 912, 913, 914, and 915, and another group of nodes 921, 922, and 923, a node corresponding to each of the sets of states 910 and 920 may be stored in the knowledge graph, as in the node 430 in FIG. 4.

In one embodiment, each of the sets of states 910, 920 may be referenced to as an activity and/or a state sequence that is distinguished by the purpose of the user. Referring now to FIG. 9, the set of states 910 may include a plurality of states each corresponding to actions that the user sequentially performs to achieve the purpose of attending a meeting. For example, the set of states 910 may be connected in sequence as a node 911 corresponding to a going-out state, a node 912 corresponding to a state of boarding a vehicle, a node 913 corresponding to a driving state, a node 914 corresponding to arriving at a destination, and a node 915 corresponding to a state of meeting with another person. Referring to FIG. 9, the set of states 920 may include a plurality of states each corresponding to actions that the user may sequentially perform as part of a strolling activity. For example, in the set of states 920 may be connected in order to a node 921 corresponding to a going-out state, a node 922 corresponding to a strolling state, and a node 923 corresponding to arriving home. The nodes 921, 922, and 923 may include attributes and/or edges indicating the order of the nodes 921, 922, and 923. The sets of states 910 and 920 may be generated according to individualization of the knowledge graph by the electronic device, according to an embodiment, performing at least one of the methods in FIG. 6.

Referring to FIG. 9, in response to identifying one or more nodes 911 and 921 corresponding to the user's current state, the electronic device, according to an embodiment, may predict a next state to be performed following the user's current state, based on the sets of states 910 and 920 corresponding to each of the nodes 911 and 921. The electronic device, according to an embodiment, may identify the next state in each of the sets of states 910 and 920, based on a node connected subsequent to the nodes 911 and 921. For example, in the set of states 910, the electronic device may identify a node 912 corresponding to a state of getting in a vehicle, as a state to be performed subsequent to the node 911. For example, in the set of states 920, the electronic device may identify a node 922 corresponding to a state of walking, as a state to be performed subsequent to the node 921. Since the nodes 911 and 921 corresponding to the current state exist in the sets 910 and 920 of distinct states, the electronic device, according to an embodiment, may select a node corresponding to a next state among the nodes 912 and 922 each connected respectively to the nodes 911 and 921, based on the purpose of the user.

The electronic device, according to an embodiment, may infer the user's purpose among purposes corresponding to each of the sets of states 910 and 920, based on the confidence and/or the rule of each of the sets of states 910 and 920. The confidence, that is an attribute inferred from log data of the electronic device, such as the raw data 510 of FIG. 5, may indicate whether the user's state has a purpose corresponding to either one of the sets of states 910 and 920. For example, in response to identifying, from schedule information included in the raw data, that a schedule related to a meeting exists, the electronic device, according to an embodiment, may determine that the user's purpose corresponds to the set of states 910 associated with the purpose of attending the meeting, among the sets of states 910 and 920. In such a case, the electronic device may predict the next state subsequent to the user's current state, based on one or more states indicated by the set 910. For example, based on the node 912 included in the set of states 910 and connected to the node 911 corresponding to the user's current state, the electronic device, according to an embodiment, may predict that the user is going to ride on a vehicle.

As is apparent from the foregoing, the electronic device, according to an embodiment, can identify the current state of the user and the next state subsequent to the current state, based on the sets of states 910 and 920 generated by connecting nodes each corresponding to states that are sequentially switched by the user in the knowledge graph. The electronic device may selectively execute at least one of a plurality of functions that can be provided to the user, based on the identified current state and next state of the user.

Hereinafter, an operation in which an electronic device, according to an embodiment, selectively executes at least one of the plurality of functions that can be provided to the user, based on the current state and the next state of the user, is described in detail with further reference to FIG. 10.

Figure 10:
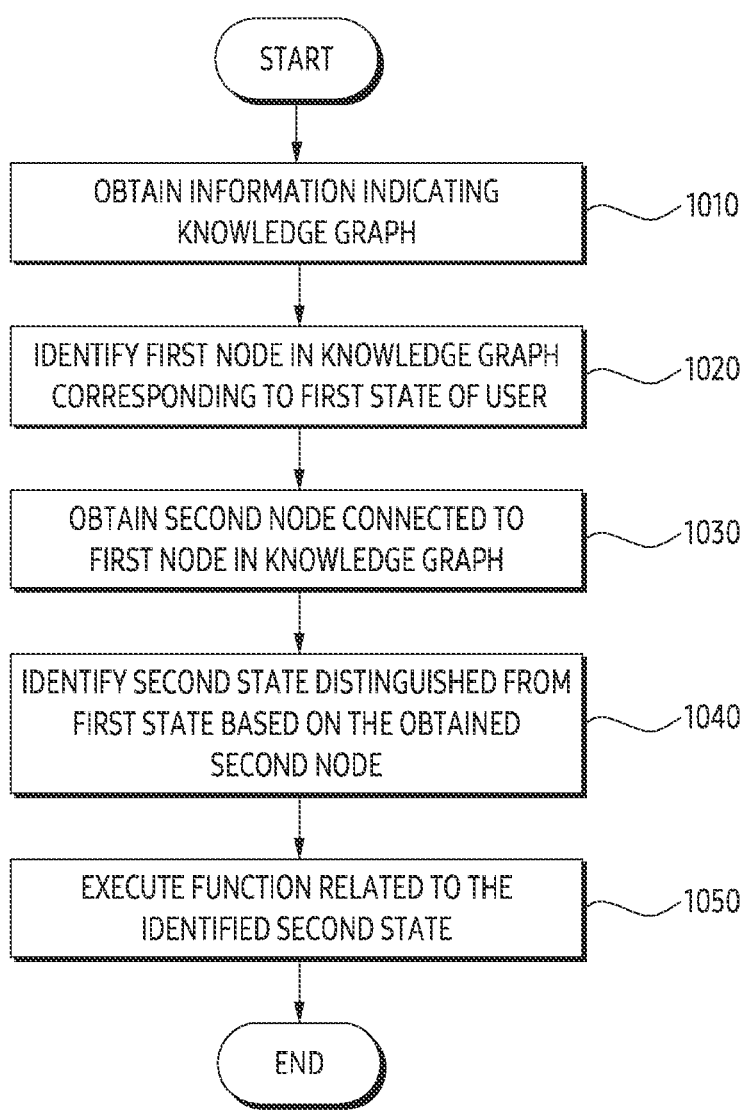
FIG. 10 is a flowchart illustrating an operation of an electronic device identifying a user's state, based on a plurality of nodes connected to each other in a knowledge graph, according to an embodiment.

FIG. 10 is a flowchart illustrating an operation in which an electronic device identifies a user's state, based on a plurality of nodes connected to each other in a knowledge graph, according to an embodiment. The electronic device of FIG. 10 may include the electronic devices 101-1, 101-2, 101-3 and 101-4 of FIG. 1 and/or the electronic device 101 of FIG. 2. The operation of the electronic device of FIG. 10 may be performed, for example, by the electronic device 101 and/or the processor 210 of FIG. 2. At least one of the operations of FIG. 10 may correspond to at least one of the operations of FIGS. 3, 6, and/or 8. The knowledge graph of FIG. 10 may include the knowledge graphs 121, 121-1, 121-2, 122, 123 and 124 of FIG. 1 and the knowledge graph 120 of FIG. 2.

Referring to FIG. 10, in operation 1010, the electronic device, according to an embodiment, may obtain information indicating a knowledge graph. The electronic device may obtain information indicating connection between distinct states of the user in the knowledge graph. For example, the information obtained by the electronic device may be indicated by a plurality of nodes connected to each other based on a user's state pattern included in raw data (e.g., raw data 510 in FIG. 5) in the knowledge graph. For example, as described above in FIG. 9, different nodes (e.g., nodes 911, 912, 913, 914, and 915 in FIG. 9) may form sequential connections indicating the user's state pattern in the knowledge graph. Nodes corresponding to each of the plurality of states may be connected to each other, based on one node corresponding to a class indicating a set of one or more states (e.g., a node corresponding to the node 430 in FIG. 4 or any one of the sets of states 910 and 920 in FIG. 9).

Referring to FIG. 10, in operation 1020, the electronic device, according to an embodiment, may identify a first node of nodes in the knowledge graph corresponding to a first state of a user. The electronic device may identify the first node corresponding to the first state of the user, for example, by performing at least one of the operations of FIG. 8. The first node in the knowledge graph identified by the electronic device may be, for example, a node generated based on a class indicating a user's state, such as the node 420 of FIG. 4. The first node in the knowledge graph may be connected to other nodes based on a class distinct from the class of the first node and/or entire nodes included in the same class as the class of the first node.

Referring to FIG. 10, in operation 1030, the electronic device, according to an embodiment, may obtain a second node connected to the first node in the knowledge graph. For example, the electronic device may obtain one or more other nodes connected to the first node in the knowledge graph. For example, the electronic device may identify a sequential connection between the first node and other nodes. From the identified sequential connection, the electronic device may extract one or more other nodes connected to the first node. For example, from the sequential connection between the first node and other nodes, the electronic device may obtain a second node directly connected to the first node.

Among one or more other nodes connected to the first node, the class of the second node identified by the electronic device, according to an embodiment, may correspond to the class of the first node (e.g., the class indicating the user's state like the node 420 in FIG. 4). For example, from nodes connected based on a class for indicating a set of one or more states, such as the node 430 of FIG. 4, the electronic device may obtain the second node connected to the first node. The second node obtained by the electronic device, according to an embodiment, may be directly and/or indirectly connected to the first node in the knowledge graph. The second node obtained by the electronic device, according to an embodiment, being any one of a plurality of nodes that form a sequential connection with the first node, may be any one of a plurality of nodes indicating a sequence of states each corresponding to the actions sequentially performed by the user.

Referring to FIG. 10, in operation 1040, the electronic device, according to an embodiment, may identify a second state distinguished from the first state based on the obtained second node. The second state may be a state indicated by the second node based on a class corresponding to the user's state. The electronic device, according to an embodiment, may identify the second state subsequent to the first state of the user, based on connection between the first node and the second node obtained based on the operation 1030. The electronic device, according to an embodiment, may identify the second state subsequent to the first state of the user while the current state of the user corresponds to the first state.

Referring to FIG. 10, in operation 1050, the electronic device, according to an embodiment, may execute a function related to the identified second state. For example, the electronic device may execute the function related to the second state identified in the operation 1040, among a plurality of functions that can be provided to the user. For example, while the current state of the user corresponds to the first state, the electronic device may execute the function related to the second state. The electronic device, according to an embodiment, may execute the function related to the second state, in response to predicting the second state subsequent to the first state, while the user's current state corresponds to the first state. The function related to the second state executed by the electronic device may include a function provided by a service provider and/or an application using the knowledge graph. The electronic device, according to an embodiment, may display a user interface (UI) to recommend the user to execute a function related to the second state. In response to receiving the user's response to the UI, the electronic device may execute the function related to the second state. In response to executing the function related to the second state, the electronic device may determine that the user's current state has been changed from the first state to the second state.

As described above, the electronic device, according to an embodiment, may identify, from the user's current state corresponding to the first state, the second state expected to be switched by the user following the first state. In response to identifying the second state, the electronic device, according to an embodiment, may execute the function related to the second state and/or recommend the user to execute the function. In response to expecting such a switching in between the first state and the second state by the user, the electronic device, according to an embodiment, may make a positive suggestion of the function related to the second state to the user in the first state.

Hereinafter, an operation in which an electronic device, according to an embodiment, performs an active recommendation to a user using a knowledge graph is described in detail with reference to FIG. 11.

Figure 11:
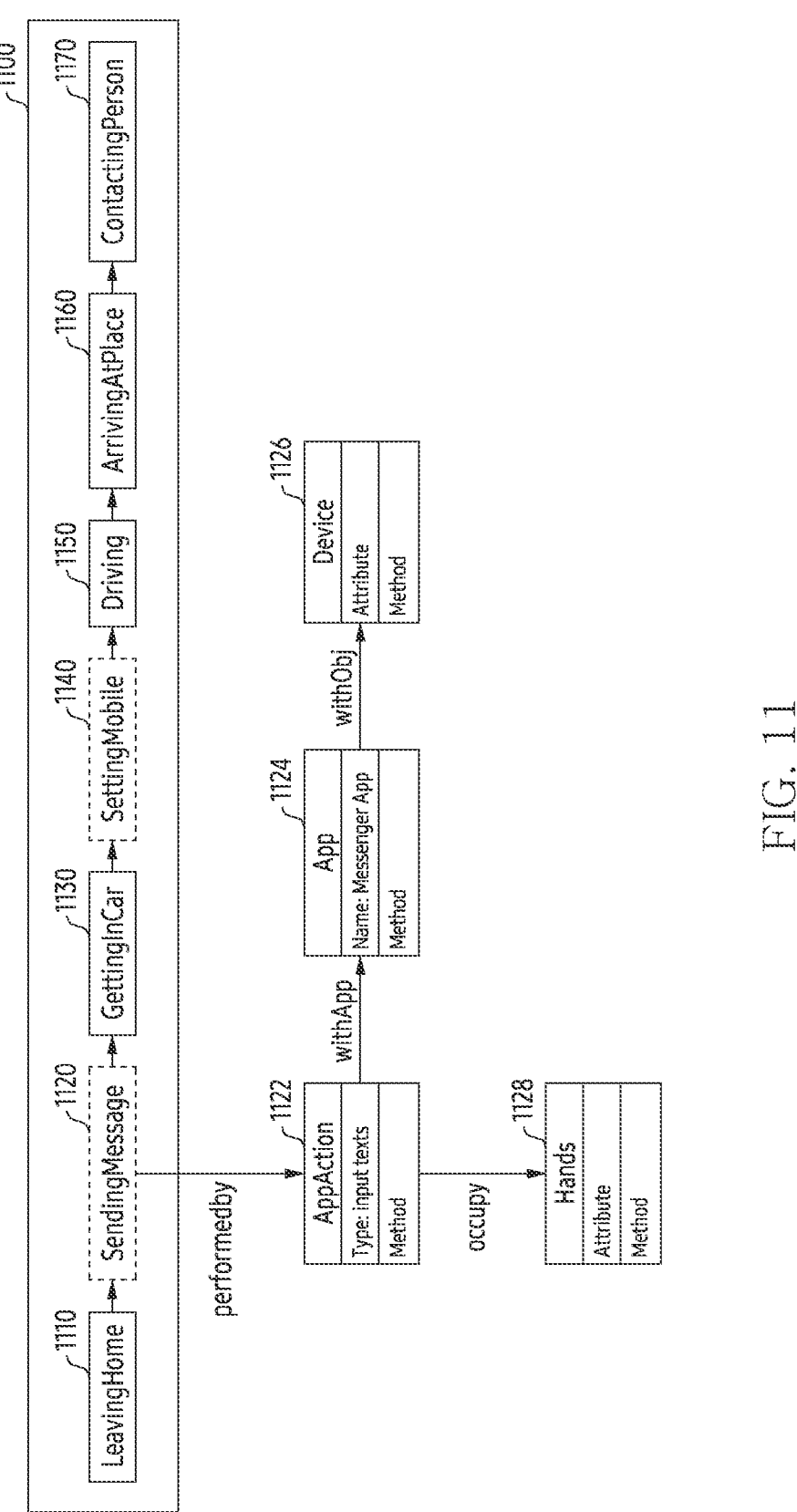
FIG. 11 is a diagram illustrating an example in which an electronic device executes a function related to a user's state, based on an application being executed in the electronic device, according to an embodiment.

FIG. 11 is a diagram for describing an example in which an electronic device, according to an embodiment, executes a function related to a user's state, based on an application being executed in the electronic device. The electronic device of FIG. 11 may include the electronic devices 101-1, 101-2, 101-3 and 101-4 of FIG. 1 and/or the electronic device 101 of FIG. 2. The electronic device of FIG. 11 may, for example, perform at least one of the operations of FIG. 10.

Referring to FIG. 11, some of nodes included in the knowledge graph obtained by the electronic device, according to an embodiment, are illustrated. The knowledge graph may include the knowledge graphs 121, 121-1, 121-2, 122, 123 and 124 of FIG. 1 and the knowledge graph 120 of FIG. 2. A portion of the knowledge graph shown in FIG. 11 may correspond to a portion of the knowledge graph shown in FIG. 9.

The electronic device, according to an embodiment, may identify a node corresponding to a user's current state in the knowledge graph. For example, the electronic device may identify that the current state of the user corresponds to a going-out state, based on a spatial location of the user identified using a GPS sensor. In response to identifying that the user's current state corresponds to the going-out state, the electronic device, according to an embodiment, may identify the node 1110 corresponding to the going-out state in the knowledge graph.

In response to identifying the node 1110 corresponding to the user's current state (e.g., a going-out state), the electronic device, according to an embodiment, may identify one or more other nodes connected to the node 1110 in the knowledge graph. Referring to FIG. 11, the electronic device may identify a sequence of states corresponding to each of a plurality of nodes 1110, 1120, 1130, 1140, 1150, 1160 and 1170, based on sequential connections of the plurality of nodes 1110, 1120, 1130, 1140, 1150, 1160 and 1170 in the knowledge graph.

For example, the electronic device may identify a sequential connection of the plurality of nodes 1110, 1120, 1130, 1140, 1150, 1160 and 1170, based on the nodes indicating the set of states 1100. Referring to FIG. 11, the set of states 1100 may include a plurality of states each corresponding to actions that the user may perform in turn to achieve the purpose of attending a meeting. For example, the set of states 1100 may include sequentially connected nodes, such as a node 1110 corresponding to a going-out state, a node 1120 corresponding to a state of sending a message (e.g., a message such as, "I am leaving"), a node 1130 corresponding to a state of getting in a vehicle, a node 1140 corresponding to a state of setting an electronic device, such as a cellular phone, a node 1150 corresponding to a driving state, a node 1160 corresponding to a state of arriving at a location related to a meeting, and a node 1170 corresponding to a state of meeting with another person.

Referring to FIG. 11, the electronic device, according to an embodiment, may track a change in the user's state, based on one or more other nodes connected to a node corresponding to the user's current state in the knowledge graph. Tracking the change in state by the user of the electronic device may include, for example, an operation of determining whether the tracked change in state of the user corresponds to a sequence of states occurring based on the sequential connection between the plurality of nodes 1110, 1120, 1130, 1140, 1150, 1160 and 1170. The electronic device may track the change in state by the user to execute a function related to the tracked user's state and/or a function related to a next state of the tracked user's state.

The electronic device, according to an embodiment, may perform a positive suggestion based on a function related to a state subsequent to the user's current state, based on at least one of the operations of FIG. 10. Referring to FIG. 11, based on sequential connections of a node 1110 corresponding to the user's current state and a plurality of nodes 1110, 1120, 1130, 1140, 1150, 1160 and 1170 including the node 1110, the electronic device, according to an embodiment, may identify a next state of the user subsequent to the state corresponding to the node 1110. For example, based on the node 1120 directly connected to the node 1110 in the sequential connections, the electronic device may predict the next state subsequent to the user's current state corresponding to the node 1110. Referring to FIG. 11, the node 1120 connected to a node 1110 corresponding to the current state, which is a node based on a class indicating a user's state, may correspond to a state of transmitting a message.

Referring to FIG. 11, in response to identifying the node 1120 connected to the node 1110 corresponding to the current state of the user, the electronic device, according to an embodiment, may execute a function related to the state corresponding to the identified node 1120 based on the active recommendation. For example, since the node 1120 corresponds to a state of transmitting a message, the electronic device may predict transmission of the message by the user. When transmission of the message by the user is predicted, the electronic device may execute a function corresponding to a next state related to the predicted transmission of the message. The electronic device, according to an embodiment, may identify a function corresponding to the next state, using one or more nodes connected to the node 1120 corresponding to the next state. When the node 1120 includes an attribute related to the active recommendation (e.g., an attribute indicating a state related to the active recommendation), the electronic device, according to an embodiment, may use the one or more nodes connected to the node 1120 to execute the function related to the node 1120.

Referring to FIG. 11, the electronic device, according to an embodiment, may use other nodes 1122, 1124, 1126, and 1128 connected to the node 1120 and corresponding to another class distinct from the node 1120 in the knowledge graph to predict an action of the user in the state corresponding to the node 1120. The connections between the node 1120 and other nodes 1122, 1124, 1126, and 1128 are not limited to the example shown in FIG. 11, and in the knowledge graph, the nodes 1124, 1126, and 1128 may be, for example, directly connected to the node 1120 via the node 1122. Referring to FIG. 11, a connection between the nodes 1120, 1122, 1124, 1126, and 1128 may include an identifier indicating a relationship between the nodes. The identifier may indicate a triple format predicate. For example, a performance-related identifier (e.g., performed by) assigned between the nodes 1120 and 1122 may indicate that a state associated with the node 1120 (e.g., a state of transmitting a message by the user) is a state performed based on a function (e.g., text input function) of an application associated with the node 1122. For example, an identifier (e.g., occupy) associated with an occupy action assigned between the nodes 1122 and 1128 may indicate that the function (e.g., text input function) of the application associated with node 1120 occupy a body part (e.g., hand) associated with the node 1128. For example, an identifier (e.g., withApp) assigned between the nodes 1122 and 1124 may indicate that the function (e.g., text input function) of the application related to the node 1122 is executed in the application related to the node 1124. For example, an identifier (e.g., withObj) allocated between the nodes 1124 and 1126 may indicate that an application related to the node 1124 is executed by an element related to the node 1126 (e.g., the electronic device 101-2 of FIG. 1).

Referring to FIG. 11, the node 1122 connected to node 1120 corresponding to a state of transmitting a message (e.g., a message such as, "I'm leaving now") may be a node based on a class indicating a function of the application executable in the electronic device, such as, e.g., the node 480 of FIG. 4, and correspond to a function of receiving a text input. Referring to FIG. 11, a node 1124 that is indirectly connected to the node 1120 via the node 1122 may be a node based on a class indicating an application executable in the electronic device, such as, e.g., the node 470 of FIG. 4, and indicate an application to execute the function indicated by the node 1122. Referring to FIG. 11, the node 1126 that is indirectly connected to the node 1120 via the nodes 1122 and 1124 may be a node based on a class indicating an electronic device, such as, e.g., the node 460 of FIG. 4, and indicate the electronic device in which an application indicated by the node 1124 is installed. Referring to FIG. 11, the node 1128 that is indirectly connected to the node 1120 via the node 1122 may be a node corresponding to any one of the user's body parts, and indicate the user's hand such as, e.g., the node 423 of FIG. 4. In the example of FIG. 11, in response to identifying other nodes 1122, 1124, 1126, and 1128 connected to the node 1120, the electronic device, according to an embodiment, may predict that the user in a state corresponding to the node 1120 will perform a function (e.g., touch input) indicated by the node 1122, based on the application corresponding to the node 1124.

The electronic device, according to an embodiment, may execute a function to guide a user's action indicated by the nodes 1122, 1124, 1126, and 1128. For example, based on the node 1124 indicating the application among the nodes 1122, 1124, 1126, and 1128 connected to the node 1120, the electronic device may output to the user a UI for verifying whether to execute the application related to the node 1124. The UI may further include, for example, a message for verifying whether to execute the function indicated by the node 1122. In response to a user input related to the UI, the electronic device may execute an application related to the node 1124. The electronic device, according to an embodiment, may execute the application related to the node 1124, while the user's current state is in a state prior to the state corresponding to the node 1120 related to the node 1124, for example, in the state corresponding to the node 1110 connected to the node 1120. By executing the application related to the node 1124, the electronic device may cause the user's current state to switch from the state corresponding to the node 1110 to the state corresponding to the node 1120.

In an embodiment, the sequential connection of the plurality of nodes 1110, 1120, 1130, 1140, 1150, 1160 and 1170 may be created in the knowledge graph, as the electronic device performs the operations described above with reference to FIGS. 5 to 7. For example, the electronic device may identify, based on data indicating the history of the electronic device and/or the user, such as, e.g., raw data (e.g., the raw data 510 of FIG. 5), that the user sequentially performs actions related to each of a plurality of states corresponding to each of the plurality of nodes 1110, 1120, 1130, 1140, 1150, 1160 and 1170. In response to identifying that the user sequentially performs the actions related to each of the plurality of states, the electronic device may connect in sequence the plurality of nodes 1110, 1120, 1130, 1140, 1150, 1160 and 1170 respectively corresponding to each of the plurality of states in the knowledge graph. In an embodiment, the sequential connection of the plurality of nodes 1110, 1120, 1130, 1140, 1150, 1160 and 1170 may be generated in the knowledge graph, based on an application and/or a service provider (e.g., the service provider related to the electronic device 101-1 of FIG. 1).

As described above, the electronic device, according to an embodiment, may perform an active recommendation based on one or more nodes connected to each other in the knowledge graph. By performing such a positive recommendation, the electronic device may cause switching between the first state and the second state by the user. The positive recommendation may be performed based on predicting by the electronic device that the user's state will be switched from the first state to the second state. As the electronic device performs the active recommendation, the user in the first state may selectively execute a function of the electronic device corresponding to the second state.

Hereinafter, an operation that is performed by the electronic device, according to an embodiment, based on usage of a user's body part indicated by the knowledge graph is described in detail with reference to FIG. 12.

FIG. 12 is a flowchart illustrating an operation for controlling, by an electronic device, at least one of a user's state and another state related to an event, according to an embodiment. The electronic device of FIG. 12 may include the electronic devices 101-1, 101-2, 101-3 and 101-4 of FIG. 1 and/or the electronic device 101 of FIG. 2. The operation of the electronic device of FIG. 12 may be performed, for example, by the electronic device 101 and/or the processor 210 of FIG. 2. At least one of the operations of FIG. 12 may correspond to or be performed similarly to at least one of the operations of FIG. 3.

Referring to FIG. 12, in operation 1210, the electronic device, according to an embodiment, may identify an event for executing the second function related to the second state distinguished from the first state of the user corresponding to the first function, among a plurality of functions executable in the electronic device. For example, the electronic device may identify the event while executing the first function. For example, the electronic device may identify the event, after identifying the first state of the user corresponding to the first function based on information indicating the knowledge graph. For example, in response to identifying the event, the electronic device may use information indicating the knowledge graph to identify the first state corresponding to the first function and/or the second state corresponding to the identified event. The electronic device, according to an embodiment, may detect occurrence of the event, for example, after identifying the current state of the user based on at least one of the operations 310 and 320 of FIG. 3.

In an embodiment, the event may be an event that changes, interrupts and/or interferes with the user's action, and include, for example, an event requesting establishment of a call connection, an event generating an alarm signal, and/or an event for displaying a notification provided based on a service related to a messenger application. As described above, the subject generating the event may include an electronic device and/or an external electronic device distinct from the electronic device. The event may cause an operation(s) of one or more applications being executed in the electronic device to at least temporarily cease. As the operation of one or more applications is at least temporarily ceased, an interaction between the electronic device and the user based on the operation may be at least temporarily interrupted. The second state related to the event may include, for example, a state of interrupting the interaction between the user in the first state and the electronic device.

The electronic device, according to an embodiment, may, for example, identify a current state of the user (e.g., the first state of the user) by performing at least one of the operations of FIG. 8. For example, with information indicating the knowledge graph, the electronic device, according to an embodiment, may identify the first state of the user among a plurality of states, based on information indicating a connection between a plurality of first nodes corresponding to different body parts and the second nodes corresponding to the plurality of states. The electronic device, according to an embodiment, may obtain, data indicating a connection between a node corresponding to the first state of the user and nodes corresponding to each of the body parts, among the plurality of states, based on the information indicating the knowledge graph. The obtained data may be data indicating a node corresponding to the first state in the knowledge graph and one or more other nodes connected to the node. In an embodiment, the operation 1210 may be performed while identifying by the electronic device the current state of the user. In an embodiment, in response to identifying the event of operation 1210, the electronic device may identify the current state of the user.

Referring to FIG. 12, in operation 1220, the electronic device, according to an embodiment, may determine whether a body part related to both the first state and the second state exists among the body parts. In the operation 1210, in response to identifying occurrence of the event, the electronic device, according to an embodiment, may identify a node connected in common to the first node corresponding to the first state and the second node corresponding to the second state, in the knowledge graph, before executing the second function related to the second state. The electronic device, according to an embodiment, may compare one or more nodes connected to the first node and one or more nodes connected to the second node to determine whether the body parts corresponding to each of the first state and the second state match each other. For example, the node connected in common to the first node and the second node may be based on a class related to a certain user's body part, such as the nodes 421, 422, 423, 424, 425 and 426 of FIG. 4. For example, a node connected in common to the first node and the second node, among the nodes corresponding to each of the body parts, may imply that the node is commonly used for both the action of the user corresponding to the first state and the action of the user corresponding to the second node. For example, as the body part is used for both the user's action corresponding to the first state and the user action corresponding to the second state, the user may perform the action corresponding to the other state only after ceasing the action corresponding to either one state of the first state or the second state.

For example, when simultaneously performing actions corresponding to each of the first state of driving a vehicle and the second state of reading a text message, the user has to look at the front of the vehicle while also gazing at a display (e.g., the display 240 of FIG. 2). As the eyes of the user are commonly used for both the action corresponding to the first state and the other action corresponding to the second state, the user would not be able to simultaneously perform both the actions corresponding to each of the first state and the second state and would have to cease either one of the two actions at least temporarily. When the first state and the second state relate to the same body part and thus, they correspond to the actions that cannot be simultaneously performed, for example, when at least one body part is used for actions in both the first state and the second state, the electronic device, according to an embodiment, may prevent simultaneous execution of two functions respectively corresponding to the first state and the second state. In order to prevent simultaneous execution of the functions corresponding to each of the first state and the second state, the electronic device may execute another function that is distinguished from the second function and related to another state distinct from either one of the first state or the second state, using the knowledge graph.

Referring to FIG. 12, when the body parts corresponding to each of the first state and the second state are independent of each other ('NO' in operation 1220), in operation 1270, the electronic device, according to an embodiment, may execute the second function in response to the identified event. For example, the electronic device may compare one or more nodes connected to the first node corresponding to the first state and one or more nodes connected to the second node corresponding to the second state in the knowledge graph to identify that the first body part corresponding to the first state and the second body part corresponding to the second state are different from each other. In response to identifying that the first body part and the second body part are different, the electronic device may execute the second function related to the second state, based on the operation 1270.

For example, when there is no node connected in common to the first node corresponding to the first state and the second node corresponding to the second state in the knowledge graph, the electronic device may determine that the first state and the second state correspond to actions using different body parts of the user. When the first state and the second state correspond to the actions using different body parts of the user, the electronic device may determine that the actions can be simultaneously performed by the user. In such an instance, even if the action related to the second state is performed by the user in the first state, the motion of one or more body parts related to the first state may be maintained independently of performing the action related to the second state.

Referring to FIG. 12, when any body parts related to both the first state and the second state exist (YES' in operation 1220), in operation 1230, the electronic device, according to an embodiment, may identify one or more candidate states distinguished from the second state. The candidate state may include, for example, one or more sibling states included in the same layer as the second state in the knowledge graph. The nodes corresponding to the one or more candidate states and the second state may be connected to a node that is included in a higher layer of the nodes in the knowledge graph and generalized for the nodes. The electronic device, according to an embodiment, may identify the one or more candidate states, in a knowledge graph, based on another node that is connected to the second node corresponding to the second state and included in a higher layer higher of the second node.

In response to identifying a node corresponding to any one body part among the body parts, the node connected to both the first node corresponding to the first state and the second node corresponding to the second state, in the knowledge graph, the electronic device, according to an embodiment, may identify one or more nodes corresponding to each of one or more candidate states distinct from the second state. One or more nodes corresponding to each of the one or more candidate states, being sibling states of the second node corresponding to the second state, may be included, for example, in the same layer as the second node in the knowledge graph. For example, in the knowledge graph, the electronic device may identify the one or more candidate states distinct from the second state, based on one or more nodes included in the same layer as the second node corresponding to the second state.

As described above, the candidate states identified by the electronic device based on the operation 1230 may indicate an action similar to the action corresponding to the second state. The electronic device, according to an embodiment, may allocate nodes corresponding to the similar action and/or state among a plurality of nodes in the knowledge graph, in the same layer within the knowledge graph, based on a neural network learned based on machine learning. The electronic device, according to an embodiment, may assign the attributes indicating that the nodes correspond to the similar actions and/or state, to nodes corresponding to the similar action and/or state among a plurality of nodes in the knowledge graph, based on the learned neural network.

Referring to FIG. 12, in operation 1240, the electronic device, according to an embodiment, may determine whether, among the candidate states, there exists a candidate state related to another body part distinct from one or more body parts related to the first state. For each of the one or more candidate states identified based on the operation 1230, the electronic device, according to an embodiment, may identify at least one node that is connected to a node corresponding to the candidate state in the knowledge graph and based on a class indicating a body part of the user. The electronic device, according to an embodiment, may compare one or more body parts used by the user in the first state and one or more body parts used by the user in each of the candidate states, by comparing one or more nodes connected to the first node corresponding to the first state and one or more nodes connected to each of the candidate states. For each of the one or more candidate states identified based on the operation 1230, the electronic device, according to an embodiment, may identify a node connected in common to the first node corresponding to the first state and a node corresponding to the candidate state, in the knowledge graph. When the node connected in common to the first node and the node corresponding to the candidate state are identified, the electronic device may determine whether the class of the identified node is a class indicating a body part of the user. When the class of the identified node is a class indicating the body part of the user, the electronic device may determine that both the first state and the candidate state use the same body part.

The electronic device, according to an embodiment, may sequentially access all nodes corresponding to each of the candidate states in the knowledge graph to identify a node independent of one or more body parts related to the first state, among the nodes corresponding to each of the candidate states. The electronic device, according to an embodiment, may compare one or more nodes connected to each of the nodes corresponding to each of the candidate states and one or more nodes connected to the first node associated with the first state to identify a candidate state independent of the one or more body parts related to the first state. For example, when a node is identified that is connected to the first node related to the first state and is independent of one or more nodes based on a class indicating a body part, the electronic device may determine that the candidate state corresponding to the identified node is related to another body part distinct from the one or more body parts associated with the first state.

If there is the candidate state related to another body part distinct from the one or more body parts associated with the first state ('YES' in the operation 1240), in operation 1245, the electronic device, according to an embodiment, may execute a third function corresponding to the candidate state related to the other body part, in response to the identified event. The electronic device, according to an embodiment, may execute the third function distinct from the second function, in response to an event executing the second function. For example, despite occurrence of the event executing the second function, the electronic device may execute the third function distinct from the second function, while at least temporarily ceasing the execution of the second function. Since the third function is related to another body part distinct from the one or more body parts related to the first state, performing the action related to the first state by the user may be maintained. For example, the third function may be a function that can be performed while maintaining an action related to the first state of the user. The third function may be a function different from the second function related to the second state of the user, switching the user's state to the candidate state corresponding to the third function.

When there exists no candidate state associated with another body part distinguished from one or more body parts associated with the first state ('NO' in operation the 1240), in operation 1250, the electronic device, according to an embodiment, may determine whether a priority of the second state is higher than that of the first state. Based on the attributes assigned to each of the first node corresponding to the first state and the second node corresponding to the second state in the knowledge graph, the electronic device may identify the priority of each of the first state and the second state. When there exists no candidate state associated with another body part distinguished from the one or more body parts associated with the first state ('NO' in the operation 1240), the electronic device may determine whether to execute the second function associated with the second state based on the identified priority. The electronic device, according to an embodiment, may change the mode of the electronic device related to the first state and/or the second state, based on the identified priority.

When the priority of the second state is lower than the priority of the first state ('NO' in the operation 1250), the electronic device, according to an embodiment, may cease execution of the second function related to the second state. For example, independently of identification of the event in the operation 1210, the electronic device may cause the user's state to be maintained in the first state. Referring to FIG. 12, while the user's current state corresponds to the first state, in case where the second state associated with the event of the operation 1210 is associated with one or more body parts corresponding to the first state ('YES' in the operation 1220), there is no candidate state associated with another body part distinct from the one or more body parts associated with the first state among the candidate states similar to the second state ('NO' in the operation 1240), and the priority of the second state is lower than that of the first state ('NO' in the operation 1250), then the electronic device may stop execution of the first function corresponding to the second state.

Referring to FIG. 12, when the priority of the second state is higher than the priority of the first state ('YES' in operation 1250), in operation 1260, the electronic device, according to an embodiment, may determine whether the body part associated with both the first state and the second state is exclusively used by the user in the first state. The electronic device, according to an embodiment, may identify a node based on a class related to the body part, among nodes connected in common to the first node corresponding to the first state and the second node corresponding to the second state in a knowledge graph. Based on the characteristic of the body part corresponding to the identified node, the electronic device may determine whether the body part associated with both the first state and the second state is exclusively used by the user in the first state. Such an exclusive use of a specific body part may imply that the specific body part is in a dedicated use for the user to perform an action corresponding to a specific state, for example, as if the user has to selectively gaze at different objects with his/her eyes.

For example, the exclusive use of a specific body part for a specific state may be associated with the characteristics of the body part, as if the user has to selectively gaze at various objects using his/her eyes or the user can simultaneously hear multiple sounds using his/her ears. The electronic device may indicate whether a body part corresponding to a certain node is exclusively used by a certain action of the user, in the attributes of nodes corresponding to each of different body parts in the knowledge graph. The electronic device, according to an embodiment, may, based on the attributes of a node based on a class related to a body part, the node being connected to both the first node and the second node, determine whether the node corresponds to an exclusively used body part.

When the body part associated with both the first state and the second state is exclusively used by the first state ('YES' in the operation 1260), in operation 1262, the electronic device, according to an embodiment, may at least temporarily cease the first function associated with the first state. Since the operation 1262 is performed in a state in which the priority of the second state is higher than the priority of the first state ('YES' in the operation 1250), the electronic device may cause using at least one body part of the user for the action in the first state to be at least temporarily ceased. For example, the electronic device may cause the first function provided to the user in relation to the first state, among the plurality of functions, to be at least temporarily ceased. As the electronic device ceases execution of the first function, the body part being exclusively used by the user in the first state may be available to the user in the second state.

For example, when the user's current state corresponds to the first state related to the first function executing a first application (e.g., a gaming application) occupying the entire display area of the display (e.g., a display 240 of FIG. 2) of the electronic device, the electronic device may detect occurrence of an event (e.g., reception of a request for video call) executing the second function (e.g., a video call function by a phone application) related to the second state for a video call. In the above example, it is assumed that there is no candidate state to replace the second state for the video call. Since the priority of the second state for the video call is higher than that of the first state and the users eyes cannot gaze at different objects and/or screens at the same time, the electronic device may at least temporarily interrupt the first function having a relatively low priority (e.g., the function of executing the first application). For example, the electronic device may execute a function to terminate the first application.

When the body part associated with both the first state and the second state is not exclusively used by the first state ('NO' in the operation 1260), in operation 1264, the electronic device, according to an embodiment, may execute a fourth function to reduce the extent to which the body part associated with both the first state and the second state is used based on the first state. Since the operation 1264 is performed in a state in which the priority of the second state is higher than that of the first state ('YES' in the operation 1250), the electronic device may reduce the usage of the body part by the first state of the first state and the second state. When a specific body part is not exclusively used by a specific state, it may imply that the specific body part is partially used by the specific state.

For example, when the current state of the user corresponds to the first state executing the first function of listening to music, the electronic device may detect occurrence of an event (e.g., reception of a request for voice call) executing the second function (e.g., a voice call function by a phone application) related to the second state for a voice call. In the above example, it is assumed that there is no candidate state to replace the second state for the voice call. Since the priority of the second state for a voice call is higher than that of the first state of listening to music, and the user's ear is a body part capable of simultaneously listening to sounds generated from different sources, that is, it is a body part that is partially available by each of multiple states, the electronic device may cause execution of the second function related to the second state. While executing the second function, since the priority of the second state corresponding to the second function is higher than that of the first state, the electronic device may execute, for example, a function of reducing volume for a music application and/or switching the volume to muting, as the fourth function for reducing the extent to which the users ear is used based on the first state of listening to music.

Referring to FIG. 12, in operation 1270, the electronic device, according to an embodiment, may execute the second function in response to the identified event. In a state in which the user's current state corresponds to the first state, the electronic device, according to an embodiment, may execute the second function related to the identified event, when the priority of the second state corresponding to the second function is higher than that of the first state ('YES' in operation 1260, or each of the first state and the second state is related to different body parts ('NO' in the operation 1220). As the electronic device executes the second function based on the operation 1270, the current state of the user may be changed to the second state.

As described above, the electronic device, according to an embodiment, may selectively execute a function of maintaining a user's current action and/or a function corresponding to another action having a higher priority than the user's current action, using the knowledge graph structuralizing the user's actions distinguished by distinct states. As the knowledge graph corresponding to the user is personalized based on, for example, the operations described above with reference to FIGS. 5 to 6, the electronic device may more accurately identify the user's current action and/or the user's current state. As described above, at least one of a plurality of operations shown in FIG. 12 may be performed by the electronic device searching for at least a part of the knowledge graph, according to an embodiment.

The electronic device, according to an embodiment, may perform at least one of the operations of FIG. 12, based on a rule of searching the knowledge graph. For example, the electronic device may perform at least one of the operations 1220 and 1260, by searching the knowledge graph based on a rule for identifying a body part related to a specific state. For example, the electronic device may perform the operation 1230, by searching the knowledge graph based on a rule for identifying a candidate state. For example, the electronic device may perform the operation 1250, by searching the knowledge graph based on a rule for identifying the priorities of distinct states. The rule for searching the knowledge graph may be, for example, identified by a process executable in the electronic device, such as the information extraction unit 550 of FIG. 5, and/or provided by a service provider providing the service related to the knowledge graph.

As described above, the electronic device, according to an embodiment, may identify a change in the usage of a body part according to the user's simultaneous performing several actions. For example, when the user simultaneously performs different actions corresponding to each of the first state and the second state, the electronic device may identify overusing of the body part by the different actions, by using one or more nodes connected to both the first node corresponding to the first state and the second node corresponding to the second state, in the knowledge graph. As the overusing of the body part is predicted, the electronic device, according to an embodiment, may prevent the user from simultaneously performing an action corresponding to the first state and an action corresponding to the second state (e.g., the operations 1245 and 1262), or at least alleviate overusing of the body part (e.g., the operation 1264).

Hereinafter, an example in which the electronic device performs at least one of the operations of FIG. 12 will be described based on the exemplary instances of FIGS. 13 to 18.

Figure 13:
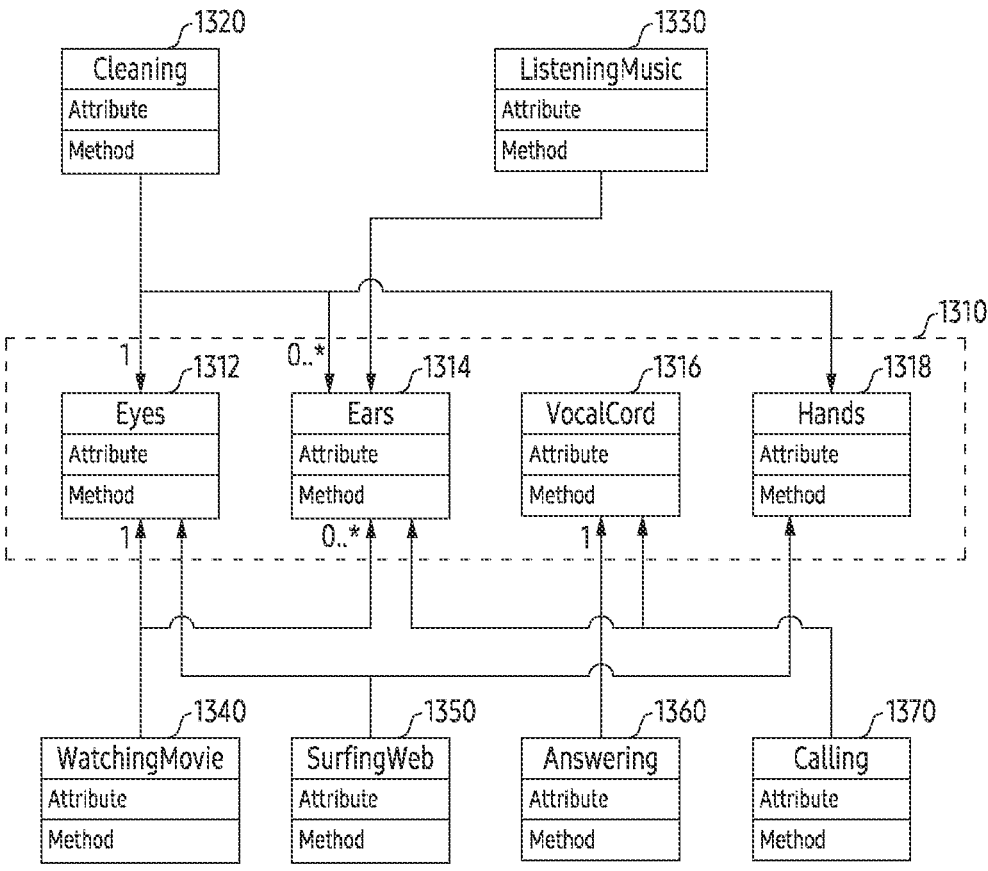
FIG. 13 is a diagram illustrating an operation performed by an electronic device using a knowledge graph according to an embodiment.

FIG. 13 is an exemplary diagram for describing an operation performed by an electronic device using a knowledge graph, according to an embodiment. The electronic device of FIG. 13 may include the electronic devices 101-1, 101-2, 101-3 and 101-4 of FIG. 1 and/or the electronic device 101 of FIG. 2. The knowledge graph of FIG. 13 may correspond to at least a portion of the knowledge graphs 121, 121-1, 121-2, 122, 123 and 124 of FIG. 1 and the knowledge graph 120 of FIG. 2.

Referring to FIG. 13, a plurality of nodes 1312, 1314, 1316 and 1318 included in a class 1310 indicating different body parts of the user in the knowledge graph are shown. For example, the node 1312 corresponds to an eye of the user's body parts, the node 1314 corresponds to an ear of the user's body parts, the node 1316 corresponds to vocal cords of the user's body parts, and the node 1318 may correspond to hands of the user's body parts.

Referring to FIG. 13, in the knowledge graph are shown the nodes 1320, 1330, 1340, 1350, 1360, and 1370 respectively corresponding to distinct states of the user. The nodes 1320, 1330, 1340, 1350, 1360 and 1370 may be connected to a node included in the class 1310 to indicate one or more body parts used by the user in a certain state. For example, the node 1320 corresponding to a cleaning state may be connected to the nodes 1312, 1314 and 1318 included in the class 1310 to indicate that the user in the cleaning state uses the eyes, ears, and hands. For example, the node 1330 corresponding to a state of listening to music may be connected to the node 1314 included in the class 1310 to indicate that the user in a state of listening to music uses the ears. For example, the node 1340 corresponding to a state of watching the movie may be connected to the nodes 1312 and 1314 included in the class 1310 to indicate that the user in a state of watching the movie uses the eyes and ears. For example, the node 1350 corresponding to a web surfing state may be connected to the nodes 1312 and 1318 included in the class 1310 to indicate that the user in a web surfing state uses his/her eyes and hands. For example, the node 1360 corresponding to a state of answering a question may be connected to the node 1316 included in the class 1310 to indicate that the user in the state of answering uses the vocal cords. For example, the node 1370 corresponding to a state of making a call may be connected to the nodes 1314 and 1316 included in the class 1310 to indicate that the user in a state of making a call uses his/her ears and vocal cords.

Referring to an example of the knowledge graph of FIG. 13, the nodes 1320, 1330, 1340, 1350, 1360 and 1370 each corresponding to the distinct states of the user included in the class 1310 may be connected to at least one of the nodes 1312, 1314, 1316 and 1318, based on intensity. The intensity assigned between the node corresponding to a specific state and the node corresponding to a specific body part may indicate the usage of the specific body part used by the user in the specific state. For example, the usage amount may indicate whether a body part is exclusively used by the user and/or the extent to which it is partially used.

For example, the node 1320 corresponding to a state of cleaning may be connected to each of the nodes 1312 and 1318 corresponding to eyes and hands, based on a predetermined intensity (e.g., level 1 and/or a truth value such as 'true') indicating exclusive use of the body part. The node 1320 corresponding to the cleaning state may be connected to the node 1314 corresponding to the ear, based on the intensity (e.g., a rational number in floating-point format greater than 0 and less than 1) indicating a partial use of the body part, in order to indicate generation of noise due to the cleaning action. The node 1320 corresponding to the cleaning state may be not connected to the node 1316 corresponding to the vocal cords so as to indicate that the vocal cords are not used, or may be connected thereto based on a predetermined intensity (e.g., a truth value such as 0 and/or 'false') indicating disconnection of the node 1316. In an embodiment, the intensity may mean a score indicating occupation of a specific body part by the user in a specific state.

When a plurality of actions corresponding to distinct states are simultaneously performed by the user, using the knowledge graph, the electronic device, according to an embodiment, may identify a constraint of any one action of a plurality of actions occurring in at least one of the user's body parts and/or an interference between the plurality of actions. In order to prevent the constraint and/or the interference, the electronic device, according to an embodiment, may perform at least one of the operations of FIGS. 3 and/or 12.

For example, eyes, vocal cords, and hands among the body parts may have the characteristics that cannot simultaneously perform different actions. Referring to FIG. 13, the node 1312 corresponding to the eye may be connected to the nodes 1320, 1340, and 1350 based on the intensity indicating the exclusive use of the body part, so that the actions corresponding to each of the nodes 1320, 1340, and 1350 cannot be performed at the same time as they require the eyes at the same time. For example, the fact that one cannot watch a movie and surf the web at the same time may be represented through the connection between the node 1312 and the nodes 1340 and 1350 in the knowledge graph.

For example, the ears and the nose among the body parts can simultaneously detect sounds and smells generated from different sources. Referring to FIG. 13, the node 1314 corresponding to the ear may be connected to the nodes 1320, 1330, 1340 and 1370 based on the intensity indicating the partial use of the body part, to indicate that the user can hear the sound corresponding to each of the nodes 1320, 1330, 1340 and 1370. For example, the fact that one can simultaneously hear both the sound output in the movie being played and the sound of the other party connected over a phone call may be represented through the connection between the node 1314 and the nodes 1340 and 1370 in the knowledge graph. The intensity assigned to each connection of the node 1314 corresponding to the ear and the nodes 1320, 1330, 1340 and 1370 corresponding to distinct states may correspond to each volume of the sounds generated from the nodes 1320, 1330, 1340 and 1370.

As described above, the electronic device may obtain the knowledge graph indicating the user's action and the usage of body parts by the action, based on the connection between the nodes. Hereinafter, an operation performed by the electronic device based on the exemplary knowledge graph of FIG. 13 will be described in detail with further reference to FIGS. 14 to 17.

Figure 14:
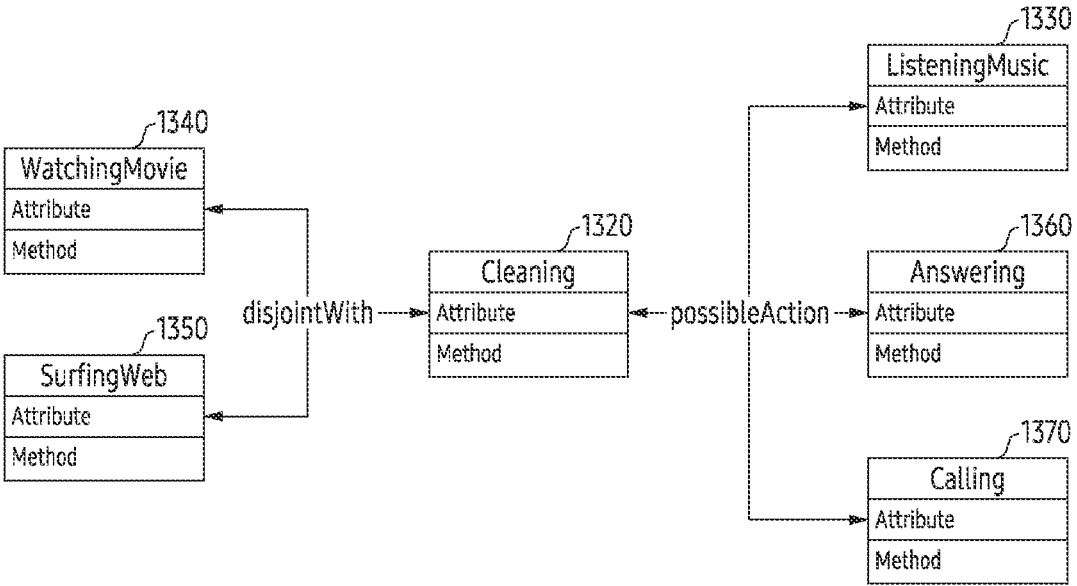
FIG. 14 is a diagram illustrating a connection between distinct states in a knowledge graph stored in an electronic device according to an embodiment.

FIG. 14 is an exemplary diagram for explaining a connection between distinct states in a knowledge graph stored in an electronic device according to an embodiment. The electronic device of FIG. 14 may include the electronic devices 101-1, 101-2, 101-3 and 101-4 of FIG. 1 and/or the electronic device 101 of FIG. 2. The knowledge graph of FIG. 14 may correspond to at least a portion of the knowledge graphs 121, 121-1, 121-2, 122, 123 and 124 of FIG. 1 and the knowledge graph 120 of FIG. 2. The knowledge graph of FIG. 14 may represent a relationship between nodes identified based on the knowledge graph of FIG. 13.

The electronic device, according to an embodiment, may identify an action that can be performed by the user in a current state, by searching the knowledge graph based on the current state of the user. For example, in the operations 320 and 340 of FIG. 3 and the operations 1220, 1240 and 1260 of FIG. 12, the electronic device may search the knowledge graph to identify an action that can be performed by the user in the current state. Hereinafter, while the user is in the cleaning state, an operation in which the electronic device, according to an embodiment, searches the knowledge graph to identify one or more actions capable of being performed by the user will be described in more detail. In response to identifying activation of a robot cleaner (e.g., an electronic device 101-3 of FIG. 1), the electronic device may determine that the current state of the user corresponds to the cleaning state. The electronic device may identify the activation of the robot cleaner, for example, based on at least one of a signal received from the robot cleaner connected through a network, a user input for activating the robot cleaner using the electronic device, or information indicating a schedule of the robot cleaner input from the user.

Referring to FIG. 14, in response to identifying that the user's current state corresponds to the cleaning state, the electronic device, according to an embodiment, may identify a node 1320 corresponding to the cleaning state in the knowledge graph. The electronic device may determine the identified node 1320 as a node corresponding to the user's current state. Hereinafter, it is assumed that the node 1320 identified by the electronic device is included in part of the knowledge graph shown in FIG. 13. Referring to FIG. 13, a node 1320 may be connected to nodes 1312, 1314 and 1318 included in a class 1310 representing different body parts, so as to indicate that the user in a cleaning state may use his/her eyes, ears, and hands. The electronic device, according to an embodiment, may be connected to the node 1320 corresponding to the current state, and based on another node indicating a body part, identify an action that can be performed by the user in the current state (or an interruption of an action corresponding to the current state and/or another action that can be performed without interruption).

In an embodiment, for a specific node connected based on a predetermined intensity indicating its exclusive use with a node corresponding to a current state, among nodes included in a class indicating a body part, the electronic device may identify that an action related to another state corresponding to another node connected to the specific node ceases the action related to the current state. Referring to FIG. 13, based on a connection between the node 1320 corresponding to the current state and the nodes 1312, 1314 and 1318 included in the class 1310, the electronic device, according to an embodiment, may identify other node connected to the node 1320 via the nodes 1312, 1314 and 1318. Referring to FIG. 13, the nodes 1340 and 1350 may be connected to the node 1320 via the node 1312, and the node 1350 may be connected to the node 1320 via the node 1318. Each of the nodes 1312 and 1318 of FIG. 13 may correspond to the eye and the hand of the user, which are of exclusively used body parts. For example, in FIG. 13, the connection between the node 1312 corresponding to the eye and the nodes 1320, 1340, and 1350 and the connection between the node 1318 corresponding to the hand and the nodes 1320, 1350 may have a predetermined intensity indicating their exclusive use. For a specific node (e.g., nodes 1312 and 1318 of FIG.

13) connected, based on the predetermined intensity indicating the exclusive use, with the node corresponding to the current state (e.g., a node 1320 of FIG. 13), the electronic device, according to an embodiment, may identify another state ceasing the action related to the current state, based on a node (e.g., nodes 1340 and 1350 of FIG. 13) connected to the specific node and corresponding to the other state distinct from the current state. The identified other state and the current state may be connected to each other based on a parameter indicating sharing of the body part used exclusively in the knowledge graph. Referring to FIG. 14, the connection between the nodes 1320, 1340 and 1350 corresponding to a plurality of states using the eyes and hands, which are exclusively used body parts may have a designated identifier (e.g., disjointWith) indicating that the actions corresponding to each of the plurality of states cannot be performed simultaneously by the user.

Referring to FIG. 13, the nodes 1330, 1340 and 1370 may be connected to the node 1320 via the node 1314. The node 1314 in FIG. 13 may correspond to the ear, which is a partially used body part. For example, the connection between the node 1314 and the nodes 1320, 1330, 1340 and 1370 of FIG. 13 may have an intensity indicating their partial use. The electronic device, according to an embodiment, may identify distinct states corresponding to different actions that can be performed at the same time with the action related to the current state, by identifying the node (e.g., nodes 1330, 1360 and 1370 of FIG. 13) connected to a specific node and corresponding to another state distinct from the current state, where the specific node (e.g., a node 1314 of FIG. 13) is connected, based on the intensity indicating its partial use, with the node corresponding to the current state (e.g., a node 1320 of FIG. 13). The identified other state and the current state may be connected to each other based on the parameter indicating sharing of a partially used body part in the knowledge graph. Referring to FIG. 14, the connection between the nodes 1320, 1330, 1360 and 1370 corresponding to a plurality of states related to the ear, which is a partially available body part, may have a designated identifier (e.g., possibleAction) indicating that actions corresponding to each of the plurality of states are actions that can be simultaneously performed by the user.

The electronic device, according to an embodiment, may perform at least one of the operations of FIGS. 3, 10, and/or 12, based on the connection between the nodes corresponding to each of the distinct states. For example, when the current state of the user corresponds to the state indicated by the node 1320, the electronic device may identify the connection between the nodes 1320 and 1350, in response to occurrence of an event of executing the web browser associated with the node 1350. Referring to FIG. 14, since the connection between the nodes 1320 and 1350 has a designated identifier (e.g., disjointWith) indicating that the user cannot simultaneously perform the actions, the electronic device, according to an embodiment, may execute a function to cease the cleaning (e.g., a function to transmit a signal to deactivate the robot cleaner) being executed by the user, and/or cease execution of the web browser at least temporarily. For example, when the priority of the state of executing the web browser is higher than that of the cleaning state, the electronic device may cease cleaning and execute the web browser. For example, the electronic device may obtain the priority of the state of executing the web browser from the attributes of the node 1350 related to the state of executing the web browser. For example, the electronic device may obtain the priority of the cleaning state from the attributes of the node 1329 related to the cleaning state. By comparing the obtained priorities, the electronic device may selectively execute the function of ceasing the cleaning and/or the function of ceasing execution of the web browser. For example, when the current state of the user is a state corresponding to the node 1320, in response to occurrence of an event for establishing a call connection related to the node 1370, the electronic device may identify a connection between the nodes 1320 and 1370. Referring to FIG. 14, since the connection between the nodes 1320 and 1370 has a designated identifier (e.g., possibleAction) indicating that the user can simultaneously perform the actions, the electronic device, according to an embodiment, can establish the call connection.

As described above, the electronic device, according to an embodiment, may cause nodes corresponding to each of distinct states for distinguishing different actions of the user in the knowledge graph to be connected to each other, based on a parameter indicating simultaneity of the states. As the connection between the nodes has the parameter indicating simultaneity, the electronic device may identify the states related to the actions that the user cannot simultaneously perform, based on the connection between a node corresponding to the current state and another node in the knowledge graph. The actions that the user cannot perform simultaneously may correspond to, for example, different actions using a body part that has to be exclusively used. Based on the current state of the user, the electronic device, according to an embodiment, may, in response to occurrence of an event requesting other action that cannot be simultaneously performed by the user in the current state, adjust the current state of the user and/or cause the user to execute a function related to another action distinct from the other action.

Hereinafter, an operation of recognizing a user's action by an electronic device using a knowledge graph according to an embodiment will be described in detail with further reference to FIGS. 15 to 17.

Figure 15:
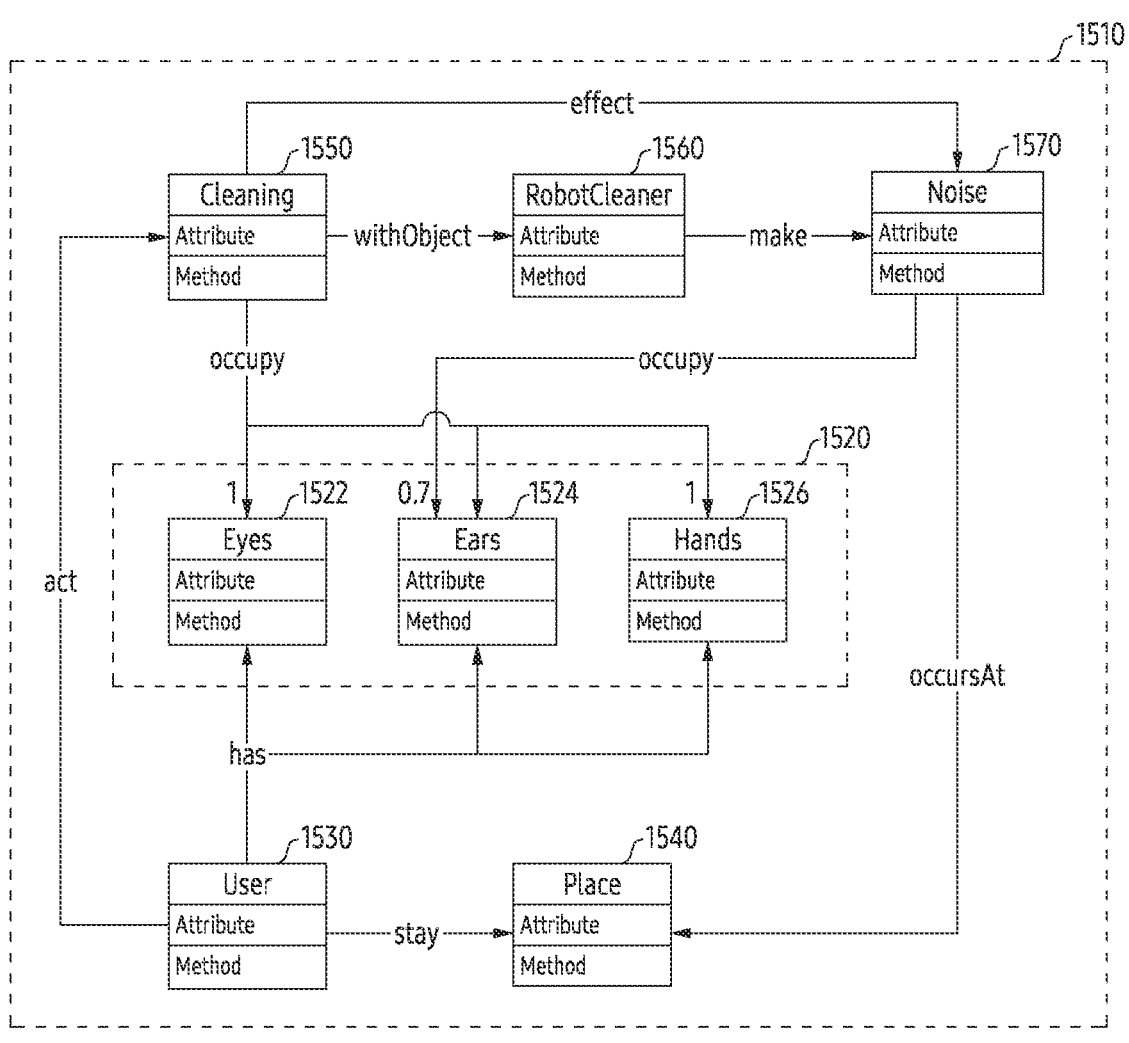
FIG. 15 is a diagram illustrating an operation of an electronic device acquiring one or more other nodes connected to a node indicating a user's state, based on a knowledge graph, according to an embodiment.

FIG. 15 is an exemplary diagram for explaining an operation of obtaining, by an electronic device, data indicating a state of the user, based on the knowledge graph, according to an embodiment. The electronic device of FIG. 15 may include the electronic devices 101-1, 101-2, 101-3 and 101-4 of FIG. 1 and/or the electronic device 101 of FIG. 2. The knowledge graph of FIG. 15 may correspond to at least a portion of the knowledge graphs 121, 121-1, 121-2, 122, 123 and 124 of FIG. 1 and the knowledge graph 120 of FIG. 2. The knowledge graph of FIG. 15 may represent a relationship between nodes identified based on the knowledge graph of FIGS. 13 to 14.

Referring to FIG. 15, a portion 1510 of the knowledge graph 120 (e.g., a knowledge graph 120 of FIG. 2) obtained from a memory (e.g., a memory 220 of FIG. 2) is shown, based on the current state of the user. Hereinafter, an operation in which the electronic device, according to an embodiment, recognizes the user's action using the portion 1510 of the knowledge graph, while the user is cleaning, will be described in detail. The electronic device, according to an embodiment, may selectively execute at least one function among a plurality of functions, based on the recognized action.

The electronic device, according to an embodiment, may connect the node 1530 corresponding to the user and other nodes 1522, 1524, 1526, 1540, 1550 and 1560 in the knowledge graph to obtain a portion of the knowledge graph indicating a state of the user. Referring to FIG. 15, the electronic device may use the nodes 1522, 1524 and 1526 included in a class 1520 indicating body parts to indicate the attributes (e.g., usage) of the body parts corresponding to each of the nodes 1522, 1524 and 1526. For example, the node 1522 may include attributes related to the user's eyes. For example, the node 1524 may include attributes related to the user's ears. For example, the node 1526 may include attributes related to the user's hands. Referring to FIG. 15, the node 1530 corresponding to the user and the nodes 1522, 1524, and 1526 corresponding to different body parts may be connected to each other, based on a predetermined parameter indicating that it is a body part of the user. Although the nodes 1522, 1524 and 1526 corresponding to some of the body parts in class 1520 are shown, the embodiment is not limited thereto, for example, nodes corresponding to other body parts not shown in the class 1520, such as 421, 422, 423, 424, 425 and 426 of FIG. 4, may be further included.

The electronic device, according to an embodiment, may indicate location of the user by connecting the node 1530 corresponding to the user with a node 1540 corresponding to a class indicating the spatial location, in the knowledge graph. Referring to FIG. 15, the electronic device may assign a specified parameter (e.g., stay) for indicating the current location of the user to the connection between the nodes 1530 and 1540, so as to determine the location of the user in the knowledge graph.

The electronic device, according to an embodiment, may connect the node 1530 corresponding to the user in the knowledge graph to another node, based on the user state detected based on the electronic device and/or an external electronic device connected to the electronic device. For example, the electronic device corresponding to the user terminal (e.g., an electronic device 101-2 of FIG. 1) may, in response to receiving a signal indicating activation of the robot cleaner (e.g., an electronic device 101-3 of FIG. 1), identify that the user's current state corresponds to the cleaning state. The electronic device, according to an embodiment, may connect the node 1550 corresponding to the cleaning state with the node 1530 corresponding to the user, among the nodes based on the class indicating the user's state. Referring to FIG. 15, the electronic device may indicate the current state and/or current action of the user in the knowledge graph, by allocating a specified parameter (e.g., act) for indicating the user's action in between the nodes 1530 and 1550.

The electronic device, according to an embodiment, may recognize the users action in the current state, based on one or more other nodes connected to the node 1550, in response to connecting between the nodes 1530 and 1550. Referring to FIG. 15, the node 1550 corresponding to the cleaning state may be connected to the node 1560 indicating the robot cleaner, based on a specified parameter (e.g., withObject) indicating that it is an object associated with the cleaning state. The connection between the nodes 1550 and 1560 may be provided by a service provider (e.g., a vendor of the robot cleaner) that provides the service related to the knowledge graph. In an embodiment, the electronic device may connect the nodes 1550 and 1560 to each other in the knowledge graph, by performing at least one of the operations of FIGS. 5 to 6. In response to identifying the connection between the nodes 1550 and 1560, the electronic device may recognize that the robot cleaner is being used by the user in the cleaning state. The electronic device may allocate the attributes related to the robot cleaner (e.g., an identifier of the robot cleaner in the network such as, e.g., Internet Protocol (IP) address and/or media access controller (MAC) address, and the state of the robot cleaner) to the node 1560.

Referring to FIG. 15, the electronic device, according to an embodiment, may recognize the fact that the robot cleaner makes noise, based on the connection between the node 1560 indicating the robot cleaner and the node 1570 indicating the noise. For example, the connection between the nodes 1560 and 1570 may have a designated parameter (e.g., make) indicating the generation of noise by the robot cleaner. Referring to FIG. 15, the node 1550 corresponding to a cleaning state may be connected to the node 1570 indicating the noise, via the node 1560 indicating the robot cleaner. Referring to FIG. 15, the nodes 1550 and 1570 may be connected to each other based on a specified parameter (e.g., effect) indicating an effect. For example, the electronic device may recognize that the noise is generated in the cleaning state, based on the specified parameter (e.g., effect) assigned to the connection between the nodes 1550 and 1570. For example, the electronic device may identify that the cleaning is a major cause of the noise, based on the connection between the nodes 1550, 1524 and 1570. Referring to FIG. 15, when the robot cleaner is present at the user's current location, the electronic device, according to an embodiment, may connect the node 1540 corresponding to the user's current location and the node 1570 indicating the noise to indicate that that the noise is generated at the user's current location, based on the knowledge graph.

Referring to FIG. 15, the electronic device, according to an embodiment, may identify one or more body parts related to the user's action (e.g., cleaning) in the current state, based on the connection between the node 1550 corresponding to the current state and the nodes 1522, 1524 and 1526 included in the class 1520 indicating the body part. For example, the node 1550 corresponding to the cleaning state may be connected to the nodes 1522, 1524 and 1526 respectively corresponding to the eyes, ears, and hands, based on its intensity. The intensity may indicate the usage of the body part used by the user in the current state. For example, since the connection between the nodes 1550 and 1522 has a predetermined intensity indicating the exclusive use of the body part, the electronic device may recognize that the user's eyes are exclusively used for cleaning in the cleaning state. For example, since the connection between the nodes 1530 and 1524 has the intensity indicating partial use of the body part, the electronic device may recognize that the user's ears are partially used in the cleaning state. For example, since the connection between nodes 1550 and 1520 has the specified intensity indicating the exclusive use of the body part, the electronic device may recognize, in the cleaning state, that the user's hands are exclusively used for cleaning.

As described above, the electronic device, according to an embodiment, may connect a plurality of nodes in the knowledge graph to each other or identify connections between the nodes to recognize the user's current state and its surrounding environment. The electronic device may selectively execute one or more functions among a plurality of functions that can be provided by the electronic device, based on the recognized current state of the user and its surrounding environment. For example, the electronic device may include a function independent of the body part used by the user in the current state among the user's body parts.

Hereinafter, an operation performed by the electronic device based on a body part used by a user in a cleaning state according to an embodiment will be described in detail with further reference to FIGS. 16 to 17.

Figure 16:
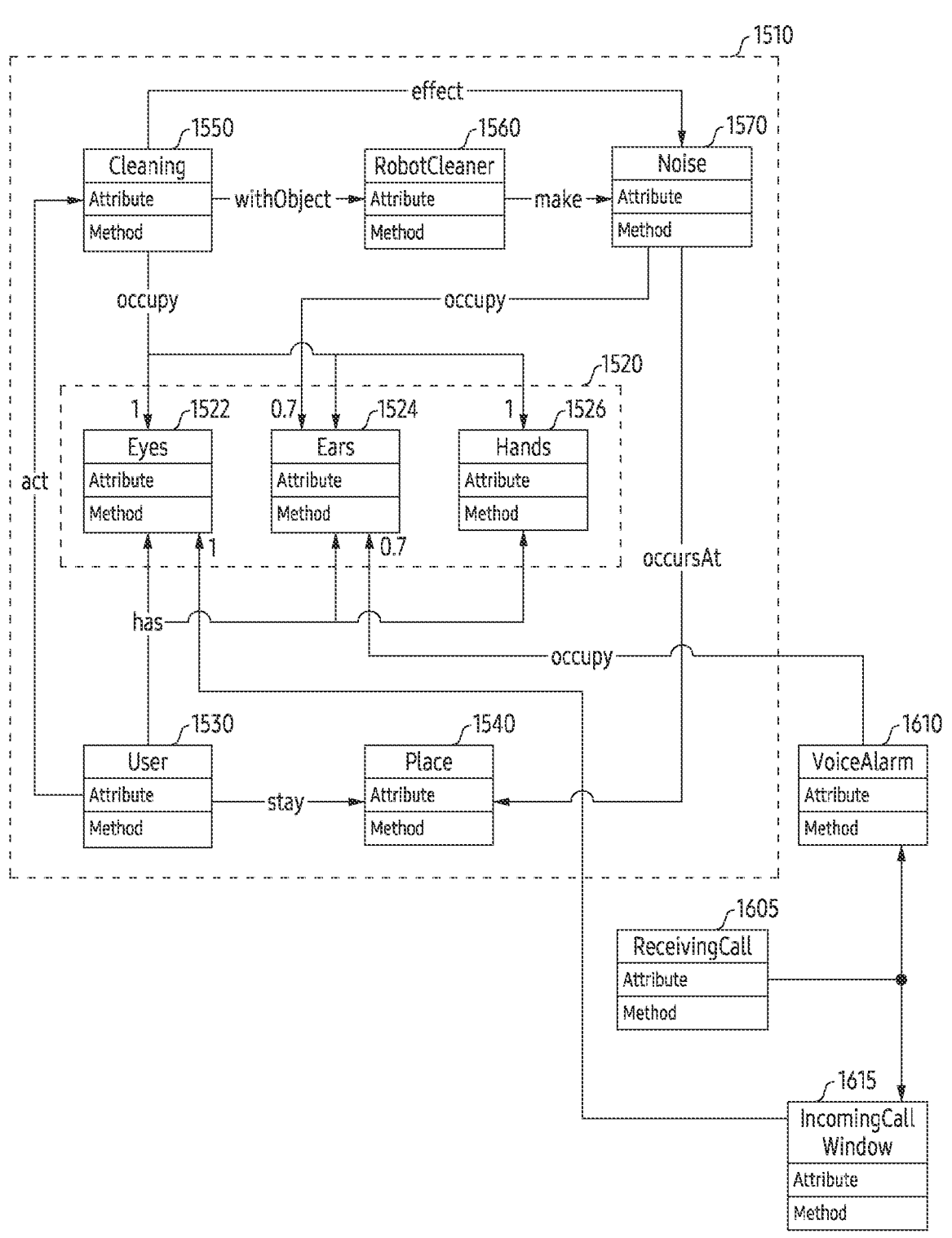
FIG. 16 is a diagram illustrating an operation of an electronic device identifying a user's state and another state related to an event, based on a knowledge graph, according to an embodiment.

FIG. 16 is an exemplary diagram for explaining an operation in which an electronic device identifies a user's state and another state related to an event, based on a knowledge graph, according to an embodiment. The electronic device of FIG. 16 may include the electronic devices 101-1, 101-2, 101-3 and 101-4 of FIG. 1 and/or the electronic device 101 of FIG. 2. A portion 1510 of the knowledge graph of FIG. 16 may correspond to a portion 1510 of the knowledge graph of FIG. 15. Hereinafter, in response to identifying that the user's current state corresponds to a cleaning state, description will be made to an operation that the electronic device, according to an embodiment, performs in a state that the plurality of nodes 1522, 1524, 1526, 1530, 1540, 1550, 1560 and 1570 are connected to each other based on the user's current state in the knowledge graph, such as the portion 1510 of the knowledge graph.

In a state that the user is cleaning, the electronic device, according to an embodiment, may detect occurrence of an event for executing a function related to another state (e.g., a state of receiving an incoming call) distinguished from the state of the user, such as an incoming call. For example, in response to receiving a signal indicating an incoming call from an external electronic device, the electronic device, according to an embodiment, may detect occurrence of an event for executing a function related to the state of receiving an incoming call (e.g., the operation 1210 of FIG. 12). In response to detecting the occurrence of the event, the electronic device, according to an embodiment, may identify a function to be executed in response to the event, in the knowledge graph.

Referring to FIG. 16, in response to detecting the event of receiving an incoming call, the electronic device may identify the node 1605 indicating a state related to the event (e.g., a state of notifying an incoming call) in the knowledge graph. For example, the node 1605 may be connected with the nodes 1610 and 1615 corresponding to distinct states to notify the incoming call. The electronic device, according to an embodiment, may compare the body part associated with the nodes 1610 and 1615 with the body part associated with the node 1550 corresponding to the user's current state to determine whether to execute a function corresponding to which state of states corresponding to each of the nodes 1610 and 1615.

For example, the node 1610 may correspond to a state of notifying the user of an incoming call using a voice alarm. For example, the node 1615 may respond to a state of notifying the user of an incoming call using a notifying window displayed on a display (e.g., a display 240 of FIG. 2). Using the nodes 1610 and 1615 connected to the node 1605, the electronic device may identify a plurality of functions available for notifying the user of the incoming call. The electronic device, according to an embodiment, may selectively execute a function independent of the action related to the user's current state among the plurality of states.

For example, the node 1615 corresponding to a state notifying an incoming call to the user using the notifying window may be connected to the node 1522 connected, based on a predetermined intensity indicating exclusive use, with the node 1550 corresponding to the current state. Based on the connection between the nodes 1615, 1522 and 1550, the electronic device may recognize that displaying the notifying window requires using of the eyes, which is a body part exclusively used in the user's current state. For example, the electronic device may recognize that the user in cleaning action will have to at least temporarily cease the cleaning action in order to gaze at the notifying window. The electronic device, according to an embodiment, may select and execute another function of notifying an incoming call, without displaying such a notifying window, which is a function requiring use of the eye that is a body part exclusively used in the user's current state.

For example, the node 1610 corresponding to the state of notifying an incoming call to a user using a voice alarm may be connected to the node 1524 connected based on intensity indicating partial use with the node 1550 corresponding to the current state. Based on the connection between the nodes 1610, 1524 and 1550, the electronic device may recognize that the user in cleaning can hear a voice alarm without stopping the cleaning. The electronic device, according to an embodiment, may control a function corresponding to distinct states requiring the body part, based on the usage of the partly available body part. For example, since both the node 1550 corresponding to the current state of the user and the node 1610 corresponding to the state of notifying the user of an incoming call using the voice alarm are connected to the node 1524 associated with the ear, the electronic device may recognize that the state of cleaning and the state of receiving the voice alarm may cause interference with each other. For example, the electronic device may recognize the fact that it is difficult for the user in cleaning to hear a sound by the voice alarm, based on the nodes 1550 and 1610 connected to the node 1524 in the knowledge graph.

Hereinafter, with reference to FIG. 17, description will be made to an exemplary operation performed by the electronic device, according to an embodiment, in which the priority of the event-related state (e.g., the state of notifying the user of an incoming call using a voice alarm) is higher than that of the user's current state (e.g., the cleaning state), and in a state that the electronic device recognizes the interference between the two states, as discussed above.

Figure 17:
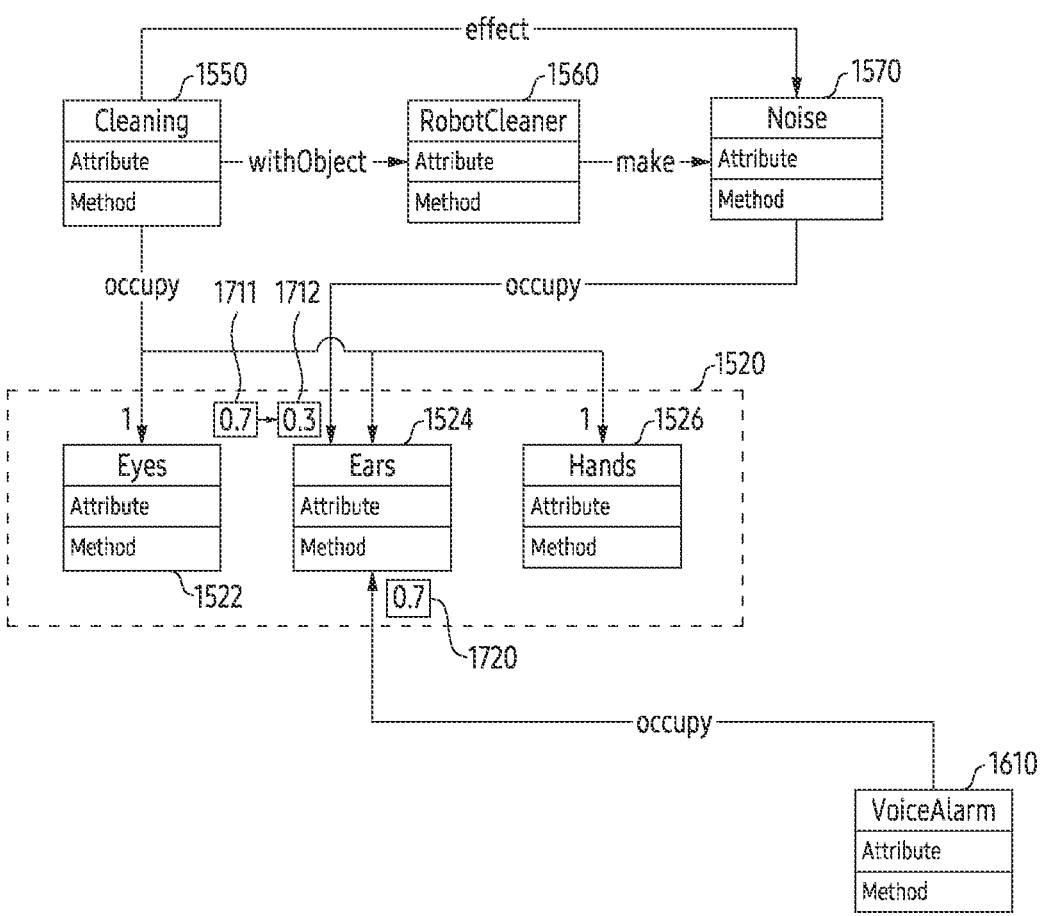
FIG. 17 is a diagram illustrating an operation of an electronic device controlling a mode of the electronic device related to a user's state, based on a knowledge graph, according to an embodiment.

FIG. 17 is an exemplary diagram for explaining an operation of an electronic device for controlling a mode of the electronic device related to a user's state, based on a knowledge graph, according to an embodiment. The electronic device of FIG. 17 may include the electronic devices 101-1, 101-2, 101-3 and 101-4 of FIG. 1 and/or the electronic device 101 of FIG. 2. A portion of the knowledge graph of FIG. 17 may correspond to a portion 1510 of the knowledge graph of FIGS. 15 to 16.

The electronic device, according to an embodiment, may perform an operation (e.g., the operations 1262 and 1264 of FIG. 12) for mitigating the interference onto body parts generated by the user who simultaneously performs actions related to each of two distinct states. For example, based on the node 1524 connected to both the node 1550 corresponding to the cleaning state of the user and the node 1610 corresponding to the state in which the user is receiving a voice alarm, the electronic device may determine that the interference occurs in the ears, which is a body part corresponding to the node 1524. For example, the electronic device may recognize that it is difficult for the user in cleaning to hear a sound from the voice alarm.

The electronic device, according to an embodiment, may execute a function to adjust the intensity in between the node corresponding to a body part related to the interference and another node in a knowledge graph, in order to mitigate the interference by at least one body part of the user. Referring to FIG. 17, the electronic device, according to an embodiment, may identify the intensities 1711 and 1720 between the node 1524 corresponding to the body part related to the interference and the nodes 1550 and 1610 corresponding to each of two distinct states. For example, it is assumed that the intensity 1711 between the node 1550 corresponding to the cleaning state and the node 1524 corresponding to the ear is '0.7', and the intensity between the node 1610 corresponding to the state of outputting the voice alarm and the node 1524 corresponding to the ears is '0.7'. When the user's current state corresponds to both the two distinct states, the electronic device, according to an embodiment, may identify overusing of the body part, by using a sum of the intensities 1711 and 1720 between the node 1524 corresponding to the body part related to both the two states and the nodes 1550 and 1610 corresponding to each of the two states. For example, since the sum (e.g., '1.4') of the intensities 1711 and 1720 exceeds a predetermined threshold (e.g., '1'), the electronic device may identify ear overusing of the ears as the user hears the voice alarm while cleaning.

In response to identification of the overusing, the electronic device, according to an embodiment, may execute a function to reduce the intensity (e.g., the intensities 1711 and 1720) related to the body part related to the overusing. In the above example, in response to identifying the user's ear overusing, the electronic device may execute the function to reduce the intensity of the voice alarm and/or reduce noise generated by the robot cleaner.

The electronic device, according to an embodiment, may execute a function for reducing intensity associated with a state having a relatively low priority. For example, when the priority of the cleaning state indicated by the node 1550 is lower than the priority of the state of receiving the voice alarm indicated by the node 1610, the electronic device may execute a function to reduce the intensity 1711 associated with the node 1550. For example, the electronic device may execute the function to reduce the intensity 1711 by a difference (e.g., '0.4') between the sum (e.g., '1.4') of the intensities 1711 and 1720 and a predetermined threshold (e.g., '1'). For example, the predetermined threshold may be a threshold value indicating overusing of a body part. In an embodiment, the adjustment of the intensity 1711 by the electronic device may be performed within a range in between a minimum intensity value (e.g., a value indicating that a body part is not used at all, such as '0') and a maximum intensity value (e.g., a value meaning an exclusive use of a body part, such as '1').

The electronic device, according to an embodiment, may execute a function for reducing overusing of a body part in the state, based on the attributes of the node 1550 corresponding to the state having a relatively low priority. For example, based on the attributes of the node 1550, the electronic device may execute a function of switching the mode of the robot cleaner to a silent mode, so as to reduce the intensity 1711 corresponding to the body part (e.g., ears) associated with all the distinct states. For example, in response to the operation mode of the robot cleaner being switched to the silent mode, the electronic device may reduce the intensity 1711 between the node 1550 corresponding to the state having a relatively low priority and the node 1550 corresponding to the body part associated with all the distinct states, to the intensity 1712. Reducing the intensity between the nodes 1524 and 1550 can prevent overusing of the body part corresponding to the node 1524.

As described above, when a plurality of actions each corresponding to the current state and another state by an event are simultaneously generated by the user, the electronic device may control at least one of the first function related to the current state or the second function related to the other state to prevent overusing of the body part by both the current state and the other state. Prevention of overusing may be performed as the electronic device executes at least one function using the knowledge graph indicating both the user's actions classified according to states and the usages of the body parts by the actions. For example, the electronic device may adjust a function and/or a mode corresponding to a state having a lower priority of the current state and the other states, so as to adjust the sum of the intensities assigned to the node corresponding to the body part related to both the current state and the other state in the knowledge graph. The adjustment of the sum of the intensities may be performed by the electronic device in response to generating a command to adjust the function and/or the mode related to the current state and/or the other state. The generation of the command may be performed based on a look-up table indicating a relationship between the command and the intensity.

Figure 18:
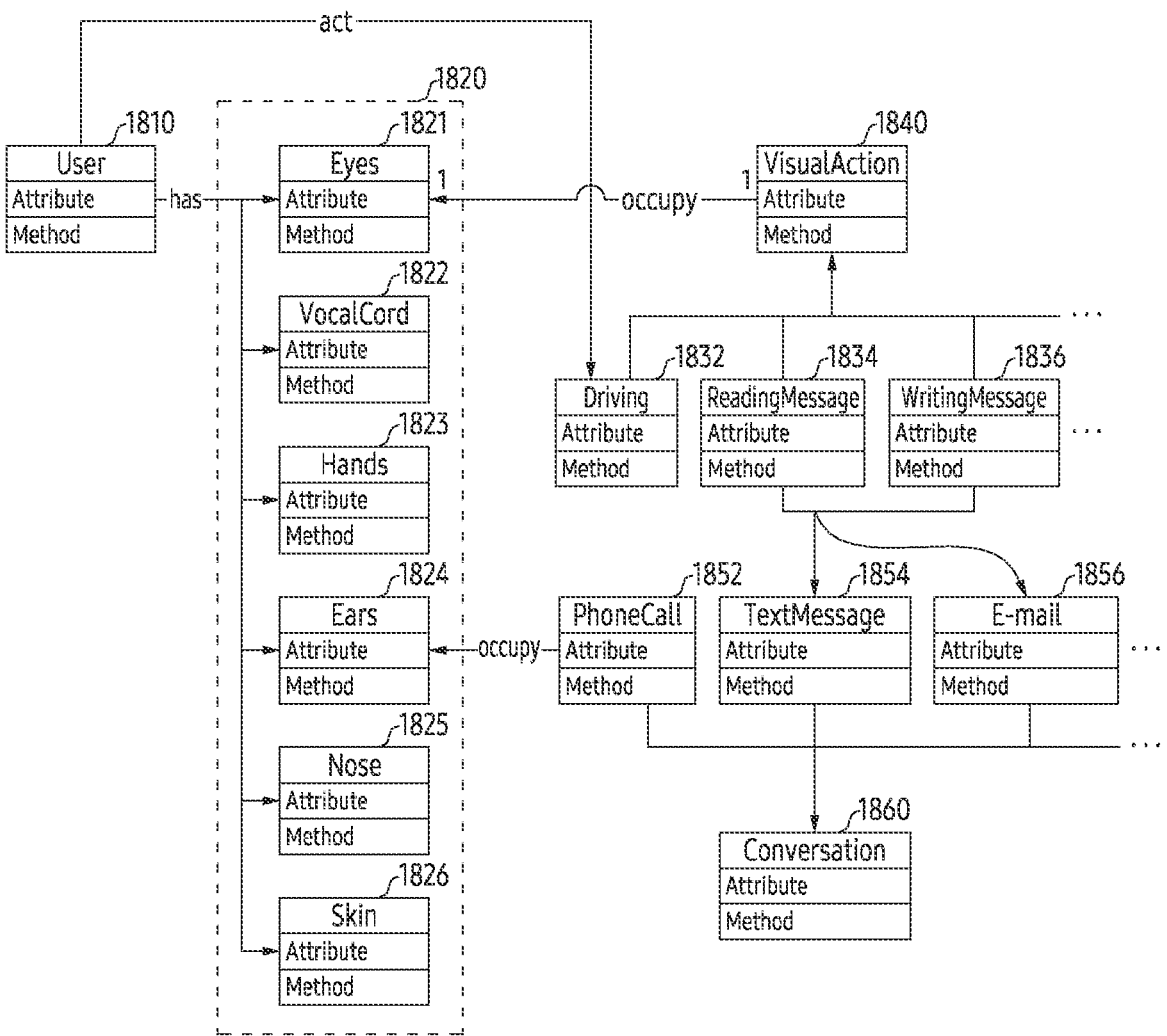
FIG. 18 is a diagram illustrating an operation of an electronic device selecting and executing any one function of a plurality of functions, based on a knowledge graph, according to an embodiment.

FIG. 18 is an exemplary diagram for describing an operation of an electronic device selecting and executing any one of a plurality of functions based on a knowledge graph, according to an embodiment. The electronic device of FIG. 18 may include the electronic devices 101-1, 101-2, 101-3 and 101-4 of FIG. 1 and/or the electronic device 101 of FIG. 2. The knowledge graph of FIG. 18 may correspond to at least a portion of the knowledge graphs 121, 121-1, 121-2, 122, 123 and 124 of FIG. 1 and the knowledge graph 120 of FIG. 2.

The electronic device, according to an embodiment, may identify the current state of the user, for example, by performing at least one of the operations 310 and 320 of FIG. 3. For example, when the user drives a vehicle, the electronic device corresponding to a user terminal (e.g., an electronic device 101-1 of FIG. 1) may identify that a current state of the user corresponds to a driving state, at least based on communication between the electronic device and an electronic control unit (ECU) of the vehicle and/or a change in the location detected by the electronic device. In response to identifying that the current state of the user corresponds to the driving state, the electronic device, according to an embodiment, may connect a node 1832 corresponding to the driving state and a node 1810 corresponding to the user to each other, in the knowledge graph. Referring to FIG. 18, the electronic device may assign a specified parameter (e.g., act) indicating the current state and performing of its related action to a connection between the nodes 1832 and 1810.

The electronic device, according to an embodiment, may minimize the interference by the user's action, based on the user's action in the current state and the usage of the body part using the knowledge graph. For example, when an external electronic device distinct from the electronic device has received a user input (e.g., "send a text to the user") for communicating with the user of the electronic device, from another user distinct from the user, the external electronic device may transmit to the electronic device a signal requesting exchanging of the text message between the user and the other user. In response to receiving the signal, the electronic device may execute a function for maintaining an action based on the user's current state (e.g., driving state).

In response to receiving the signal, the electronic device, according to an embodiment, may detect occurrence of an event related to a state distinct from the current state of the user in driving (e.g., the state of sending a text message to another user and/or receiving a text message from another user). Detecting the occurrence of the event by the electronic device may be performed, for example, based on the operation 1210 of FIG. 12. The electronic device may identify one or more nodes corresponding to the state related to the event, in the knowledge graph. Referring to FIG. 12, the electronic device may identify a node 1834 corresponding to a state of reading a text message and a node 1836 corresponding to a state of writing a text message.

The electronic device, according to an embodiment, may identify the body part related to both the state related to the event and the current state of the user, based on one or more nodes corresponding to the state related to the event. Identification of the body part related to both the state related to the event and the current state of the user by the electronic device may be, for example, related to the operation 1220 of FIG. 12. Referring to FIG. 18, the nodes 1834 and 1836 corresponding to the state related to the event may be connected to the node 1840 corresponding to a state of performing a visual action, similarly to the node 1832 corresponding to the current state. The node 1840 may be connected to the node 1821 corresponding to an eye of the nodes 1821, 1822, 1823, 1824, 1825 and 1826 included in the class 1820 related to the body parts. Referring to FIG. 18, a connection between the nodes 1821 and 1840 may have a predetermined intensity indicating exclusive use of the body part. The electronic device, according to an embodiment, may identify that all of the nodes 1834 and 1836 corresponding to the state related to the event and the node 1832 corresponding to the current state are connected to the node 1821 corresponding to the eye via the node 1840. For example, since the user uses his/her eyes to drive a vehicle, the electronic device may recognize that he/she has to at least temporarily stop driving to stare at the text message, based on the connection between the node 1821 corresponding to the eye and the node 1834, 1836 and 1832.

In response to identifying the body part related to both the state associated with the event and the current state of the user, the electronic device, according to an embodiment, may identify one or more candidate states for replacing the state associated with the event. Identifying the candidate state by the electronic device may, for example, be related to the operation 1230 of FIG. 12. Referring to FIG. 18, in response to identifying that all the nodes 1834 and 1836 corresponding to the state related to the event and the node 1832 corresponding to the current state are connected to the node 1821 corresponding to the eye via the node 1840 (e.g., 'YES' in operation 1220 of FIG. 12), the electronic device may identify the candidate state distinguished from the state related to the event in the knowledge graph. Referring to FIG. 18, the nodes 1834 and 1836 corresponding to the state related to the event may be connected to the node 1854 corresponding to a state related to a text message and the node 1856 corresponding to a state related to an e-mail, and the nodes 1854 and 1856 may be connected to the node 1860 corresponding to a state related to a conversation, along with the node 1852 corresponding to a state related to a phone call. Referring to FIG. 18, the electronic device, according to an embodiment, may search for other nodes 1854, 1856, 1860 and 1852 connected to the nodes 1834 and 1836 corresponding to the state related to the event in the knowledge graph to identify the node 1852 corresponding to the state related to a phone call as the candidate state.

In response to identifying the one or more candidate states, the electronic device, according to an embodiment, may identify a candidate state associated with another body part distinguished from one or more body parts associated with the current state of the user among the identified candidate states. Identification of the candidate state related to the other body part by the electronic device may be, for example, related to the operation 1240 of FIG. 12. Referring to FIG. 18, in response to identifying the state related to a phone call as the candidate state, the electronic device, according to an embodiment, may identify the node 1824 included in the class 1820 related to the body part among other nodes connected to the node 1852 corresponding to the candidate state. Based on the fact that the node 1852 and the node 1824 corresponding to the candidate state are connected to each other and the node 1832 corresponding to the current state is not connected with the node 1824, the electronic device may determine that the candidate state (e.g., a state related to a phone call) corresponding to the node 1852 is related to another body part distinct from one or more body parts associated with the current state.

In response to identifying the candidate state related to other body part distinct from one or more body parts associated with the current state of the user, the electronic device, according to an embodiment, may at least temporarily cease executing the function associated with the event and execute other function corresponding to the candidate state. Executing the other function corresponding to the candidate state by the electronic device may be, for example, related to the operation 1245 of FIG. 12. Referring to FIG. 18, since the node 1852 corresponding to the candidate state is connected to the node 1824 corresponding to the ear and not connected to the node 1821 corresponding to the eye, which is the body part related to the current state, the electronic device may execute a function related to a phone call that is a candidate state. For example, when an external electronic device transmits a signal requesting exchanging of a text message between the user and the other user to the electronic device, the electronic device may transmit a signal recommending establishment of a call connection, not the text message, to the external electronic device. The external electronic device may recommend establishment of a call connection to other user, in response to receiving the signal recommending establishment of the call connection. In response to the other user requesting the external electronic device to establish a call connection, the external electronic device may transmit to the electronic device a signal to request establishment of the call connection.

As described above, the electronic device may prevent occurrence of an action obstructing the user's looking ahead while driving, such as exchanging a text message. For example, if the node 1852 corresponding to the candidate state does not exist in the knowledge graph, then the electronic device may further perform an operation to determine the priority of the driving state and the state of exchanging text messages (e.g., the operation 1250 of FIG. 12). When the priority of the state of exchanging text messages is higher than the priority of the driving state, the electronic device may allow the user to execute a function related to the state of exchanging text messages. As in the example above, the electronic device, according to an embodiment, may determine execution of a function that prevents an action related to the user's current state, based on the priority.

The electronic device, according to an embodiment, may compare the knowledge graphs of a plurality of users to recognize a state related to the plurality of users. Hereinafter, an operation of the electronic device recognizing a state common to the plurality of users will be described with further reference to FIGS. 19 to 21.

Figure 19:
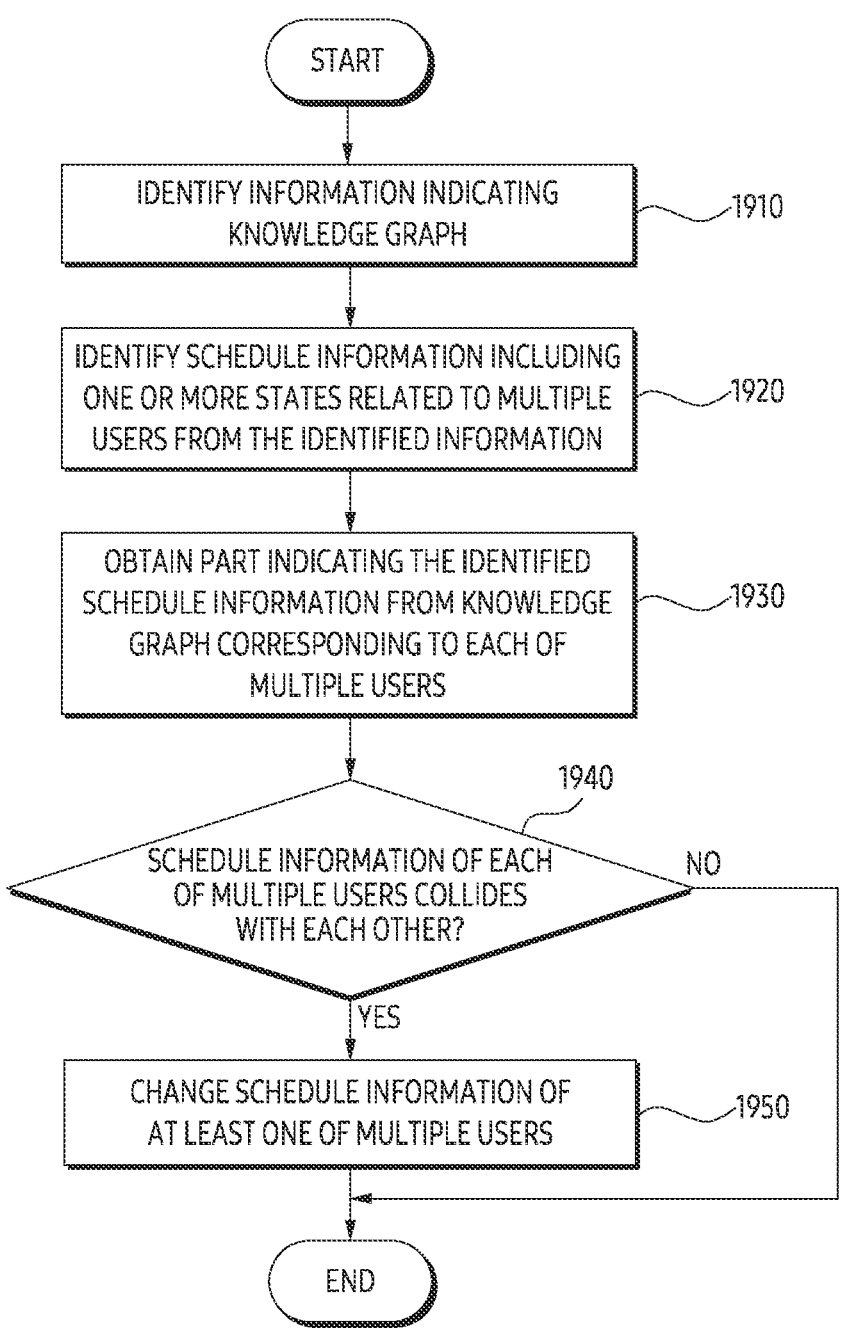
FIG. 19 is a flowchart illustrating an operation performed by an electronic device based on a knowledge graph of a plurality of users, according to an embodiment.

FIG. 19 is a flowchart illustrating an operation performed by an electronic device based on a knowledge graph of a plurality of users, according to an embodiment. The electronic device of FIG. 19 may include the electronic devices 101-1, 101-2, 101-3 and 101-4 of FIG. 1 and/or the electronic device 101 of FIG. 2. The operation of FIG. 19 may be, for example, performed in an electronic device (e.g., an electronic device 101-1 of FIG. 1) corresponding to a server connected to user terminals of a plurality of users, and/or may be performed by each of the user terminals of the plurality of users. The operation of FIG. 19 may be performed by the electronic device 101 of FIG. 2 and/or the processor 210 of FIG. 2.

Referring to FIG. 19, in operation 1910, the electronic device, according to an embodiment, may identify information indicating the knowledge graph. For example, the electronic device may obtain information indicating a knowledge graph personalized for each of one or more users from a memory (e.g., a memory 220 of FIG. 2). For example, the electronic device 101-1 of FIG. 1 may be a server that provides a service to a plurality of subscribers, and may identify the knowledge graph (e.g., at least one knowledge graph of the knowledge graphs 121-1 and 121-2 of FIG. 1) personalized to at least one user of the plurality of subscribers. For example, the electronic device 101-2 of FIG. 1 may identify a knowledge graph (e.g., a knowledge graph 122 of FIG. 1) personalized to a user, with a user terminal of a user.

Referring to FIG. 19, in operation 1920, the electronic device, according to an embodiment, may identify schedule information including one or more states related to a plurality of users from the identified information. The electronic device, according to an embodiment, may identify one or more nodes indicating schedule information common to the plurality of users, in the knowledge graph indicated by the information identified based on the operation 1910. For example, in the knowledge graph identified by the electronic device, the user's schedule information may be identified from a node based on a class indicating the user's daily routine, such as the node 440 of FIG. 4. The schedule information may be stored in the knowledge graph by a user input received by the electronic device based on a specified application (e.g., a schedule application). In response to identifying the plurality of users from the identified schedule information, the electronic device, according to an embodiment, may perform operation 1930.

Referring to FIG. 19, in operation 1930, the electronic device, according to an embodiment, may obtain part indicating the identified schedule information from a knowledge graph corresponding to each of the plurality of users. For example, in response to identification of the schedule information related to the plurality of users, the electronic device 101-1 of FIG. 1 may obtain one or more nodes related to the schedule information, from the knowledge graph of each of the plurality of users related to the schedule information. For example, in response to identification of the schedule information related to the plurality of users, the electronic device 101-2 of FIG. 1 may transmit a signal requesting a portion of the knowledge graph related to the schedule information, to an external electronic device of at least one user of the plurality of users. A portion of the knowledge graph obtained by the electronic device may indicate the schedule information input by the user corresponding to the portion.

Referring to FIG. 19, in operation 1940, the electronic device, according to an embodiment, may determine whether the schedule information of each of a plurality of users collides with each other. In response to obtaining the portion of the knowledge graph in the operation 1930, the electronic device, according to an embodiment, may compare classes and/or attributes of one or more nodes included in the obtained portion to identify collision and/or discrepancy in schedule information. When the plurality of users respectively input inconsistent schedule information for the schedule related to the plurality of users, such collision and/or inconsistency in schedule information may occur. When the schedule information of each of the plurality of users does not collide with each other ('NO' in the operation 1940), the electronic device may maintain the schedule information of each of the plurality of users.

When the schedule information of each of a plurality of users collides with each other ('YES' in the operation 1940), in operation 1950, the electronic device, according to an embodiment, may change the schedule information of at least one of the plurality of users. For example, in response to identifying the collision and/or inconsistency in the schedule information, the electronic device may display a UI requesting change of the schedule information from at least one of the plurality of users. In response to obtaining a user input related to the displayed UI, the electronic device may change the schedule information. Changing of the schedule information may include changing the connection and/or attributes between one or more nodes corresponding to the schedule information in the knowledge graph.

Hereinafter, an example in which the electronic device, according to an embodiment, performs at least one of the operations of FIG. 19 will be described in detail with further reference to FIGS. 20 to 21.

Figure 20:
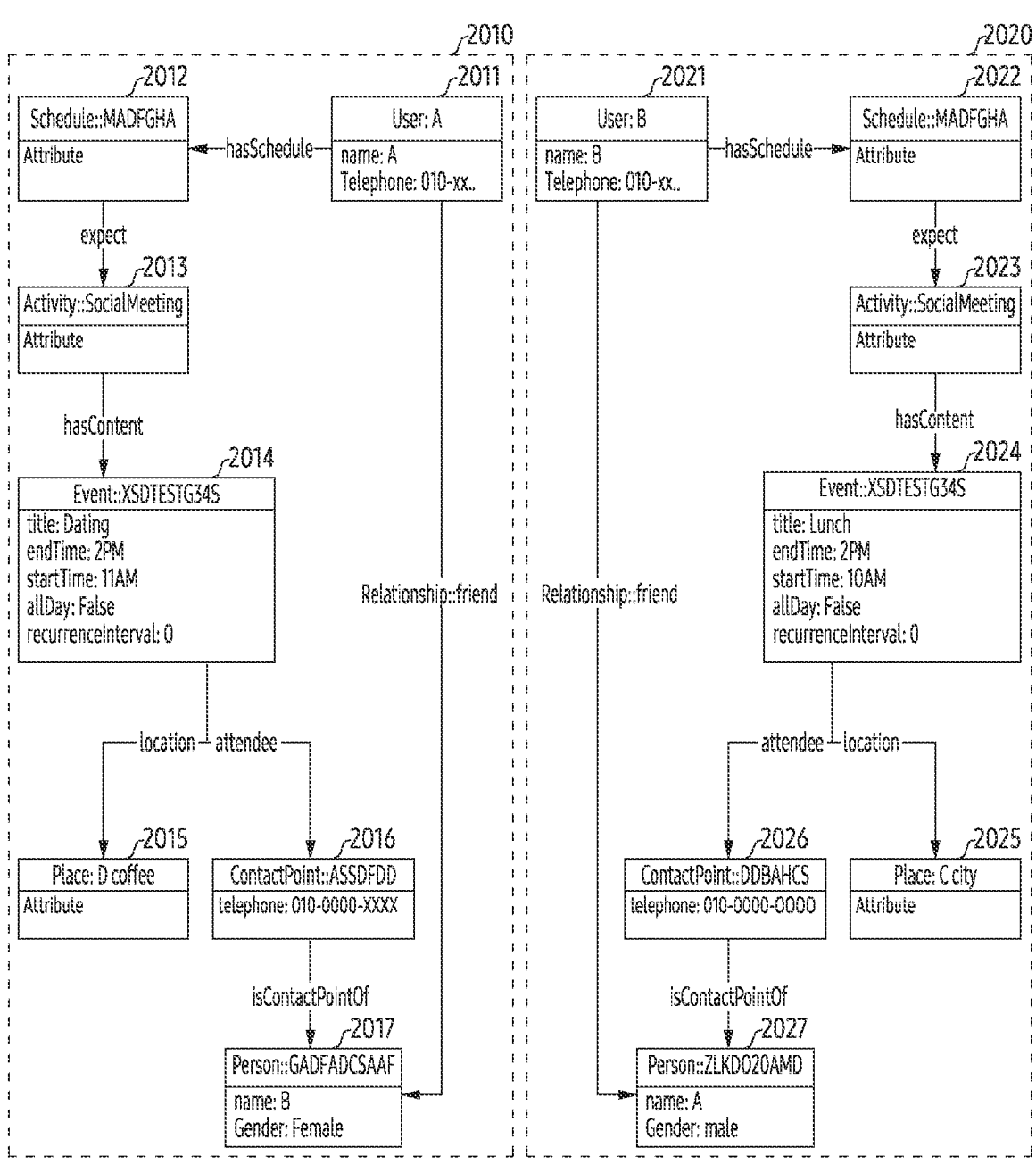
FIG. 20 is a diagram illustrating an operation of comparing, by an electronic device, a portion of a knowledge graph corresponding to each of a plurality of users, according to an embodiment.

FIG. 20 is an exemplary diagram for explaining an operation in which an electronic device, according to an embodiment, compares portions 2010 and 2020 of a knowledge graph corresponding to each of a plurality of users. The electronic device of FIG. 20 may include the electronic devices 101-1, 101-2, 101-3 and 101-4 of FIG. 1 and/or the electronic device 101 of FIG. 2.

Referring to FIG. 20, there are illustrated the portions 2010 and 2020 obtained by the electronic device, according to an embodiment, from knowledge graphs personalized for each of a plurality of users. For example, in response to identifying the schedule information common to the plurality of users based on the operations 1910, 1920 and 1930 of FIG. 19, the electronic device may obtain the portions 2010 and 2020 corresponding to the schedule information from the knowledge graph of each of the plurality of users. Referring to FIG. 20, the electronic device, according to an embodiment, may search for a plurality of nodes connected to a node 2011 corresponding to the user, in the portion 2010 of the knowledge graph related to a user A.

For example, in response to identifying the node 2012 based on the class related to the schedule information, the electronic device, according to an embodiment, may identify the schedule corresponding to the node 2012 is related to another user distinct from the user A, based on the attributes of the node 2012 and/or one or more other nodes 2013, 2014, 2015, and 2016 connected to the node 2012. For example, in response to identifying a type (e.g., date) indicated in the attributes of the node 2014 connected to the node 2012 indicating the schedule and/or a node 2017 based on a class indicating a person, the electronic device, according to an embodiment, may determine that the schedule associated with the node 2012 is related to both the user A and other user. For example, the electronic device that identified a user B from the attributes of the node 2017 may obtain the portion 2020 of the knowledge graph corresponding to the user B.

Referring to FIG. 20, the portion 2020 of a knowledge graph obtained by the electronic device may include a plurality of nodes 2023, 2024, 2025, 2026, and 2027 connected to the node 2022 related to the schedule information of a plurality of nodes connected to the node 2021 corresponding to the user B. The electronic device, according to an embodiment, may compare the schedule common to the plurality of users based on the knowledge graph to determine whether the schedules input by each of the plurality of users conflict with each other. For example, based on the operation 1940 of FIG. 19, the electronic device may identify the collision and/or discrepancy in the schedules obtained from each of the users and stored in the knowledge graph corresponding to each of the users.

Referring to FIG. 20, the electronic device, according to an embodiment, may identify the schedules related to the nodes 2012 and 2022 as the schedule common to the user A and the user B corresponding to the nodes 2011 and 2022, respectively. The electronic device, according to an embodiment, may compare the class and/or attributes of a plurality of nodes 2013, 2014, 2015, 2016, 2017, 2023, 2024, 2025, 2026 and 2027 connected to each of the nodes 2012 and 2022 corresponding to the schedule in each of the portions 2010 and 2020 of the knowledge graph to determine whether the schedules recognized from each of the portions 2010 and 2020 of the knowledge graph collide with each other. When the schedules recognized from each of the portions 2010 and 2020 of the knowledge graph collide with each other, it may imply that the user A and the user B corresponding to each of the portions 2010 and 2020 recognize the common schedule differently from each other.

Referring to FIG. 20, the electronic device, according to an embodiment, may identify a discrepancy in the starting time (e.g., startTime) of the schedule indicated by the attributes of each of the nodes 2014 and 2024 and the location (e.g., place) of the schedule indicated by the attributes of each of the nodes 2015 and 2025. In response to identifying the discrepancy, the electronic device may change at least part of the schedule information, for example, based on the operation 1950 of FIG. 19. For example, the electronic device may provide each of the user A and the user B with a UI for changing schedule information related to the nodes 2012 and 2022. In an embodiment where the electronic device corresponds to the electronic device 101-1 of FIG. 1, the electronic device may request at least one user terminal of the user A and the user B to display the UI for changing schedule information. In an embodiment where the electronic device corresponds to the user terminal of the user A (e.g., an electronic device 101-2 in FIG. 1), the electronic device may display the UI for changing the schedule information related to the node 2012 on a display (e.g., a display 240 in FIG. 2), and/or transmit a signal requesting updating of the schedule information, to an external electronic device related to the user B.

Comparing the portions 2010 and 2020 of the knowledge graph by the electronic device, according to an embodiment, may be performed based on a portion of the memory (e.g., a memory 220 of FIG. 2) for temporarily storing information related to the knowledge graph. For example, after the user's completing the change in at least part of the schedule information, based on the UI for changing the schedule information, the electronic device, according to an embodiment, may delete the portions 2010 and 2020 stored in a part of the memory.

As described above, the electronic device, according to an embodiment, may recognize the schedule common to a plurality of users using the knowledge graph. The electronic device may identify discrepancy included in the schedule common to the plurality of users based on the recognized schedule. The electronic device may provide a UI based on the identified discrepancy to the user to assist in resolving the discrepancy included in the schedule common to the plurality of users. For example, the electronic device may get rid of the discrepancies included in the schedule common to the plurality of users. The electronic device, according to an embodiment, may protect the privacy of users corresponding to each of the portions 2010 and 2020 by extracting and comparing only the portions 2010 and 2020 of the knowledge graph.

Figure 21:
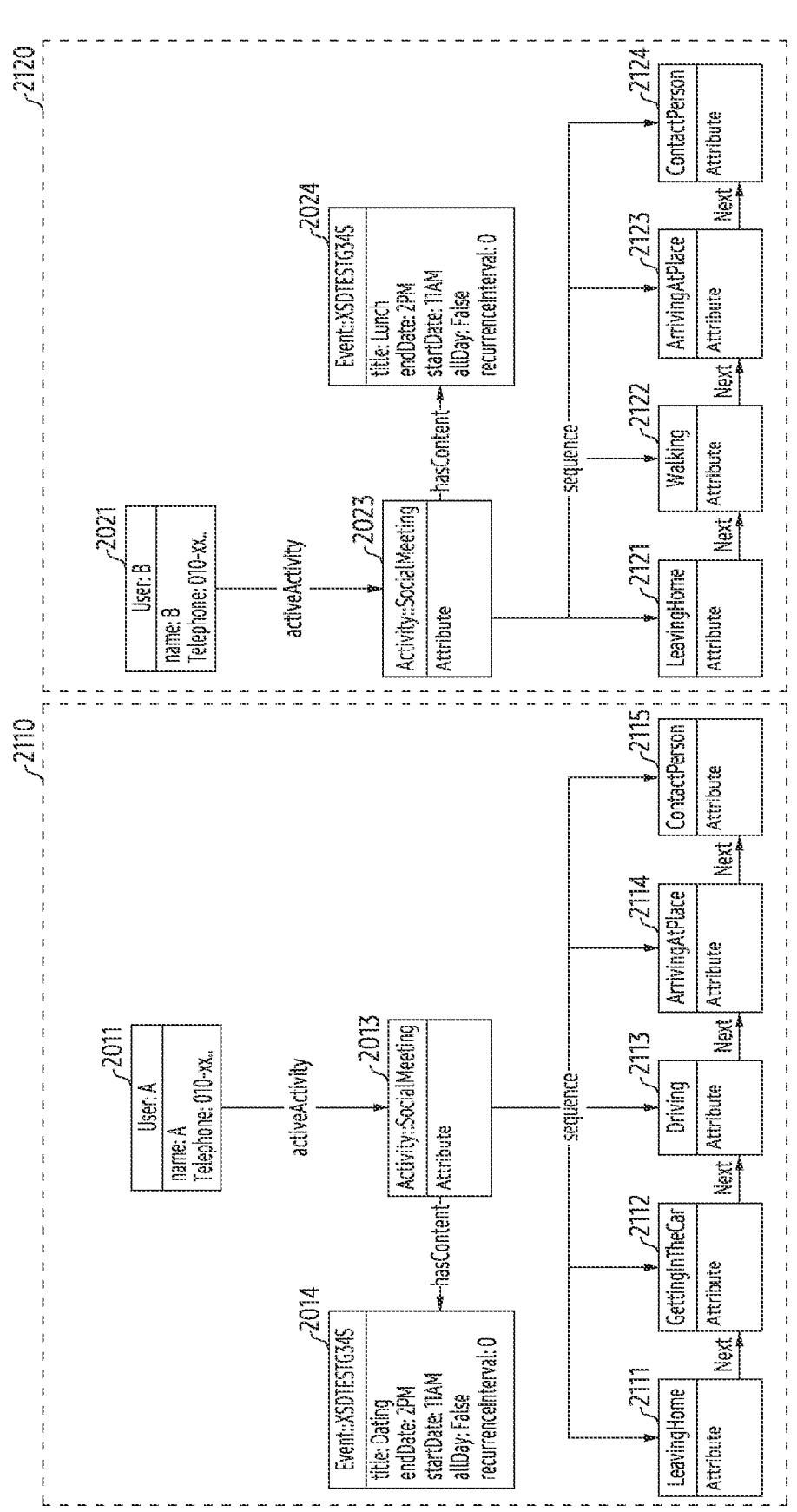
FIG. 21 is a diagram illustrating an operation of an electronic device identifying one or more states for a common schedule in between a plurality of users, based on a knowledge graph, according to an embodiment.

FIG. 21 is an exemplary diagram for describing an operation of an electronic device, according to an embodiment, identifying one or more states for a schedule common in between a plurality of users, based on a knowledge graph. The electronic device of FIG. 21 may include the electronic devices 101-1, 101-2, 101-3 and 101-4 of FIG. 1 and/or the electronic device 101 of FIG. 2. Hereinafter, description will be made of an operation performed by the electronic device, according to an embodiment, while the states of a plurality of users related to the common schedule information in FIG. 20 may correspond to the states related to the schedule information. The electronic device corresponds to a server that communicates with user terminals of the plurality of users, like the electronic device 101-1 of FIG. 1, and/or may correspond to any one of the user terminals of each of the plurality of users, like the electronic device 101-2 of FIG. 1.

The electronic device, according to an embodiment, may identify the portions 2110 and 2120 related to the common schedule, from each of the knowledge graphs personalized for each of the plurality of users performing the common schedule. The electronic device may identify states of the plurality of users performing the common schedule, based on the portions 2110 and 2120. For example, the portion 2110 of the knowledge graph of the user A of the users performing the common schedule may include nodes 2013, 2014, 2111, 2112, 2113, 2114 and 2115 connected to the node 2011 corresponding to the user A and related to the schedule. For example, the portion 2120 of the knowledge graph of the user B of the users may include nodes 2023, 2024, 2121, 2122, 2123 and 2124 connected to the node 2021 corresponding to the user B and related to the schedule.

Based on a sequence of the nodes 2111, 2112, 2113, 2114 and 2115 corresponding to distinct states, the electronic device, according to an embodiment, may identify states respectively corresponding to actions performed in sequence by user A in relation to the schedule. For example, based on the sequence of the nodes 2111, 2112, 2113, 2114 and 2115, the electronic device may identify a change in state from when the user A started going out (e.g., a state of going-out indicated by node 2111) until he/she meets a person (e.g., a state of meeting a person corresponding to the node 2115). Based on the identified change in state, the electronic device may execute a function corresponding to the user's current state.

For example, the user input performed by a user B for the electronic device may include a command for contacting the user A (e.g., a voice command such as, e.g., "contact A"). In response to identifying the command from the user input, the electronic device, according to an embodiment, may identify the current state of the user A using the portion 2110 of the knowledge graph corresponding to the user A. Based on the identified current state of user A, the electronic device may execute a function that does not cease the user A's action related to the current state. For example, based on the sequence of the nodes 2111, 2112, 2113, 2114 and 2115 included in the portion 2110, the electronic device may identify that the user A is driving (e.g., a state corresponding to the node 2113). Since the user A is driving, the electronic device, according to an embodiment, may execute a function (e.g., phone) maintaining the user's action related to the driving (e.g., looking ahead to the front) of functions (e.g., phone call, messaging, and e-mail) that can be provided based on the command.

As described above, the electronic device, according to an embodiment, may identify a state of each of the users, based on the portions 2110 and 2120 of the knowledge graphs of the users performing the common schedule. Using the identified state of the user, the electronic device may selectively execute the function for maintaining the user's action related to the identified state. When the portions 2110 and 2120 of the knowledge graphs are shared between different electronic devices, the entire knowledge graph may not be shared. Thus, as the knowledge graph personalized to a user is not shared in its entirety with other users, privacy protection can be greatly improved.

As described above, the electronic device, according to an embodiment, may use the knowledge graph to identify the usage of a user's body part and/or identify a schedule common to users. Hereinafter, an operation performed by the electronic device, according to an embodiment, based on the user's body part and the entire resource of the electronic device will be described with reference to FIGS. 22 to 25.

FIG. 22 is a flowchart for explaining an operation performed by an electronic device based on a knowledge graph indicating the body part of the user and usage of the resource of the electronic device, according to an embodiment. The electronic device of FIG. 22 may include the electronic devices 101-1, 101-2, 101-3 and 101-4 of FIG. 1 and/or the electronic device 101 of FIG. 2. The operation of the electronic device of FIG. 22 may be performed, for example, by the electronic device 101 and/or the processor 210 of FIG. 2.

Referring to FIG. 22, in operation 2210, the electronic device, according to an embodiment, may obtain information indicating connections between nodes respectively corresponding to the user's distinct states, the body parts, and the resources of the electronic device, based on the knowledge graph. For example, the electronic device may identify the knowledge graph connecting a plurality of states, a plurality of body parts, a plurality of electronic devices, and resources of the electronic device, from a memory (e.g., a memory 220 of FIG. 2). The knowledge graph, similar to the knowledge graph of FIG. 4, may indicate usage of a resource included in the electronic device and/or usage of a body part of the user, based on different classes. The resource of the electronic device may mean the capability for executing functions that can be provided based on hardware and/or software components including the electronic device.

Referring to FIG. 22, in operation 2220, the electronic device, according to an embodiment, may identify one or more nodes connected to the first node corresponding to the first state of the user, from the obtained information. In the knowledge graph indicated by the information obtained in the operation 2210, the electronic device, according to an embodiment, may identify the one or more nodes connected to the first node. The electronic device, according to an embodiment, may, for example, perform at least one of the operations of FIG. 8 to identify the first node corresponding to the first state of the user. In the knowledge graph, the first node may be a node corresponding to the first state of distinct states.

Referring to FIG. 22, in operation 2230, the electronic device, according to an embodiment, may detect occurrence of an event for executing a function related to a second state distinct from the first state of the user. In an embodiment, the event may be detected by at least one of an application in execution in the electronic device (e.g., an alarm application), a signal received from an external electronic device distinct from the electronic device (e.g., a signal requesting establishment of a call connection), or the user's action detected by the electronic device.

Referring to FIG. 22, in operation 2240, the electronic device, according to an embodiment, may identify one or more nodes connected to the second node corresponding to the second state, from the obtained information. For example, in response to detecting the occurrence of the event in the operation 2230, the electronic device may search the knowledge graph in the operation 2210 based on the second node related to the event to identify one or more nodes connected to the second node. After the occurrence of the event, the electronic device, according to an embodiment, may identify the one or more nodes connected to the second node related to the second state to predict the usage of the user's body part and/or the resource of the electronic device in the second state. Based on a result of predicting the usage of the user's body part and/or the resource of the electronic device in the second state, the electronic device, according to an embodiment, may selectively execute at least one function of a plurality of functions that can be provided by the electronic device.

Referring to FIG. 22, in operation 2250, the electronic device, according to an embodiment, may compare one or more nodes connected to the first node identified in the operation 2220 and one or more nodes connected to the second node identified in the operation 2240. For example, the electronic device may determine whether a node connected in common to the first node and the second node exists among the nodes respectively corresponding to the body parts and the resource of the electronic device. In response to identifying the node connected in common to the first node and the second node, the electronic device may perform an operation related to the node connected in common to the first node and the second node. The electronic device, according to an embodiment, may identify an intersection of a first set including one or more nodes connected to the first node identified in the operation 2220 and a second set including one or more nodes connected to the second node identified in the operation 2240. The node connected in common to the first node and the second node may indicate that the body part and/or the resource of the electronic device corresponding to the node are related to both the first state and the second state.

Based on a result of comparing the one or more nodes connected to the first node and the one or more nodes connected to the second node, in operation 2260, the electronic device may determine whether a body part and/or a resource of the electronic device commonly used in the first state and the second state exists. When there is the body part and/or the resource of the electronic device commonly used in the first state and the second state ('YES' in the operation 2260), in operation 2270, the electronic device, according to an embodiment, may execute another function corresponding to a third state distinct from the second state, in response to the identified event. For example, when there exists a node connected in common to the first node and the second node, among the nodes corresponding to each of the body parts and the resources of the electronic device, the electronic device may execute another function corresponding to the third state. The node connected in common to the first node and the second node may indicate that the body part and/or the resource of the electronic device corresponding to the node are/is related to both the first state and the second state. Since the body part and/or the resource of the electronic device related to both the first state and the second state exist, performing both the action related to the first state and the action related to the second state by the user may cause overusing of the body part and/or the resource of the electronic device. In order to prevent the overusing, the electronic device, according to an embodiment, may execute another function related to the third state distinguished from the second state, despite the occurrence of an event related to the second state.

When the body parts and/or the resources of the electronic device used in the first state and the second state are distinguished from each other ('NO' in the operation 2260, in operation 2280, the electronic device, according to an embodiment, may execute the function related to the second state, in response to the identified event. For example, when there exists no node connected in common to the first node and the second node among the nodes corresponding to each of the body parts and the resources of the electronic device, the electronic device, according to an embodiment, may execute the function related to the second state. The absence of the node connected in common to the first node and the second node may indicate that the body part and/or the resource of the electronic device are/is related to either one of the first state corresponding to the first node or the second state corresponding to the second node. In such a case, even if the user performs both the action related to the first state and the action related to the second state, the overusing may not occur.

As described above, the electronic device, according to an embodiment, may execute a function based on the resources of both the user and the electronic device to prevent over-using of the resources of both the user and the electronic device. Hereinafter, with reference to FIGS. 23 to 25, detailed description will be made of an operation of the electronic device preventing overusing of resources by both the user and the electronic device, according to an embodiment.

Figure 23:
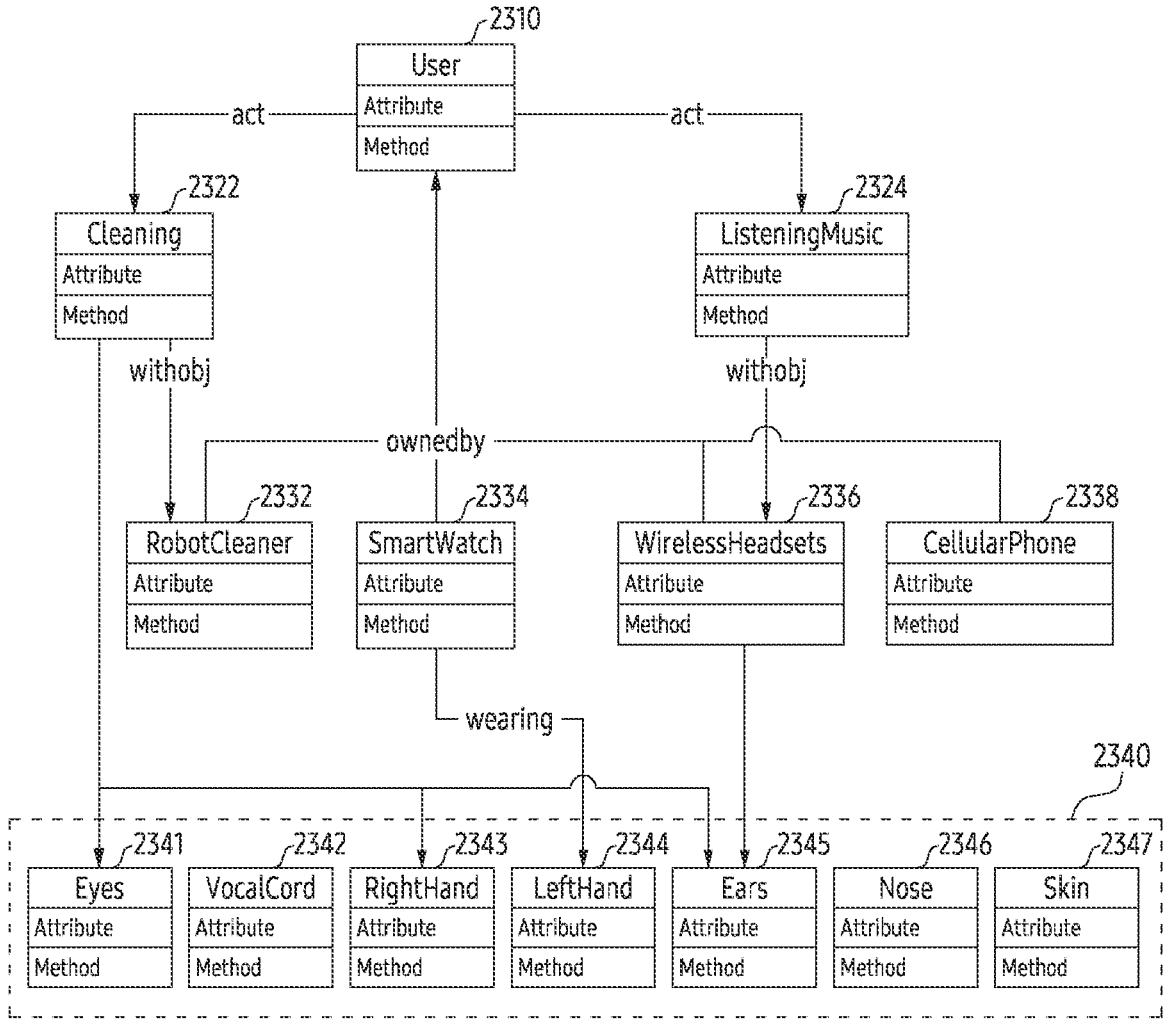
FIG. 23 is a diagram illustrating an operation performed by an electronic device based on a knowledge graph indicating a resource usage of the electronic device, according to an embodiment.

FIG. 23 is an exemplary diagram for explaining an operation performed by an electronic device based on the knowledge graph indicating usage of the resource of the electronic device, according to an embodiment. The electronic device of FIG. 23 may include the electronic devices 101-1, 101-2, 101-3 and 101-4 of FIG. 1 and the electronic device 101 of FIG. 2. The knowledge graph of FIG. 23 may include the knowledge graphs 121, 121-1, 121-2, 122, 123 and 124 of FIG. 1 and/or the knowledge graph 120 of FIG. 2.

Referring to FIG. 23, it is shown part of the knowledge graph stored in the electronic device, while the user performs both the action corresponding to the state of cleaning and the action corresponding to the state of listening to music. The state of cleaning by the user may be identified, for example, based on activation of a robot cleaner (e.g., the electronic device 101-3 of FIG. 1). The state of listening to music by the user may be identified, for example, based on activation of a wireless headset. In response to identifying that the user is in a cleaning state, the electronic device may cause the node 2310 corresponding to the user and the node 2322 corresponding to the state related to the cleaning in the knowledge graph to be connected to each other, based on a predetermined parameter (e.g., act) indicating the current state. In response to identifying that the user is in a state of listening to music, the electronic device may cause the node 2310 corresponding to the user and the node 2324 corresponding to the state of listening to music in the knowledge graph to be connected to each other, based on the predetermined parameter (e.g., act) indicating the current state. For example, the electronic device may perform at least one of the operations 2210 and 2220 of FIG. 22 to obtain a portion of the knowledge graph of FIG. 23.

Referring to FIG. 23, the electronic device, according to an embodiment, may manage the resource of each of a plurality of electronic devices, based on the nodes 2332, 2334, 2336, and 2338 respectively corresponding to a plurality of electronic devices belonging to the user. In a state that the user has a robot cleaner, a smart watch, a wireless headset, and a cellular phone, the electronic device may connect the nodes 2332, 2334, 2336, and 2338 each corresponding to the robot cleaner, the smart watch, the wireless headset, and the cellular phone to the node 2310 corresponding to the user, based on a predetermined parameter (e.g., ownedby) indicating that a corresponding electronic device is personalized to the user. Each of the nodes 2332, 2334, 2336, and 2338 may include attributes indicating a resource of the corresponding electronic device and a state of the resource. Referring to FIG. 23, the node 2322 corresponding to the state of cleaning may be connected to the node 2332 corresponding to a robot cleaner to indicate that the user performs cleaning by using the robot cleaner. Referring to FIG. 23, the node 2324 corresponding to the state of listening to music may be connected to the node 2336 corresponding to a wireless headset to indicate that the user is listening to music, using the wireless headset. For example, when the electronic device listens to music using a cellular phone, the electronic device may connect the node 2338 corresponding to the cellular phone with the node 2324.

Referring to FIG. 23, the electronic device, according to an embodiment, may indicate usage of a body part based on a plurality of nodes 2341, 2342, 2343, 2344, 2345, 2346 and 2347 based on a class 2340 indicating body parts in the knowledge graph. For example, the node 2322 corresponding to the state related to cleaning may be connected to a plurality of nodes 2341, 2343 and 2345 based on the class 2340 to indicate that the state of the user in cleaning is related to his/her eyes, right hand and ears. For example, the node 2324 corresponding to the state of listening to music may be connected to the node 2345 via the node 2336 corresponding to a wireless headset to indicate that the state of the user listening to music is related to the ear.

The electronic device, according to an embodiment, may execute a plurality of functions that can be provided by the electronic device, based on the modes of one or more electronic devices indicated by the knowledge graph. For example, it is assumed that the electronic device receives a signal indicating an incoming call from an external electronic device, in a state that the electronic device corresponds to a cellular phone associated with the node 2338. In response to receiving the signal indicating an incoming call, the electronic device may select any one of the electronic device and/or other electronic devices and output a notification notifying reception of the incoming call, using the knowledge graph. Referring to FIG. 23, based on connections between nodes 2310, 2324, 2336 and 2345, the electronic device, according to an embodiment, may identify activation of the wireless headset.

In response to identifying activation of the wireless headset, the electronic device, according to an embodiment, may identify usage of the ears by the wireless headset, based on the connection between the node 2336 corresponding to the wireless headset and the node 2345 corresponding to the ears. For example, when the intensity between the nodes 2336 and 2345 corresponds to a predetermined intensity indicating exclusive use, the electronic device, according to an embodiment, may identify that the user would be not able to hear a ringing sound generated by a cellular phone (e.g., a cellular phone corresponding to the node 2338) to notify the user of an incoming call. For example, based on the operations 2230, 2240, 2250 and 2260 of FIG. 22, the electronic device, according to an embodiment, may identify that a node corresponding to a state of notifying an incoming call based on a ringing sound is connected to both the node 2345 corresponding to the ears and the current state of listening to music 2324.

The electronic device, according to an embodiment, may, for example, based on the operation 2270 of FIG. 22, execute a function related to another state distinguished from the state of notifying an incoming call with a ringing sound. For example, based on the connection between the node 2334 corresponding to the smart watch and the node 2310 corresponding to the user in the knowledge graph, the electronic device may identify the user's wearing of the smart watch. In this instance, the electronic device may notify reception of an incoming call using the smart watch, instead of notifying the incoming call with a ringing sound through the speaker of the electronic device (e.g., a speaker 260 of FIG. 2) or the wireless headset. For example, the electronic device may notify the user wearing the smart watch of reception of an incoming call, based on a display and/or haptic feedback of the smart watch.

As an example, independent of the above example related to an incoming call, it is assumed that the electronic device receives a text message in a state that the electronic device corresponds to the cellular phone associated with the node 2338. In response to receiving the text message, the electronic device may select any one of the electronic device and/or other electronic devices and output a notification informing the user of reception of the text message using the knowledge graph. In response to identifying activation of the wireless headset from the knowledge graph of FIG. 23, the electronic device, according to an embodiment, may control the wireless headset to notify the user of reception of the text message. In such a case, the function of notifying the reception of the text message may be executed in the wireless headset of the electronic devices respectively corresponding to the nodes 2332, 2334, 2336 and 2338.

As described above, the electronic device, according to an embodiment, may determine whether to execute a plurality of functions that can be provided by the electronic device, based on usage of one or more body parts and/or the resource of one or more electronic devices indicated by the connection of nodes in the knowledge graph. Thus, the electronic device, according to an embodiment, may control execution of a certain function capable of being provided by each of the plurality of electronic devices, based on the usage of the resource of each of one or more body parts and/or a plurality of electronic devices.

Hereinafter, an example of an operation performed by an electronic device based on attributes of each of a plurality of electronic devices that can be identified using a knowledge graph will be described in detail with further reference to FIGS. 24 to 25.

Figure 24:
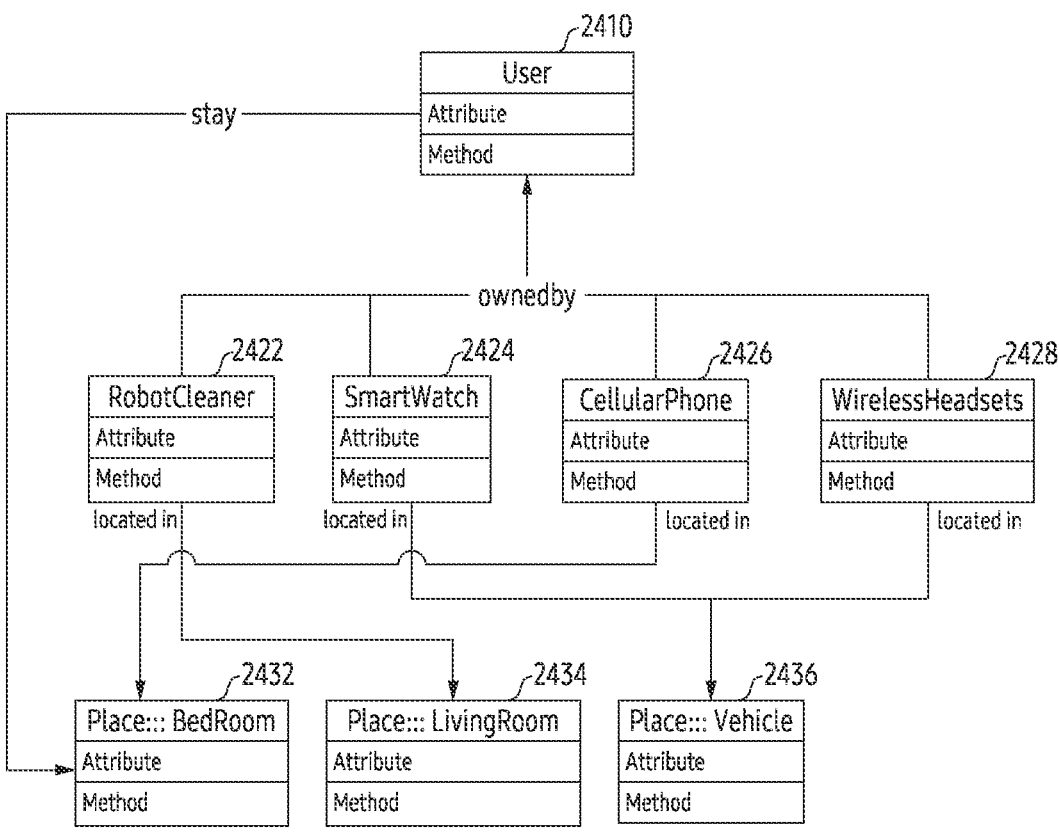
FIG. 24 is a diagram illustrating an operation performed by an electronic device based on a state of the electronic device indicated by a knowledge graph, according to an embodiment.

FIG. 24 is an exemplary diagram for explaining an operation performed by the electronic device based on the state of the electronic device indicated by the knowledge graph, according to an embodiment. The electronic device of FIG. 24 may include the electronic devices 101-1, 101-2, 101-3 and 101-4 of FIG. 1 and the electronic device 101 of FIG. 2. The knowledge graph of FIG. 24 may include the knowledge graphs 121, 121-1, 121-2, 122, 123 and 124 of FIG. 1 and/or the knowledge graph 120 of FIG. 2.

Referring to FIG. 24, it is illustrated an example of the electronic device identifying the states of a plurality of electronic devices related to the user by using the knowledge graph. Based on the history of the user using a robot cleaner, a smart watch, a cellular phone, and a wireless headset, the electronic device may connect nodes 2422, 2424, 2426 and 2428 each corresponding to the robot cleaner, the smart watch, the cellular phone, and the wireless headset in the knowledge graph to the node 2410 corresponding to the user. The electronic device may correspond to any one of the aforementioned robot cleaner, smart watch, cellular phone, and wireless headset, or may be a server connectable over a network, like the electronic device 101-1 of FIG. 1.

Referring to FIG. 24, the electronic device, according to an embodiment, may adjust the attribute of each of nodes 2422, 2424, 2426 and 2428 and/or the connection with other nodes in a knowledge graph, based on the histories of each of the electronic devices corresponding to each the nodes 2422, 2424, 2426 and 2428. For example, based on a location of the robot cleaner obtained by communicating with the robot cleaner and/or the history of last communicating with the robot cleaner, the electronic device may identify that the robot cleaner is located in a living room. In response to identifying that the robot cleaner is located in the living room, the electronic device may cause the node 2422 corresponding to the robot cleaner and the node 2434 corresponding to the living room in the knowledge graph to be connected to each other, based on a predetermined parameter (e.g., locatedin) indicating the location. Similarly, in response to identifying the smart watch located in the vehicle, the electronic device may connect the node 2424 corresponding to the smart watch and the node 2436 corresponding to the vehicle to each other. For example, in response to identifying the cellular phone located in a bedroom, the electronic device may connect the node 2426 corresponding to the cellular phone and the node 2432 corresponding to the bedroom to each other. For example, in response to identifying the wireless headset located in the vehicle, the electronic device may connect the node 2428 corresponding to the wireless headset and the node 2436 corresponding to the vehicle to each other.

The electronic device, according to an embodiment, may select an electronic device to execute a function related to the user of the electronic devices corresponding to each of the nodes 2422, 2424, 2426 and 2428, based on the current state of the user. In an embodiment of FIG. 24, when the user uses his/her cellular phone, the electronic device may identify the user's location, based on the location (e.g., in bedroom) of the cellular phone. In response to identifying the location of the user, the electronic device may connect the node 2410 corresponding to the user and the node 2432 corresponding to the identified location to each other, in the knowledge graph. Subsequent to connecting between the nodes 2410 and 2432, the electronic device receiving a signal indicating an incoming call may select an electronic device to execute a function to notify reception of an incoming call, based on the location of the electronic devices corresponding to each of the nodes 2422, 2424, 2426 and 2428 indicated by the knowledge graph. The electronic device, according to an embodiment, may identify that the node 2410 corresponding to the user is connected to the node 2426 corresponding to the cellular phone via the node 2432 corresponding to the bedroom, in the knowledge graph. Since the connection between the nodes 2410, 2432, and 2426 indicates that both the user and the cellular phone are located in the bedroom, the electronic device, according to an embodiment, may execute a function related to an incoming call of the cellular phone corresponding to the node 2426 among the electronic devices (e.g., a robot cleaner, a smart watch, a cellular phone, and a wireless headset) corresponding to each of the nodes 2422, 2424, 2426 and 2428, respectively.

As described above, the electronic device, according to an embodiment, may track a plurality of electronic devices possessed by one user, using the knowledge graph. Based on the attributes of each of the plurality of electronic devices indicated using the knowledge graph, the electronic device may control each of the plurality of electronic devices belonging to the user.

Figure 25:
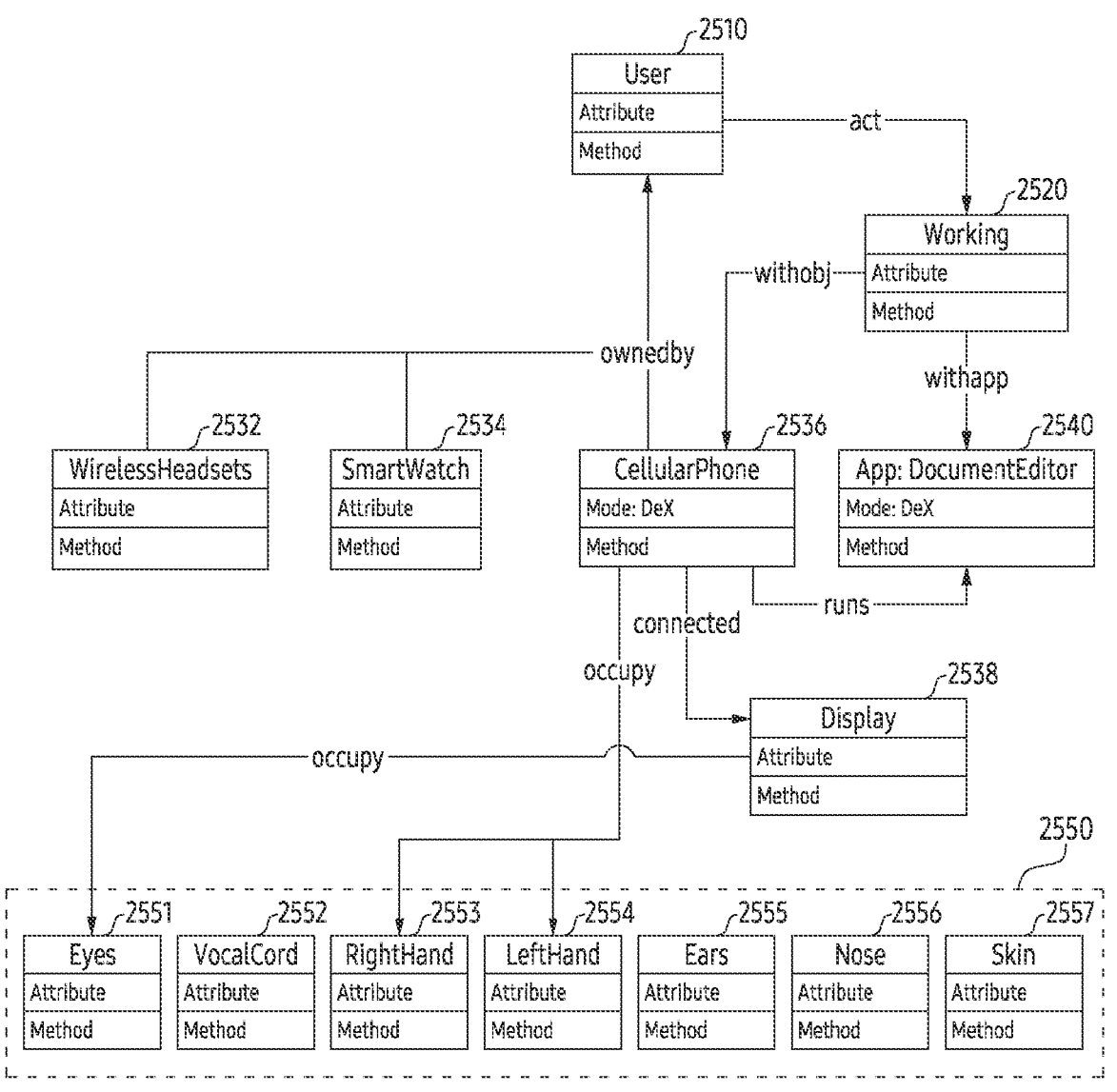
FIG. 25 is a diagram illustrating an operation performed by an electronic device based on a state of the electronic device indicated by a knowledge graph, according to an embodiment.

FIG. 25 is an exemplary diagram for explaining an operation performed by the electronic device based on the state of the electronic device indicated by the knowledge graph, according to an embodiment. The electronic device of FIG. 25 may include the electronic devices 101-1, 101-2, 101-3 and 101-4 of FIG. 1 and the electronic device 101 of FIG. 2. The knowledge graph of FIG. 25 may include the knowledge graphs 121, 121-1, 121-2, 122, 123 and 124 of FIG. 1 and/or the knowledge graph 120 of FIG. 2.

Referring to FIG. 25, it is illustrated an example that an electronic device identifies states of a plurality of electronic devices related to the user using the knowledge graph. For example, based on the user's history of using the wireless headset, the smart watch, and the cellular phone, the electronic device may connect the nodes 2532, 2534, and 2536 respectively corresponding to the wireless headset, the smart watch, and the cellular phone to the node 2510 corresponding to the user, in the knowledge graph. The electronic device may correspond to any one of the aforementioned wireless headset, smart watch, and cellular phone, or may be a server disposed over a network like the electronic device 101-1 of FIG. 1.

Referring to FIG. 25, the electronic device, according to an embodiment, may update the knowledge graph, based on the modes of the electronic devices corresponding to each of the nodes 2532, 2534 and 2536. For example, based on the mode of the cellular phone corresponding to the node 2536, the electronic device according to one embodiment may adjust the attributes of the node 2536 and/or the connection in between the node 2536 and other nodes, in the knowledge graph. For example, in response to identifying a state that the user connects the cellular phone with an external display to extend its display area to the external display, the electronic device, according to an embodiment, may connect the node 2536 corresponding to the cellular phone and the node 2538 corresponding to the external display to each other, in the knowledge graph Referring to FIG. 25, the electronic device may allocate, to the node 2536, a predetermined parameter (e.g., DeX) indicating that the device operates in a mode of connecting the external display thereto. The electronic device may change at least a portion of the knowledge graph, based on the user's state related to the cellular phone.

For example, while the user executes a text editor (e.g., a document editor app) in a state that the cellular phone and the external display are connected to each other, in the knowledge graph, the electronic device may connect a node 2540 corresponding to the text editor and the node 2536 corresponding to the cellular phone and connect a node 2520 indicating a working state and a node 2510 corresponding to the user, to each other. Referring to FIG. 25, the node 2520 indicating a working state may be connected to the node 2536 corresponding to the cellular phone and the node 2540 corresponding to the text editor to indicate that the user in a working state uses his/her cellular phone to edit using the text editor. Since the user is using his/her cellular phone and the external display, among the nodes 2551, 2552, 2553, 2554, 2555, 2556 and 2557 included in the class 2550 indicating body parts in the knowledge graph, the electronic device may connect the node 2536 corresponding to the cellular phone and the nodes 2553 and 2554 corresponding to both hands of the user to each other and connect the node 2538 corresponding to the external display and the node 2551 corresponding to the eyes to each other.

In a state in which part of the knowledge graph is connected as shown in FIG. 25, the electronic device, according to an embodiment, may adjust execution of one or more functions, based on the resource of the user and/or the electronic device identified by the knowledge graph. For example, in response to detecting occurrence of an event for receiving an e-mail, the electronic device may determine how to execute the function related to the event (e.g., a function for notifying reception of an e-mail), based on the knowledge graph of FIG. 25. For example, since the node 2551 corresponding to the user's eyes is connected to the node 2538 corresponding to the external display, the electronic device may control the cellular phone to display a window to inform of reception of the e-mail in the external display of the display of the cellular phone or the external display. As much as possible, the user can control the cellular phone.

As described above, the electronic device, according to an embodiment, may recognize a mode of a plurality of electronic devices possessed by one user, using the knowledge graph. Based on the recognized mode of each of the plurality of electronic devices, the electronic device may selectively execute the function capable of being provided by each of the plurality of electronic devices.

As described above, a method of an electronic device, according to an embodiment, may include obtaining, from a memory of the electronic device, information indicating a usage relationship between distinct states of a user of the electronic device and at least one body part; identifying a first state of the user corresponding to a first function among a plurality of functions executable by the electronic device; identifying an event for executing a second function different from the first function; comparing, in response to identifying the event, a first body part used by the user associated with the first state and a second body part used by the user associated with a second state corresponding to the second function, based on the obtained information, and executing, in response to the identified event, a third function indicated in the information as being associated with the second function, based on a result of the comparing of the first body part and the second body part.

In an embodiment, the information obtained from the memory may indicate a knowledge graph indicating usage of the at least one body part in each of the distinct states, based on connection between nodes respectively corresponding to the distinct states and the at least one body part.

In an embodiment, the usage may correspond to at least one of a first type of parameter in indicating exclusive use of a body part by the user and a second type of parameter indicating partial use of a body part by the user.

In a method of an electronic device, according to an embodiment, the identifying the first state further may include identifying a first node, based on the obtained information indicating sequential connection between nodes respectively corresponding to the distinct states of the user, corresponding to the first state, and the comparing of the first body part and the second body part may further include identifying the first body part, by extracting one or more nodes connected to the identified first node, based on the obtained information.

In a method of an electronic device, according to an embodiment, the identifying the event may further include identifying occurrence of the event, in response to receiving a signal indicating at least one of an incoming call, an electronic mail or a text message, from an external electronic device distinct form the electronic device via a communication circuitry of the electronic device.

In an method of an electronic device, according to an embodiment, the comparing of the first body part and the second body part may further include identifying, based on the obtained information, a first node corresponding to the first state and a second node corresponding to the second state; identifying, based on the obtained information, one or more nodes coupled to each of the first node and the second node; and identifying, in response to identifying a node that is commonly coupled to the first node and the second node, among the identified one or more nodes, whether the first body part and the second body part correspond to each other.

In a method of an electronic device, according to an embodiment, the executing the third function may further include identifying, in response to identifying that the first body part and the second body part correspond to each other, one or more other nodes included in a hierarchy corresponding to the second node, based on hierarchical connection of nodes respectively corresponding to the distinct states in the information; identifying, in response to identifying the one or more other nodes, a third node independent of the first body part among the identified one or more other nodes; and executing, in response to identifying of the third node, the third function corresponding to the third node.

A method of an electronic device, according to an embodiment, may further include executing the second function as a response to the identified event, in response to identifying that the first body part and the second body part are distinguished from each other.

A method of an electronic device, according to an embodiment, may further include executing a fourth function for adjusting the first function that has been executed by the user, based on a result of comparing the first body part and the second body part.

In a method of an electronic device, according to an embodiment, the executing of the fourth function may further include executing the fourth function, in response to identifying that the first body part and the second body part correspond to each other, and identifying that a priority of the second function indicated by the information is higher than a priority of the first function indicated by the information.

An electronic device, according to an embodiment, may include a memory; and at least one processor operably coupled to the memory, where the memory may include one or more instructions that cause, when executed by the at least one processor, the at least one processor to obtain, from the memory, information indicating usage relationship between distinct states of a user of the electronic device and at least one body part; identify a first state of the user corresponding to a first function among a plurality of functions executable by the electronic device; identify an event for executing a second function different from the first function; compare, in response to identifying the event, a first body part used by the user associated with the first state and a second body part used by the user associated with a second state corresponding to the second function, based on the obtained information; and execute, in response to the identified event, a third function indicated in the information as being associated with the second function, based on a result of the comparing the first body part and the second body part.

In an electronic device, according to an embodiment, the information obtained from the memory may indicate a knowledge graph indicating usage of the at least one body part in each of the distinct states, based on connection between nodes respectively corresponding to the distinct states and the at least one body part.

In an electronic device, according to an embodiment, the usage may correspond to at least one of a first type of parameter in indicating exclusive use of a body part by the user and a second type of parameter indicating partial use of a body part by the user.

In an electronic device, according to an embodiment, the memory may store the one or more instructions that, when executed by the at least one processor, further cause the at least one processor to identify a first node corresponding to the first state, based on the obtained information indicating sequential connection between nodes respectively corresponding to the distinct states of the user, and identify the first body part, based on the obtained information, by extracting one or more nodes connected to the identified first node.

In an electronic device, according to an embodiment, the memory may store the one or more instructions that, when executed by the at least one processor, further cause the at least one processor to identify, based on the obtained information, a first node corresponding to the first state and a second node corresponding to the second state; identify, based on the obtained information, one or more nodes coupled to each of the first node and the second node; and identify, in response to identifying a node that is commonly coupled to the first node and the second node, among the identified one or more nodes, whether the first body part and the second body part correspond to each other.

In an electronic device according to an embodiment, the memory may store the one or more instructions that, when executed by the at least one processor, further cause the at least one processor to identify, in response to identifying that the first body part and the second body part correspond to each other, one or more other nodes included in a hierarchy corresponding to the second node, based on hierarchical connection of nodes respectively corresponding to the distinct states in the information; identify, in response to the identifying of the one or more other nodes, a third node independent of the first body part among the identified one or more other nodes; and execute, in response to identifying the third node, the third function corresponding to the third node.

In an electronic device, according to an embodiment, the memory may store the one or more instructions that, when executed by the at least one processor, further cause the at least one processor to execute a fourth function, based on a result of the comparing the first body part and the second body part, to adjust the first function that has been executed by the user.

An electronic device, according to an embodiment, may include a communication circuitry; a memory; and at least one processor operably coupled to the communication circuitry and the memory, where the memory may stores one or more instructions that cause, when executed by the at least one processor, cause the at least one processor to obtain, from the memory, information indicating usage relationship between distinct states of a user of the electronic device and at least one body part; identify, based on the obtained information, one or more first body parts used by the user in a first state associated with a first function that has been executed by the electronic device, among the distinct states; receive, from an external electronic device via the communication circuitry, a signal requesting outputting a notification message to the user; identify, in response to receiving of the signal, change in usage of the one or more first body parts according to a second state, among the distinct states, indicating receiving of the notification message of the user, based on the obtained information; provide, in response to identifying the change in usage of the one or more first body parts, a first control signal for adjusting the first function; and output, while providing the first control signal, the notification message based on the received signal to the user.

In an electronic device, according to an embodiment, the information obtained from the memory may indicate a knowledge graph indicating usage of the at least one body part in each of the distinct states, based on connection between nodes respectively corresponding to the distinct states and the at least one body part.

In an electronic device, according to an embodiment, the memory may store the one or more instructions that, when executed by the at least one processor, further cause the at least one processor to provide, in response to identifying the change in usage of the one or more first body part, the notification message to the user, based on a second function associated with a second body part independent of the one or more first body part.

A method of an electronic device, according to an embodiment, may include, in a memory of the electronic device, obtaining information indicating a usage relationship between distinct states of a user of the electronic device and at least one body part; based on the obtained information, identifying, among the states, one or more first body parts being used by the user in a first state related to a first function being executed by the electronic device; receiving a signal requesting outputting of a notification message to the user from an external electronic device through a communication circuitry of the electronic device; in response to receiving the signal, identifying a change in usage of the one or more first body parts according to a second state indicating reception of the notification message of the user among the states, based on the obtained information; providing a first control signal for adjusting the first function, in response to identifying the change in usage of the one or more first body parts; and while providing the first control signal, outputting the notification message based on the received signal to the user.

A computer program product, according to an embodiment, may include a computer-readable recording medium, the computer-readable recording medium including instructions which are readable by at least one processor of an electronic device to cause the at least one processor to: obtain information indicating a usage relationship between distinct states of a user of the electronic device and at least one body part; identify a first state of the user corresponding to a first function among a plurality of functions executable by the electronic device; identify an event for executing a second function different from the first function; compare, in response to identifying the event, a first body part used by the user associated with the first state and a second body part used by the user associated with a second state corresponding to the second function, based on the obtained information; and execute, in response to the identified event, a third function indicated in the information as being associated with the second function, based on a result of the comparing.

The computer program product, according to an embodiment, may include where the obtained information indicates at least one knowledge graph indicating a usage of the at least one body part in each of the distinct states, based on a connection between nodes respectively corresponding to the distinct states and the at least one body part; and further where the usage corresponds to at least one of a first type of parameter in indicating exclusive use of a body part by the user and a second type of parameter indicating partial use of a body part by the user.

A method of an electronic device, according to an embodiment, includes identifying a first state of a user corresponding to a first function based on information indicated in a knowledge graph; identifying an event to execute a second function related to a second state distinguished from the first state of the user corresponding to the first function; determining whether a body part related to both the first state and the second state exists in the knowledge graph; identifying a candidate state distinguished from the second state in response to determining that the body part related to both the first state and the second state exists in the knowledge graph; and executing a third function corresponding to the candidate state related to another body part, in response to the identified event.

The method, according to an embodiment, may include ceasing the first function and executing the second function in response to the identified event based on determining that the candidate state is non-existent, a priority of the second state is higher than the first state, and the body part related to both the first state and the second state is used in the first state.

The method, according to an embodiment, may include executing a fourth function to reduce use of the body part associated with both the first state and the second state by the first function associated with the first state based on determining that the candidate state is non-existent, the priority of the second state is higher than the first state, and the body part related to both the first state and the second state is non-exclusively used in the first state.

The devices described heretofore may be implemented as hardware components, or software components, and/or a combination of the hardware components and the software components. For example, the devices and components described in the embodiments may be implemented using one or more general-purpose or special-purpose of computers, such as e.g., a processor, a controller, an arithmetic logic unit (ALU), a digital signal processor (DSP), a microcomputer, a field programmable gate array (FPGA), a programmable logic unit (PLU), a microprocessor, or any other device capable of executing and responding to instructions. A processing unit/device may execute an operating system (OS) and one or more software applications running on the operating system. Further, the processing unit may access, store, manipulate, process, and generate data in response to execution of the software. For convenience of understanding, although it is sometimes described that a single processing unit is used, one of ordinary knowledge in the art will appreciate that the processing unit may include a plurality of processing elements and/or plural types of such processing elements. For example, the processing unit may include multiple processors or a single processor and at least one controller. Other processing configurations may be also possible, such as a parallel processor.

The software may include computer programs, codes, instructions, or a combination of one or more of the same, and configure a processing unit to operate as desired or command the processing unit independently or collectively. The software and/or data may be embodied in any type of machine, component, physical device, computer storage medium or device for interpretation by the processing unit or providing instructions or data to thereto. The software may be distributed over networked computer systems and stored or executed in a distributed manner. Software and data may be stored in one or more computer-readable recording media.

A method according to various embodiments may be implemented in the form of program instructions that can be executed through various computer means and recorded in a computer-readable medium. In this instance, the medium may be to continuously store the computer-executable program, or to temporarily store the program for execution or download. Further, the medium may be various recording means or storage means in the form of a single or several hardware combined together, which is not limited to a medium directly connected to any computer system and may exist distributed over a network. Examples of the recording media may include a magnetic medium such as e.g., a hard disk, a floppy disk and a magnetic tape, an optical recording medium such as e.g., compact disc read only memory (CD-ROM) and digital versatile disc (DVD), a magneto-optical medium such as e.g., a floptical disk, and those configured to store program instructions, such as e.g., ROM, RAM, flash memory, and the like. In addition, examples of other recording media may include recording media or storage media managed by an app stores distributing applications, websites supplying or distributing various other software, and servers.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., CD-ROM, DVD, a universal serial bus (USB) drive, or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

A computer-readable storage medium may be provided in the form of a non-transitory storage medium that stores executable instructions of a computer program product. Here, the term 'non-transitory' simply means that the storage medium is a tangible device, and does not include a signal, but this term does not differentiate between where data is semi-permanently stored in the storage medium and where the data is temporarily stored in the storage medium. For example, the non-transitory storage medium may include a buffer in which data is temporarily stored.

As described above, although the exemplary embodiments have been described with reference to some limited embodiments and drawings, various modifications and changes may be made from the above description by those skilled in the art. For example, although the techniques described above are performed in an order different from the described methods, and/or the elements such as the described system, structure, apparatus, circuit, etc. are coupled or combined in a different form than the described method, and/or replaced or substituted by other components or equivalents thereof, an appropriate result can be achieved.

Therefore, any other implementations, alternative embodiments, and/or equivalents to those claims will fall within the scope of the following claims.

What is claimed is:

1. A method of an electronic device, comprising:
obtaining, from a memory of the electronic device, information indicating a usage relationship between distinct states of a user of the electronic device and at least one body part;
identifying a state of the user;
based on identifying a first state of the user, identifying a first body part that is indicated by the information as being used by the user in the first state;
identifying an event for executing a first function among a plurality of functions executable by the electronic device;
identifying, based on the event, a body part that is indicated by the information as being used by the user with respect to the first function; and
based on the identified body part corresponding to the first body part, executing a second function among the plurality of functions that is indicated by the information as being associated with the first function, wherein the second function is indicated by the information as being associated with a second body part different from the first body part and is executed as a replacement of the first function while the first state is maintained, and
wherein the identifying the body part that is indicated by the information as being used by the user with respect to the first function further comprises:
identifying, based on the obtained information, a first node corresponding to the first state and a second node corresponding to a second state corresponding to the first function;
identifying, based on the obtained information, one or more nodes coupled to each of the first node and the second node; and
identifying, in response to identifying a node that is commonly coupled to the first node and the second node, among the identified one or more nodes, whether the body part corresponds to the first body part.

2. The method of claim 1, wherein the information obtained from the memory indicates at least one knowledge graph indicating a usage of the at least one body part in each of the distinct states, based on a connection between nodes respectively corresponding to the distinct states and the at least one body part.

3. The method of claim 2, wherein the usage corresponds to one of a first usage type indicating exclusive use of a body part by the user or a second usage type indicating partial use of a body part by the user.

4. The method of claim 1,
wherein the identifying the first state further comprises identifying a first node, based on the obtained information indicating a sequential connection between nodes respectively corresponding to the distinct states of the user, corresponding to the first state, and
wherein the identifying the first body part further comprises identifying the first body part, based on the obtained information, by extracting one or more nodes connected to the identified first node.

5. The method of claim 1, wherein the identifying the event further comprises identifying an occurrence of the event, in response to receiving a signal indicating at least one of an incoming call, an electronic mail or a text message, from an external electronic device distinct from the electronic device via a communication circuitry of the electronic device.

6. The method of claim 1, wherein the executing the second function further comprises:

identifying, based on the identified body part corresponding to the first body part, one or more other nodes included in a hierarchy corresponding to the second node, based on a hierarchical connection of nodes respectively corresponding to the distinct states in the information;

identifying, in response to identifying the one or more other nodes, a third node independent of the first body part among the identified one or more other nodes; and executing, in response to identifying of the third node, the second function corresponding to the third node.

7. The method of claim 1, further comprising executing the first function as a response to the identified event, based on the identified body part different from the first body part.

8. The method of claim 1, further comprising executing a third function for adjusting the first function that has been executed by the user, based on the identified body part.

9. The method of claim 8, wherein the executing the third function further comprises executing the third function, based on the identified body part corresponding to the first body part, and identifying that a priority of the third function indicated by the information is higher than a priority of the second function indicated by the information.

10. An electronic device, comprising:

memory including one or more storage media storing instructions; and at least one processor including processing circuitry, wherein the instructions, when executed by the at least one processor individually or collectively, cause the electronic device to:

obtain, from the memory, information indicating a usage relationship between distinct states of a user of the electronic device and at least one body part;

identify a state of the user;

based on identifying a first state of the user, identify a first body part that is indicated by the information as being used by the user in the first state;

identify an event for executing a first function among a plurality of functions executable by the electronic device;

identify, based on the event, a body part that is indicated by the information as being used by the user with respect to the first function; and based on the identified body part corresponding to the first body part, execute a second function among the plurality of functions that is indicated by the information as being associated with the first function, wherein the second function is indicated by the information as being associated with a second body part different from the first body part and is executed as a replacement of the first function while the first state is maintained, and wherein the identifying the body part that is indicated by the information as being used by the user with respect to the first function further comprises:

identifying, based on the obtained information, a first node corresponding to the first state and a second node corresponding to a second state corresponding to the first function;

identifying, based on the obtained information, one or more nodes coupled to each of the first node and the second node; and identifying, in response to identifying a node that is commonly coupled to the first node and the second node, among the identified one or more nodes, whether the body part corresponds to the first body part.

11. The electronic device of claim 10, wherein the information obtained from the memory indicates a knowledge graph indicating a usage of the at least one body part in each of the distinct states, based on a connection between nodes respectively corresponding to the distinct states and the at least one body part.

12. The electronic device of claim 11, wherein the usage corresponds to one of a first usage type indicating exclusive use of a body part by the user or a second usage type indicating partial use of a body part by the user.

13. The electronic device of claim 10, wherein the memory includes the one or more instructions that further cause, when executed by the at least one processor, the at least one processor to:

identify a first node corresponding to the first state, based on the obtained information indicating a sequential connection between nodes respectively corresponding to the distinct states of the user; and identify the first body part, based on the obtained information, by extracting one or more nodes connected to the identified first node.

14. The electronic device of claim 10, wherein the one or more instructions, when executed by the at least one processor, further cause the at least one processor to:

identify, based on the identified body part corresponding to the first body part, one or more other nodes included in a hierarchy corresponding to the second node, based on a hierarchical connection of nodes respectively corresponding to the distinct states in the information;

identify, in response to the identifying of the one or more other nodes, a third node independent of the first body part among the identified one or more other nodes; and execute, in response to identifying the third node, the second function corresponding to the third node.

15. The electronic device of claim 10, wherein the one or more instructions, when executed by the at least one processor, further cause the at least one processor to:

execute a third function, based on the identified body part, to adjust the first function that has been executed by the user.

* * * * *